(12) United States Patent
Xu et al.

(10) Patent No.: US 12,139,747 B2
(45) Date of Patent: Nov. 12, 2024

(54) KIT AND DEVICE FOR USE WITH GENE DETECTION TECHNIQUES AND TESTING

(71) Applicant: HANGZHOU ALLSHENG INSTRUMENTS CO., LTD., Zhejiang (CN)

(72) Inventors: Tao Xu, Zhejiang (CN); Zhicheng Luo, Zhejiang (CN); Xuhao Yu, Zhejiang (CN); Kaixuan Wang, Zhejiang (CN); Weidong Fan, Zhejiang (CN); Guangjin Luo, Zhejiang (CN)

(73) Assignee: HANGZHOU ALLSHENG INSTRUMENTS CO., LTD., Zhejiang (CN)

( * ) Notice: Subject to any disclaimer, the term of this patent is extended or adjusted under 35 U.S.C. 154(b) by 0 days.

(21) Appl. No.: 17/948,804

(22) PCT Filed: Feb. 11, 2022

(86) PCT No.: PCT/CN2022/076074
§ 371 (c)(1),
(2) Date: Sep. 20, 2022

(87) PCT Pub. No.: WO2023/000654
PCT Pub. Date: Jan. 26, 2023

(65) Prior Publication Data
US 2023/0015329 A1   Jan. 19, 2023

(30) Foreign Application Priority Data

Jul. 19, 2021   (CN) .......................... 202110813153.8
Dec. 2, 2021    (CN) .......................... 202111457405.4

(51) Int. Cl.
*C12Q 1/6806*   (2018.01)
*B01L 3/00*     (2006.01)

(52) U.S. Cl.
CPC ............ *C12Q 1/6806* (2013.01); *B01L 3/502* (2013.01); *B01L 2200/021* (2013.01);
(Continued)

(58) Field of Classification Search
CPC ..... C12Q 1/6806; C12Q 1/6844; B01L 3/502; B01L 2200/021; B01L 2200/025;
(Continued)

(56) References Cited

U.S. PATENT DOCUMENTS 7,887,308 B2 *   2/2011  Navarro .................... F04B 9/02
                                                    417/538
2004/0197233 A1* 10/2004 Nagaoka ............... G01N 35/025
                                                    422/81
(Continued)

FOREIGN PATENT DOCUMENTS

CN    103923817 A    7/2014
CN    104673625 A    6/2015
(Continued)

OTHER PUBLICATIONS

International Search Report for the International Application No. PCT/CN2022/076074 issued by the Chinese Patent Office on May 9, 2022.
(Continued)

*Primary Examiner* — Jill A Warden
*Assistant Examiner* — Jacqueline Brazin
(74) *Attorney, Agent, or Firm* — IP & T GROUP LLP

(57) ABSTRACT

Provided are a gene detection kit and a gene detection device. The gene detection kit includes a kit body, a piston cylinder, and a piston. The kit body has an accommodating cavity and a plurality of reagent cavities. The piston cylinder is provided in the accommodating cavity, and the piston cylinder has a piston cavity. The piston is movably provided in the piston cavity along an axial direction of the piston (Continued)

cylinder. A first channel in communication with the piston cavity is provided on an outer circumferential surface of the piston cylinder, a plurality of second channels are provided on an inner wall of the accommodating cavity, each of the second channels is in corresponding communication with one of the reagent cavities, and the piston cylinder can move relative to the kit body, so that the plurality of second channels are alternately in communication with the first channel.

18 Claims, 24 Drawing Sheets

(52) U.S. Cl.
CPC ... *B01L 2200/025* (2013.01); *B01L 2200/026* (2013.01); *B01L 2200/0621* (2013.01); *B01L 2200/0636* (2013.01); *B01L 2200/0642* (2013.01); *B01L 2200/14* (2013.01); *B01L 2200/16* (2013.01); *B01L 2300/0832* (2013.01); *B01L 2300/0867* (2013.01); *B01L 2300/087* (2013.01); *B01L 2400/043* (2013.01)

(58) Field of Classification Search
CPC ....... B01L 2200/026; B01L 2200/0621; B01L 2200/0636; B01L 2200/0642; B01L 2200/14; B01L 2200/16; B01L 2300/0832; B01L 2300/0867; B01L 2300/087; B01L 2400/043; B01L 7/00; B01L 2200/0689; B01L 2200/10; B01L 2300/043; B01L 2300/0874; B01L 2300/1805; B01L 2400/0478; B01L 2400/0644; B01L 7/52; C12N 15/1013
USPC ......................................................... 422/505
See application file for complete search history.

(56) References Cited

U.S. PATENT DOCUMENTS

| 2006/0099111 A1* | 5/2006 | Kikuchi | G01N 21/0303 |
| | | | 422/68.1 |
| 2014/0235504 A1* | 8/2014 | Sacher | B01L 7/52 |
| | | | 435/6.12 |

FOREIGN PATENT DOCUMENTS

| CN | 105695303 A | 6/2016 |
| CN | 111394221 A | 7/2020 |
| CN | 111602060 A | 8/2020 |
| CN | 111704993 A | 9/2020 |
| CN | 112538414 A | 3/2021 |
| CN | 112844505 A | 5/2021 |
| CN | 113430096 A | 9/2021 |
| CN | 113913271 A | 1/2022 |
| JP | 2010217102 A | 9/2010 |

OTHER PUBLICATIONS

Written Opinion for the International Application No. PCT/CN2022/076074 issued by the Chinese Patent Office on May 9, 2022.
First Office Action on the Chinese Patent Application No. 202111457405.4 issued by the Chinese Patent Office on Mar. 8, 2022 and first Search Report thereof.
Second Office Action on the Chinese Patent Application No. 202111457405.4 issued by the Chinese Patent Office on Jun. 2, 2022.
Notification to Grant Patent Rights for the Chinese Patent Application No. 202111457405.4 issued by the Chinese Patent Office on Aug. 3, 2022.
International Search Report and Written opinion for the International Patent Application No. PCT/CN2022/076074 issued by the International Searching Authority on May 19, 2022.

* cited by examiner

KIT AND DEVICE FOR USE WITH GENE DETECTION TECHNIQUES AND TESTING

CROSS-REFERENCE TO RELATED APPLICATION

The present disclosure is a national stage application of PCT/CN2022/076074 filed on Feb. 11, 2022, which claims the priority to the Chinese patent application with the filing No. "CN202110813153.8" filed on Jul. 19, 2021 with the Chinese Patent Office and entitled "Fully Enclosed Sample Processing and Detection Device" and the Chinese patent application with the filing No. "202111457405.4" filed on Dec. 2, 2021 with the Chinese Patent Office and entitled "Gene Detection Kit and Dene Detection Device", the contents of which are incorporated herein by reference in entirety.

TECHNICAL FIELD

The present disclosure relates to the technical field of gene detection, and in particular, to a gene detection kit and a gene detection device.

BACKGROUND ART

As relatively accurate detection means, gene detection is mainly applied in aspects such as disease detection and substance analysis. It is now known that human diseases are all directly or indirectly related to genes, and detection and analysis of genes are increasingly used widely in fields such as genetic diseases, tumors, and infectious diseases, thereby the disease diagnosis modes and treatment strategies are updated, and the pathogenesis of diseases related to gene structure or expression abnormalities can be revealed, thus, the gene detection has been widely applied in fields such as biomedicine.

A gene detection process includes sample acquisition, nucleic acid extraction of the sample (sample lysing, washing, drying, elution, and PCR amplification (performing polymerase chain reaction for the nucleic acid), etc.), and gene detection. However, in the conventional gene detection process, multiple steps of nucleic acid extraction need to be operated on different instruments, then the sample or reagent needs to be transferred multiple times, thus increasing the possibility of cross-contamination of the samples, and further leading to an inaccurate gene detection result, and bringing quite serious harm to patients.

SUMMARY

The present disclosure provides a gene detection kit, including:
- a kit body, wherein the kit body has an accommodating cavity and a plurality of reagent cavities;
- a piston cylinder, wherein the piston cylinder is provided in the accommodating cavity, and the piston cylinder has a piston cavity; and
- a piston, wherein the piston is movably provided in the piston cavity along an axial direction of the piston cylinder, wherein
- a first channel in communication with the piston cavity is provided on an outer circumferential surface of the piston cylinder, a plurality of second channels are provided on an inner wall of the accommodating cavity, each of the second channels is in corresponding communication with one of the reagent cavities, and the piston cylinder can move relative to the kit body, so that the plurality of second channels are alternately in communication with the first channel.

In some embodiments, when the first channel is in communication with any one of the second channels, the remaining second channels are blocked by the outer circumferential surface of the piston cylinder.

In some embodiments, the gene detection kit further includes a first sealing member; and
- the first sealing member is sleeved on the outer circumferential surface of the piston cylinder, and the first sealing member is provided with a first through hole in communication with the first channel at a position corresponding to the first channel.

In some embodiments, the outer circumferential surface of the piston cylinder is provided thereon with a first annular groove extending along the circumferential direction of the piston cylinder; and
- the first annular groove is configured to accommodate the first sealing member, and the first channel is provided on a groove bottom wall of the first annular groove.

In some embodiments, in the axial direction of the piston cylinder, one end of the piston cylinder is provided with a first receptacle into which a piston rod is inserted, the first receptacle is provided opposite to a bottom surface of the piston cavity, the bottom surface of the piston cavity gradually gets away from the first receptacle from an edge to a center, and the first channel is connected to the center of the bottom surface of the piston cavity.

In some embodiments, a magnetic bead retention tank configured to accommodate magnetic beads is provided on the bottom surface of the piston cavity; and
- in the axial direction of the piston cylinder, the magnetic bead retention tank is closer to the first receptacle than the center of the bottom surface of the piston cavity.

In some embodiments, the piston cylinder includes a cylinder body and a partition wall; and
- the partition wall is provided in the cylinder body and divides an inner space of the cylinder body into the piston cavity and a magnetic cavity, the piston cavity and the magnetic cavity are arranged along an axial direction of the cylinder body, the cylinder body has a first receptacle and a second receptacle at two ends in the axial direction thereof, the first receptacle is configured to allow the piston rod to be inserted into the piston cavity, the second receptacle is configured to allow a magnetic member to be inserted into the magnetic cavity, and the magnetic member is configured to adsorb the magnetic beads.

In some embodiments, the plurality of reagent cavities are arranged along the circumferential direction of the piston cylinder.

In some embodiments, each of the reagent cavities has an opening at one end in the axial direction of the piston cylinder; and
- the plurality of reagent cavities include a lysing cavity, a washing cavity, an elution cavity, and a product output cavity, in the axial direction of the piston cylinder, bottom surfaces of the lysing cavity, the washing cavity, and the elution cavity are provided opposite to respective openings, and the bottom surfaces of the lysing cavity, the washing cavity, and the elution cavity are all inclined surfaces, and are gradually away from respective openings from a side away from the piston cylinder to a side close to the piston cylinder, and the second channels are connected to a side of the inclined surface close to the piston cylinder.

In some embodiments, the plurality of reagent cavities further include a magnetic bead cavity; and the lysing cavity, the magnetic bead cavity, the washing cavity, the elution cavity, and the product output cavity are sequentially arranged along the circumferential direction of the piston cylinder.

In some embodiments, the plurality of reagent cavities further include a drying cavity; and the lysing cavity, the washing cavity, the drying cavity, the elution cavity, and the product output cavity are sequentially arranged along the circumferential direction of the piston cylinder.

In some embodiments, the gene detection kit further includes an amplification reaction tube; and the amplification reaction tube is connected to the kit body, the product output cavity is in communication with a corresponding one of the second channels through the amplification reaction tube, and the amplification reaction tube is configured to amplify the nucleic acid.

In some embodiments, the kit body further has a third channel in communication with the product output cavity; and the amplification reaction tube has an inlet and an outlet, wherein the inlet is in communication with the second channel corresponding to the product output cavity, and the outlet is in communication with the third channel.

In some embodiments, the piston cylinder can be circumferentially rotated relative to the kit body, such that the plurality of second channels are alternately in communication with the first channel.

In some embodiments, the outer circumferential surface of the piston cylinder is provided with a limiting protrusion in a protruding way; and a limiting groove is provided on the inner wall of the accommodating cavity, and the limiting groove is configured to be snapped with the limiting protrusion, so as to restrict axial movement of the piston cylinder relative to the kit body.

In some embodiments, the limiting protrusion and the limiting groove are both of annular structures extending along the circumferential direction of the piston cylinder.

In some embodiments, the accommodating cavity penetrates through the kit body along the axial direction of the piston cylinder; and one end of the piston cylinder has the first receptacle into which the piston rod is inserted, one end of the piston cylinder, far away from the first receptacle in the axial direction thereof, extends out from the kit body and has an operation portion, wherein the operation portion is configured to be connected to a driving mechanism so as to drive the piston cylinder to circumferentially rotate relative to the kit body.

In some embodiments, the gene detection kit further includes a base; and the base is provided with an accommodating groove, one end of the kit body close to the operation portion in the axial direction of the piston cylinder is inserted into the accommodating groove, a first avoidance hole is provided in a groove bottom wall of the accommodating groove, and the first avoidance hole is configured to allow one end of the piston cylinder away from the first receptacle to extend out.

In some embodiments, the gene detection kit further includes a locking member; and the locking member is mounted on the base, and the locking member is configured to be connected to the operation portion so as to prevent the piston cylinder from circumferentially rotating relative to the kit body.

In some embodiments, the outer circumferential surface of the base is provided with an insertion slot into which the locking member is inserted along the radial direction of the piston cylinder; and the operation portion is wedge-shaped, the locking member has a wedge-shaped notch, and when the locking member is inserted into the insertion slot, the wedge-shaped notch is snapped with the operation portion, so as to prevent the piston cylinder from circumferentially rotating relative to the kit body.

In some embodiments, the base is provided with a positioning hole; and the locking member is provided with a positioning boss, and when the locking member is inserted into the insertion slot, the positioning boss cooperates with the positioning hole so as to prevent the locking member from being detached from the insertion slot.

In some embodiments, the locking member includes a locking portion and a hand-held portion;

the locking portion has the wedge-shaped notch, the locking portion is configured to be inserted into the insertion slot so as to lock the operation portion; and the hand-held portion extends out from the outer circumferential surface of the base, and a plurality of anti-slip stripes are provided on the hand-held portion.

In some embodiments, each of the reagent cavities has an opening at one end in the axial direction of the piston cylinder; and the gene detection kit further includes an end cover, the end cover is provided at one end of the kit body in the axial direction of the piston cylinder, and the end cover is configured to cover the openings.

In some embodiments, the end cover is provided thereon with a second avoidance hole; and the second avoidance hole is configured to allow the piston rod to pass through, so that the piston rod can extend into the piston cavity.

The present disclosure provides a gene detection device, configured to be used in association with the gene detection kit according to any one of the above, wherein the gene detection device includes:

a frame;

a positioning mechanism, wherein the positioning mechanism is mounted on the frame, and the positioning mechanism is configured to place and position the gene detection kit;

a driving mechanism, wherein the driving mechanism is mounted on the frame, and the driving mechanism is configured to drive the piston cylinder to move relative to the kit body, so that the plurality of second channels are alternately in communication with the first channel; and an executing mechanism, wherein the executing mechanism is mounted on the frame, and the executing mechanism is configured to drive the piston to move in the piston cavity along the axial direction of the piston cylinder, so as to realize reagent exchange between the piston cavity and the reagent cavities.

In some embodiments, the positioning mechanism includes a fixing seat and a positioning seat;

the fixing seat is fixedly mounted on the frame, and a second through hole through which the driving mechanism passes is provided on the fixing seat; and the positioning seat is movably provided on the fixing seat along a first direction, the positioning seat is configured to place and position the gene detection kit, the positioning seat has a placement position and an operation position in the first direction, wherein the first direction is perpendicular to the axial direction of the piston cylinder, and when the positioning seat is located in the placement position, the positioning seat is configured to allow taking and placing the gene detection kit, and when the positioning seat is located in the operation position, the driving mechanism can be connected to the piston cylinder.

In some embodiments, the positioning seat is provided with a positioning groove at one side facing away from the positioning seat in the axial direction of the piston cylinder, and the positioning groove is configured to be snapped with the gene detection kit along the first direction so as to position the gene detection kit on the positioning seat; and an avoidance groove is provided on a groove bottom wall of the positioning groove, and when the positioning seat moves to the operation position along the first direction, the avoidance groove is configured to be snapped with the driving mechanism, so that the driving mechanism can be connected to the piston cylinder.

In some embodiments, a groove side wall of the positioning groove has a first guide slope, and the first guide slope is configured to guide the gene detection kit into the positioning groove along the first direction.

In some embodiments, the positioning mechanism further includes a limiting component; and the limiting component is provided on the positioning seat, and the limiting component is configured to prevent the gene detection kit from exiting from the positioning groove along the first direction.

In some embodiments, the limiting component includes a limiting part;

the positioning seat is provided thereon with a third through hole, wherein the third through hole penetrates through two sides of the positioning seat along the axial direction of the piston cylinder, the limiting part is movably inserted into the third through hole along the axial direction of the piston cylinder, and two ends of the limiting part in the axial direction of the piston cylinder are respectively configured to extend out from two sides of the positioning seat; and the fixing seat is provided with, on a side facing the positioning seat in the axial direction of the piston cylinder, a second guide slope to be abutted by the limiting part, when the positioning seat moves from the placement position to the operation position along the first direction, the limiting part is configured to move along the axial direction of the piston cylinder relative to the positioning seat under guidance of the second guide slope, so that one end of the limiting part extends out from one side of the positioning seat facing away from the fixing seat in the axial direction of the piston cylinder, so that the limiting part can be abutted by the gene detection kit in the first direction.

In some embodiments, the limiting component further includes a roller;

the roller is mounted at one end of the limiting part close to the fixing seat in the axial direction of the piston cylinder, and the roller is configured to abut against the second guide slope.

In some embodiments, the fixing seat is provided thereon with a limiting stopper, and the limiting stopper is configured to be abutted by the positioning seat when the positioning seat moves to the operation position in the first direction.

In some embodiments, the gene detection device further includes a housing and a door;

the housing is configured to accommodate the frame, and a placement port is provided at a position of the housing corresponding to the positioning mechanism;

the door is movably provided on the housing, the door is configured to open or close the placement port, the door is in transmission connection with the positioning seat, and the door is configured to, when opening or closing the placement port, drive the positioning seat to move between the placement position and the operation position in the first direction.

In some embodiments, the door is rotatably connected to the fixing seat, and the door is configured to open or close the placement port when it is rotated relative to the fixing seat; and the door is provided thereon with a transmission member, two ends of the transmission member are respectively hinged to the door and the positioning seat, so that when the door is rotated relative to the housing, the positioning seat can be driven by the transmission member to move between the placement position and the operation position along the first direction.

In some embodiments, the driving mechanism includes a rotating shaft and a first driving assembly;

the rotating shaft is rotatably provided on the frame, the rotating shaft extends along the axial direction of the piston cylinder, and one end of the rotating shaft in the axial direction of the piston cylinder is configured to be detachably connected to the piston cylinder; and the first driving assembly is connected to the rotating shaft, and the first driving assembly is configured to drive the rotating shaft to rotate relative to the frame, so as to drive the piston cylinder to circumferentially rotate relative to the kit body.

In some embodiments, one end of the rotating shaft in the axial direction of the piston cylinder is provided with a butt-joint groove in which the operation portion of the piston cylinder is clamped.

In some embodiments, the rotating shaft is of a hollow structure with two open ends, the rotating shaft is configured to be inserted by the magnetic member, and the magnetic member is configured to adsorb the magnetic beads in the piston cavity.

In some embodiments, the driving mechanism further includes a detection assembly; and the detection assembly is configured to detect an angle of rotation of the rotating shaft relative to the frame.

In some embodiments, the executing mechanism includes a piston rod and a second driving assembly;

the piston rod is movably provided on the frame along the axial direction of the piston cylinder, at least a part of the piston rod is configured to extend into the piston cavity, the end of the piston rod extending into the piston cavity has an execution end, and the execution end is configured to be connected to the piston; and the second driving assembly is connected to the piston rod, and the second driving assembly is configured to drive the piston rod to move relative to the frame along the axial direction of the piston cylinder, so as to drive the piston to move along the axial direction of the piston cylinder in the piston cavity.

In some embodiments, one end of the piston in the axial direction of the piston cylinder is provided with a clamping groove, and the clamping groove is configured to be snapped with the execution end.

In some embodiments, the piston rod has a first position and a second position in the axial direction of the piston cylinder;

when the piston rod is located at the first position, the execution end of the piston rod can be clamped in the clamping groove of the piston, and when the piston rod is located at the second position, the execution end of the piston rod can exit from the clamping groove of the piston; and the second driving assembly is configured to drive the piston rod to move between the first position and the second position along the axial direction of the piston cylinder.

In some embodiments, the executing mechanism further includes two limiting sensors; and the two limiting sensors are arranged at intervals on the frame along the axial direction of the piston cylinder, and the two limiting sensors are respectively configured to limit the first position and the second position of the piston rod in the axial direction of the piston cylinder.

BRIEF DESCRIPTION OF DRAWINGS

In order to more clearly illustrate technical solutions of embodiments of the present disclosure, accompanying drawings which need to be used in the embodiments will be introduced briefly below. It should be understood that the accompanying drawings below merely show some embodiments of the present disclosure, and therefore should not be considered as limitation to the scope. Those ordinarily skilled in the art still could obtain other relevant drawings according to these accompanying drawings, without using creative efforts.

Figure 1:
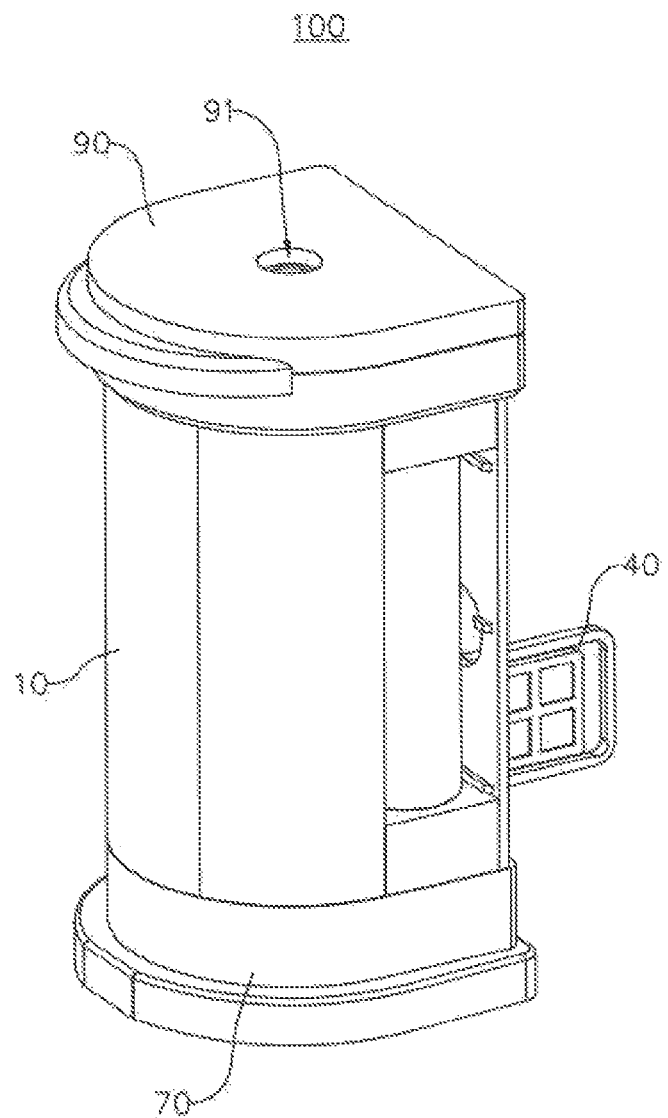
FIG. 1 is a structural schematic view of a gene detection kit provided in some embodiments of the present disclosure.

Reference signs: 100—gene detection kit; 10—kit body; 11—accommodating cavity; 12—reagent cavity; 121—lysing cavity; 122—washing cavity; 123—elution cavity; 124—product output cavity; 13—second channel; 14—limiting groove; 15—opening; 16—third channel; 161—first hole section; 162—second hole section; 17—mounting groove; 18—clamping rib; 20—piston cylinder; 21—piston cavity; 211—first receptacle; 212—magnetic bead retention tank; 22—first channel; 23—limiting protrusion; 24—strip-shaped groove; 25—second sealing member; 26—cylinder body; 27—partition wall; 28—magnetic cavity; 281—second receptacle; 29—operation portion; 291—clamping surface; 30—piston; 31—clamping groove; 40—amplification reaction tube; 41—inlet; 42—outlet; 43—amplification reaction cavity; 50—sealing pad; 60—first sealing member; 61—first through-hole; 70—base; 71—accommodating groove; 72—first avoidance hole; 73—skirt; 74—clamping member; 741—clamping groove; 75—insertion slot;

76—positioning hole; 80—locking member; 81—wedge-shaped notch; 82—positioning boss; 83—locking portion; 84—hand-held portion; 841—anti-slip stripe; 842—label attaching area; 90—end cover; 91—second avoidance hole; 92—seat body; 921—first pore; 922—second pore; 923—reinforcing rib; 93—cover body; 94—third sealing member; 1000—gene detection device; 200—frame; 201—mounting table; 300—positioning mechanism; 301—fixing seat; 3011—second through hole; 3012—first slide rail; 3013—limiting stopper; 3014—in-place detection part; 3015—second guide slope; 302—positioning seat; 3021—positioning groove; 3022—avoidance groove; 3023—positioning seat body; 3024—positioning block; 3025—first guide slope; 3026—clamping groove; 3027—third through hole; 3028—limiting block; 303—limiting component; 3031—limiting part; 3031a—abutment portion; 3032—roller; 400—driving mechanism; 401—rotating shaft; 4011—butt-joint groove; 4012—fourth through hole; 402—first driving assembly; 4021—first driving member; 4022—first transmission unit; 403—mounting plate; 404—magnetic member driving device; 405—detection assembly; 500—executing mechanism; 501—piston rod; 5011—execution end; 502—second driving assembly; 5021—second driving member; 5022—second transmission unit; 503—mounting seat; 5031—second slide rail; 504—moving seat; 5041—second slider; 505—limiting sensor; 600—housing; 601—placement port; 700—door; 701—transmission member; 800—heating mechanism; X—first direction; Y—second direction; Z—third direction.

DETAILED DESCRIPTION OF EMBODIMENTS

In order to make objectives, technical solutions, and advantages of the embodiments of the present disclosure clearer, the technical solutions in the embodiments of the present disclosure will be described clearly below in conjunction with the accompanying drawings in the embodiments of the present disclosure. Apparently, some but not all embodiments of the present disclosure are described. Based on the embodiments of the present disclosure, all of other embodiments obtained by those ordinarily skilled in the art without using creative efforts shall fall within the scope of protection of the present disclosure.

Unless otherwise defined, all technical and scientific terms used in the present disclosure have the same meanings as those commonly understood by those skilled in the art to which the present disclosure belongs; the terms used in the description of the present disclosure are merely for the purpose of describing specific embodiments, but are not intended to limit the present disclosure; and the terms "comprising" and "having" and any variations thereof in the description and the claims of the present disclosure as well as the foregoing description of the accompanying drawings are intended to cover non-exclusive inclusions. The terms "first", "second" and the like in the description and the claims or the above accompanying drawings of the present disclosure are used to distinguish different objects, rather than to describe a specific order or a primary-secondary relationship.

The phrase "embodiment" referred to in the present disclosure means that the specific features, structures, and characteristics described in combination with the embodiment may be included in at least one embodiment of the present disclosure. The phrase appearing at various locations in the description does not necessarily refer to the same embodiment, or an independent or alternative embodiment exclusive of another embodiment.

In the description of the present disclosure, it should be noted that unless otherwise explicitly specified and defined, the terms "mount", "join", "connect", and "attach" should be understood in a broad sense, for example, it may be a fixed connection, a detachable connection, or an integrated connection; it may be a direct connection or an indirect connection via an intermediary, or inner communication between two elements. For those ordinarily skilled in the art, specific meanings of the above-mentioned terms in the present disclosure could be understood according to specific circumstances.

The term "and/or" in the present disclosure is merely an association relationship describing associated objects, and indicates that there may be three relationships, for example, A and/or B may indicate that A exists alone, both A and B exist, and B exists alone. In addition, the character "l" in the present disclosure generally indicates that the associated objects before and after the character are in an "or" relation.

In the embodiments of the present disclosure, same components are denoted by same reference signs, and for the sake of brevity, detailed illustration of the same components is omitted in different embodiments. It should be understood that dimensions such as thicknesses and lengths of various components in the embodiments of the present disclosure shown in the accompanying drawings, as well as dimensions such as overall thickness and length of an integrated apparatus are merely exemplary illustration, and should not constitute any limitation to the present disclosure.

The term "a plurality of" appearing in the present disclosure means two or more (including two).

At present, gene detection is a medical detection technology. By extracting nucleic acids in peripheral venous blood, tissues, and other body fluids of a subject, and analyzing information about DNA molecules or RNA molecules in cells of the subject by a detection device, gene information about the subject is known, and further a cause or a risk of disease is determined. Nucleic acid extraction is a pretreatment process of the gene detection. Specific primer and probe designs are performed according to a sequence of a known nucleic acid, the designed primer is synthesized, a fluorescence quantitative PCR experiment is performed by using the extracted nucleic acid as a template, and whether a target sample is positive or negative is judged according to a fluorescence signal. The nucleic acid extraction is a key step in the gene detection, and the nucleic acid quality obtained therefrom directly affects the success of downstream experiment. It should be understood that the gene detection is not limited to detection on human bodies, but also includes gene detection on animals and plants.

As relatively accurate detection means, the gene detection is mainly applied in aspects such as disease detection and substance analysis. It is now known that human diseases are all directly or indirectly related to genes, and detection and analysis of genes are increasingly used widely in fields such as genetic diseases, tumors, and infectious diseases, thereby the disease diagnosis modes and treatment strategies are updated, and the pathogenesis of diseases related to gene structure or expression abnormalities can be revealed, thus, the gene detection has been widely applied in fields such as biomedicine. In practical use, a main process of the gene detection includes sample acquisition, nucleic acid extraction of the sample (sample lysing, washing, drying, elution, and PCR amplification (performing polymerase chain reaction for the nucleic acid), etc.), and gene detection, so as to realize the gene detection on the sample.

In the above, an extraction process of nucleic acid is as follows: firstly, a sample is subjected to lysis with a lysate, then nucleic acid in the sample is adsorbed by magnetic beads, after that the magnetic beads are washed by a washing solution, so as to rinse the lysate remaining on the magnetic beads, then the nucleic acid on the magnetic beads is dissolved by an eluent, and finally the nucleic acid in the eluent is amplified through PCR amplification, thus completing the nucleic acid extraction work of the sample.

The inventors found that in the conventional gene detection process, the multiple steps of nucleic acid extraction need to be operated on different instruments, then the sample or reagent needs to be transferred multiple times, thus increasing the possibility of cross-contamination of samples, and further leading to an inaccurate gene detection result, and bringing quite serious harm to patients. In order to solve the problem of inaccurate gene detection result caused by cross-contamination of samples or reagents, a sample reaction device is designed in the prior art, wherein the sample reaction device has a piston cylinder and a plurality of reagent cavities, then, by providing reagent channels in a switching valve, and rotating the switching valve, communication between different reagent cavities and a piston cavity of the piston cylinder is realized, so as to extract a sample, thus automated and centralized extraction is performed on the whole process of nucleic acid extraction with the specially designed sample reaction means and device in a fully enclosed gene detection mode, so as to mitigate cross-contamination problem between samples. However, for reagent channels of the switching valve of such a sample reaction device, there are multi-angle non-linear channels, thus the sample reaction device is relatively difficult to process, resulting in relatively high manufacturing costs, further greatly increasing the costs of gene detection. Moreover, the sample reaction device of such a structure has the risk of liquid leakage and blockage of the reagent channels, thus causing a relatively large potential safety hazard during the gene detection process.

Based on the above consideration, in order to solve the problem that the costs of gene detection are relatively high and there is a relatively large potential safety hazard in the process of gene detection, after intensive research, the inventors provide, in some embodiments of the present disclosure, a gene detection kit. The gene detection kit is provided with a kit body, a piston cylinder, and a piston, wherein the kit body is provided thereon with an accommodating cavity configured to accommodate the piston cylinder and a plurality of reagent cavities configured to accommodate a reagent or a sample, the piston cylinder is movably provided in the accommodating cavity, and the piston is movably provided in the piston cavity of the piston cylinder along an axial direction of the piston cylinder. In the above, a first channel in communication with the piston cavity is provided on an outer circumferential surface of the piston cylinder, a plurality of second channels are provided on an inner wall of the accommodating cavity, each second channel is in communication with one reagent cavity, so that the first channel can be in communication with one second channel of the plurality of second channels when the piston cylinder is moved relative to the kit body.

By using the gene detection kit of such a structure, a plurality of steps of nucleic acid extraction for a sample can be completed in an enclosed space, so that the sample is extracted in a centralized manner, without the need of multiple external transfers of the sample, thus the risk of cross-contamination of the samples during the external transfer can be effectively reduced, and further it is beneficial to improve the accuracy of a gene detection result, so as to reduce harm to the patients caused by low accuracy of the gene detection result.

In addition, by providing the first channel in communication with the piston cavity on the outer circumferential surface of the piston cylinder, and providing the plurality of second channels in communication with respective reagent cavities on the inner wall of the accommodating cavity, the communication between the first channel on the outer circumferential surface of the piston cylinder and the second channels on the inner wall of the accommodating cavity can be realized just by making the piston cylinder move relative to the kit body, so that the communication between the piston cavity and one reagent cavity of the plurality of reagent cavities is realized, thus by using the gene detection kit of such a structure, on the one hand, there is no need to provide other components such as a switching valve or a converting valve to realize the communication between the first channel and the second channels, which is beneficial to reduce the manufacturing costs of the gene detection kit, and the first channel can be in direct communication with the second channels, thus reducing a flow distance of the sample or reagent exchanged between the piston cavity and the reagent cavities, and reducing butt-joint ports between the piston cavity and the reagent cavities, further being capable of effectively reducing the risk of liquid leakage of the gene detection kit; and on the other hand, as the first channel is provided on the outer circumferential surface of the piston cylinder and the second channels are provided on the inner wall of the accommodating cavity of the kit body, it is convenient to process the first channel and the second channels on the piston cylinder and the kit body, which is beneficial to reduce the difficulty of the manufacturing process of the first channel and the second channels, and further can effectively reduce the processing costs.

In the above technical solution, the kit body is provided with the accommodating cavity and the plurality of reagent cavities, and the piston cylinder is movably inserted into the accommodating cavity, thus, by providing the first channel in communication with the piston cavity of the piston cylinder on the outer circumferential surface of the piston cylinder, and providing the plurality of second channels in communication with respective reagent cavities on the inner wall of the accommodating cavity, when the piston cylinder is moved relative to the kit body in the accommodating cavity, the first channel can be selectively in communication with one second channel of the plurality of second channels, further the piston cavity of the piston cylinder is enabled to be in communication with different reagent cavities, so that when the piston is moved in the piston cavity of the piston cylinder, sample extraction and exchange and transfer in different reagent cavities can be realized. By using the gene detection kit of such a structure, a plurality of steps of nucleic acid extraction for a sample can be completed in an enclosed space, so that the sample is extracted in a centralized manner, without the need of multiple external transfers of the sample, thus the risk of cross-contamination of the samples during the external transfer can be effectively reduced, and further it is beneficial to improve the accuracy of a gene detection result, so as to reduce harm to the patients caused by low accuracy of the gene detection result. In addition, by providing the first channel in communication with the piston cavity on the outer circumferential surface of the piston cylinder, and providing the plurality of second channels in communication with respective reagent cavities on the inner wall of the accommodating cavity, the commu- nication between the first channel on the outer circumferential surface of the piston cylinder and the second channels on the inner wall of the accommodating cavity can be realized just by making the piston cylinder move relative to the kit body, so that the communication between the piston cavity and one reagent cavity of the plurality of reagent cavities is realized, thus by using the gene detection kit of such a structure, on the one hand, there is no need to provide other components such as a switching valve or a converting valve to realize the communication between the first channel and the second channels, which is beneficial to reduce the manufacturing costs of the gene detection kit, and the first channel can be in direct communication with the second channels, thus reducing a flow distance of the sample or reagent exchanged between the piston cavity and the reagent cavities, and reducing butt-joint ports between the piston cavity and the reagent cavities, further being capable of effectively reducing the risk of liquid leakage of the gene detection kit; and on the other hand, as the first channel is provided on the outer circumferential surface of the piston cylinder and the second channels are provided on the inner wall of the accommodating cavity of the kit body, it is convenient to process the first channel and the second channels on the piston cylinder and the kit body, which is beneficial to reduce the difficulty of the manufacturing process of the first channel and the second channels, and further can effectively reduce the processing costs.

In addition, the gene detection kit provided in an embodiment of the present disclosure further has the following additional technical features:

in some embodiments, the first channel is in communication with a bottom of the piston cavity.

In some embodiments, a side wall of the piston cylinder is provided thereon with a first channel in communication with the piston cylinder, and correspondingly, a side wall of the accommodating cavity is provided thereon with a plurality of second channels in communication with respective cavities.

In some embodiments, the gene detection kit includes a hollow kit body, a channel in the center of the kit body is provided therein with a piston cylinder, the piston cylinder is rotatably connected to the channel, the piston cylinder is provided therein with a piston cavity configured to mount a piston, a plurality of cavities are provided inside the kit body around the piston cylinder, a side wall of the piston cylinder is provided thereon with a first channel in communication with a bottom of the piston cavity, and correspondingly, an inner side wall of the kit body is provided thereon with a plurality of second channels in communication with respective reagent cavities. When the piston cylinder is rotated to a state that the first channel is in communication with one of the second channels, the piston cavity is in communication with the cavity corresponding to this second channel, and the remaining second channels are blocked by the side wall of the piston cylinder.

In some embodiments, the kit body may be of a hollow annular cylinder structure.

In some embodiments, the channel may include an accommodating cavity. In some embodiments, the piston cylinder is rotatably connected to the accommodating cavity.

In some embodiments, the cavities include a solvent cavity. In some embodiments, the cavities include a lysing cavity, a washing cavity, an elution cavity, and a product output cavity, wherein the lysing cavity, the washing cavity, and the elution cavity each have a feeding port, and each feeding port is correspondingly provided with a sealing cover. Before use, the lysing cavity, the washing cavity, and the elution cavity are respectively pre-filled with a lysate, a washing solution, and an eluent.

In some embodiments, the channel may include, but is not limited to, a microfluidic flow channel.

In some embodiments, the lysing cavity is configured to mix an added sample with the lysate in the lysing cavity for lysis of the sample.

In some embodiments, when the first channel is in communication with any one of the second channels, the remaining second channels are blocked by the outer circumferential surface of the piston cylinder.

In the above technical solution, the second channels provided on the inner wall of the accommodating cavity also can be blocked by the outer circumferential surface of the piston cylinder, so that in the process of movement of the piston cylinder relative to the kit body, not only the communication between the first channel and one second channel of the plurality of second channels can be realized, but also the blocking function for the remaining second channels can be realized, thus it is unnecessary to provide other components to block the second channels that are not in communication with the first channel. Thus, the gene detection kit of such a structure is easy to operate, beneficial to reduce the operation difficulty of the gene detection kit, and conducive to reduce the manufacturing costs of the gene detection kit.

In some embodiments, the gene detection kit further includes a first sealing member; and the first sealing member is sleeved on the outer circumferential surface of the piston cylinder. The first sealing member is provided with a first through hole in communication with the first channel at a position corresponding to the first channel. In the above technical solution, by sleeving the first sealing member at the position corresponding to the first channel on the outer circumferential surface of the piston cylinder, on the one hand, the first sealing member is enabled to seal a gap at a joint between the first channel and the second channel when the first channel of the piston cylinder is in communication with the second channel of the kit body, so that the risk of liquid leakage at the joint between the first channel and the second channel can be further reduced; and on the other hand, for the second channels which are not in communication with the first channel, the first sealing member also can improve the blocking effect for this part of second channels, that is to say, when the first channel is in communication with any one of the second channels, the first sealing member sleeved on the piston cylinder is located between the outer circumferential surface of the piston cylinder and this part of second channels, thus the blocking effect of the outer circumferential surface of the piston cylinder on this part of second channels can be improved, further being beneficial to further reduce the risk of liquid leakage of the gene detection kit. In some embodiments, the outer circumferential surface of the piston cylinder is provided thereon with the first annular groove extending along a circumferential direction of the piston cylinder; and the first annular groove is configured to accommodate the first sealing member, and the first channel is provided on a groove bottom wall of the first annular groove. In the above technical solution, by providing the first annular groove on the outer circumferential surface of the piston cylinder to mount the first sealing member in the first annular groove, the phenomenon of axial movement of the first sealing member relative to the piston cylinder along the axial direction of the piston cylinder can be effectively reduced, so as to improve the mounting stability of the first sealing member, and further facilitate improving the sealing effect of the first sealing member.

In some embodiments, a side wall of the piston cylinder is provided thereon with a first annular groove surrounding the second channels, the first annular groove is provided with the first sealing member, and a surface of the first sealing member is abutted against the piston cylinder.

In some embodiments, the sealing member includes, but is not limited to, a sealing ring.

In some embodiments, in the axial direction of the piston cylinder, one end of the piston cylinder is provided with a first receptacle into which a piston rod is inserted, the first receptacle is provided opposite to a bottom surface of the piston cavity, the bottom surface of the piston cavity gradually gets away from the first receptacle from an edge to a center, and the first channel is connected to the center of the bottom surface of the piston cavity. In other words, the first receptacle includes a proximal end and a distal end, and in the axial direction of the piston cylinder, the bottom surface of the piston cavity gradually approaches the proximal end of the first receptacle from the edge to the center.

In the above technical solution, by providing the first receptacle at one end of the piston cylinder, the piston rod can extend into the piston cavity through the first receptacle, so that the piston rod can drive the piston to move in the piston cavity, so as to realize reagent exchange between the piston cavity and the reagent cavity. In addition, by providing the bottom surface of the piston cavity in a structure gradually getting away from the first receptacle from the edge to the center, and making the first channel penetrate through a central position of the bottom surface of the piston cavity, that is to say, making the bottom surface of the piston cavity in a structure recessed away from the first receptacle from the edge to the center, and providing the first channel at the lowest point of the bottom surface of the piston cavity, it is convenient to discharge the reagent in the piston cavity from the piston cavity through the first channel, it is beneficial to reduce the phenomenon that the reagent remains in the piston cavity, and further the waste of the reagent can be effectively reduced.

In some embodiments, a magnetic bead retention tank configured to accommodate magnetic beads is provided on the bottom surface of the piston cavity; and in the axial direction of the piston cylinder, the magnetic bead retention tank is closer to the first receptacle than the center of the bottom surface of the piston cavity.

In the above technical solution, by providing the magnetic bead retention tank on the bottom surface of the piston cavity, and making the magnetic bead retention tank closer to the first receptacle than the center of the bottom surface of the piston cavity in the axial direction of the piston cylinder, that is to say, there is a distance between the magnetic bead retention tank and the center of the bottom surface of the piston cavity in the axial direction of the piston cylinder, that is, there is a distance between the magnetic bead retention tank and the first channel in the axial direction of the piston cylinder, the magnetic beads can be retained in the magnetic bead retention tank on the bottom surface of the piston cavity under the accommodating effect of the magnetic bead retention tank on the magnetic beads, so as to reduce the risk that the magnetic beads are discharged with the reagent from the first channel, and the risk that the magnetic beads block the first channel can be effectively reduced. In some embodiments, a magnetic bead retention tank configured to accommodate the magnetic beads is provided on an inclined bottom surface of the piston cavity, and a position of the magnetic bead retention tank is lower than the lowest position where the piston can reach.

In some embodiments, the piston cylinder includes a cylinder body and a partition wall; the partition wall is provided in the cylinder body and divides an inner space of the cylinder body into the piston cavity and a magnetic cavity, wherein the piston cavity and the magnetic cavity are arranged along an axial direction of the cylinder body, the cylinder body has a first receptacle and a second receptacle at two ends in the axial direction thereof, the first receptacle is configured to allow the piston rod to be inserted into the piston cavity, the second receptacle is configured to allow a magnetic member to be inserted into the magnetic cavity, and the magnetic member is configured to adsorb the magnetic beads.

In the above technical solution, the piston cylinder has the cylinder body and the partition wall, and the inner space of the cylinder body can be divided by the partition wall into the piston cavity for extracting the sample and the magnetic cavity into which the magnetic member is inserted, so that the magnetic member, after being inserted into the magnetic cavity, can adsorb the magnetic beads accommodated in the piston cavity, thus the piston cavity of such a structure can shorten a distance between the magnetic member and the piston cavity in the axial direction of the piston cylinder, so as to improve the magnetic effect of the magnetic member to the magnetic beads, further being beneficial to enhance the stability of magnetic beads being adsorbed on the bottom surface of the piston cavity.

In some embodiments, the plurality of reagent cavities are arranged along the circumferential direction of the piston cylinder.

In the above technical solution, by providing the plurality of reagent cavities along the circumferential direction of the piston cylinder, that is to say, arranging the plurality of reagent cavities around the accommodating cavity, it is convenient to provide the second channels in communication with the reagent cavities on the inner wall of the accommodating cavity, so that the communication between the second channels and the reagent cavities can be realized just by providing linear second channels on the inner wall of the accommodating cavity. Thus, by using the gene detection kit of such a structure, on the one hand, it is beneficial to reduce the length of the second channels, so as to reduce the flow distance of the reagent or the sample in the second channels, and on the other hand, it is beneficial to reduce the difficulty of the manufacturing process of the first channel, so as to reduce the processing costs, and the linear second channels are beneficial to reduce the risk of jamming of the second channels.

In some embodiments, each of the reagent cavities has an opening at one end in the axial direction of the piston cylinder; the plurality of reagent cavities include a lysing cavity, a washing cavity, an elution cavity, and a product output cavity. In the axial direction of the piston cylinder, bottom surfaces of the lysing cavity, the washing cavity, and the elution cavity are provided opposite to respective openings, and the bottom surfaces of the lysing cavity, the washing cavity, and the elution cavity are all inclined surfaces, and are gradually away from respective openings from a side away from the piston cylinder to a side close to the piston cylinder, and the second channels are connected to a side of the inclined surface close to the piston cylinder.

In the above technical solution, by providing the lysing cavity, the washing cavity, the elution cavity, and the product output cavity on the kit body, after the sample is extracted through lysing, washing, and elution, it is convenient to place the extracted sample in the product output cavity, thus completing the extraction of the nucleic acid of the sample, so as to realize the centralized extraction of the nucleic acid of the sample. In addition, as the bottom surfaces of the lysing cavity, the washing cavity, and the elution cavity are all provided as inclined surfaces which are gradually away from respective openings from the side away from the piston cylinder to the side close to the piston cylinder, and the second channels penetrate through a side of the inclined surfaces close to the piston cylinder, that is to say, the bottom surfaces of the lysing cavity, the washing cavity, and the elution cavity are all of structures recessed away from the respective openings in the axial direction of the piston cylinder, and the second channels penetrate through the lowest point of the inclined surfaces, it is convenient to discharge the reagents in the lysing cavity, the washing cavity, and the elution cavity through the second channels, it is beneficial to reduce the phenomenon of residual reagents in the lysing cavity, the washing cavity, and the elution cavity, and further the waste of the reagents can be effectively reduced.

In some embodiments, the plurality of reagent cavities further include a magnetic bead cavity; and the lysing cavity, the magnetic bead cavity, the washing cavity, the elution cavity, and the product output cavity are sequentially arranged along the circumferential direction of the piston cylinder.

In the above technical solution, by providing the magnetic bead cavity on the kit body so as to accommodate the magnetic beads, later operation and use are facilitated, and by arranging the lysing cavity, the magnetic bead cavity, the washing cavity, the elution cavity, and the product output cavity sequentially along the circumferential direction of the piston cylinder, the piston cavity of the piston cylinder can be allowed to be in communication with the lysing cavity, the magnetic bead cavity, the washing cavity, the elution cavity, and the product output cavity in sequence, so that the order of communication between the piston cavity and respective reagent cavities is the same as the order of performing the nucleic acid extraction on the sample, further facilitating the operation and saving the operation time, and being beneficial to improve the extraction efficiency of the nucleic acid.

In some embodiments, the magnetic bead cavity has a feeding port, and before use, the magnetic bead cavity is pre-filled with magnetic beads configured to adsorb the nucleic acid.

In some embodiments, the plurality of reagent cavities further include a drying cavity; and the lysing cavity, the washing cavity, the drying cavity, the elution cavity, and the product output cavity are sequentially arranged along the circumferential direction of the piston cylinder.

In the above technical solution, by providing the drying cavity on the kit body, it is convenient to dry the magnetic beads, thus it is beneficial to reduce the contamination to the eluent caused by the washing solution remaining on the magnetic beads, moreover, by arranging the lysing cavity, the washing cavity, the drying cavity, the elution cavity, and the product output cavity sequentially along the circumferential direction of the piston cylinder, the piston cavity of the piston cylinder can be in communication with the lysing cavity, the washing cavity, the drying cavity, the elution cavity, and the product output cavity in sequence, so that the order of communication between the piston cavity and respective reagent cavities is the same as the order of performing nucleic acid extraction on the sample, further facilitating the operation and saving the operation time, and being beneficial to improve the extraction efficiency of the nucleic acid.

In some embodiments, the gene detection kit further includes an amplification reaction tube; and the amplification reaction tube is connected to the kit body, the product output cavity is in communication with a corresponding second channel through the amplification reaction tube, and the amplification reaction tube is configured to amplify the nucleic acid.

In the above technical solution, by providing the amplification reaction tube configured to amplify the nucleic acid on the kit body and making the product output cavity be in communication with the second channel through the amplification reaction tube, the reagent in the piston cavity can enter the amplification reaction tube through the first channel and the second channel, and can enter the product output cavity after nucleic acid amplification in the amplification reaction tube is completed, facilitating the subsequent gene detection. Thus, by using the gene detection kit of such a structure, the centralized extraction work of the nucleic acid can be completed in an enclosed space, so as to reduce the risk of contamination of the sample during the process of nucleic acid extraction, and facilitate the optimization of the tedious process of nucleic acid extraction.

In some embodiments, the kit body further has a third channel in communication with the product output cavity; the amplification reaction tube has an inlet and an outlet, wherein the inlet is in communication with the second channel corresponding to the product output cavity, and the outlet is in communication with the third channel.

In the above technical solution, by providing the third channel in communication with the product output cavity on the kit body, after the inlet and the outlet of the amplification reaction tube are respectively in communication with the second channel and the third channel, the communication between the product output cavity and the second channel can be realized, with a simple structure and easy implementation.

In some embodiments, the piston cylinder can be circumferentially rotated relative to the kit body, such that the plurality of second channels are alternately in communication with the first channel.

In the above technical solution, by inserting the piston cylinder in the accommodating cavity of the kit body in a circumferentially rotatable manner, the communication between the first channel and one second channel of the plurality of second channels can be realized just by making the piston cylinder circumferentially rotate relative to the kit body. The gene detection kit of such a structure is easy to operate and has relatively high structural stability.

In some embodiments, the outer circumferential surface of the piston cylinder is provided with a limiting protrusion in a protruding way; and a limiting groove is provided on the inner wall of the accommodating cavity, and the limiting groove is configured to be snapped with the limiting protrusion, so as to restrict the axial movement of the piston cylinder relative to the kit body.

In the above technical solution, by providing the limiting protrusion on the piston cylinder, and providing, on the inner wall of the accommodating cavity, the limiting groove in which the limiting protrusion is clamped, a limiting function for the piston cylinder can be realized with this structure, so as to reduce the phenomenon of axial movement of the piston cylinder relative to the kit body, further the risk that the first channel of the piston cylinder and the second channels of the kit body are misaligned in the axial direction of the piston cylinder can be effectively reduce, which, on the one hand, is beneficial to ensure the smooth operation of the gene detection kit, and on the other hand, is beneficial to reduce the risk of liquid leakage caused by the misalignment of the first channel and the second channels.

In some embodiments, the limiting protrusion and the limiting groove are both of annular structures extending along the circumferential direction of the piston cylinder.

In the above technical solution, by providing both the limiting protrusion and the limiting groove to be of annular structures extending along the circumferential direction of the piston cylinder, the structural strength of the limiting protrusion can be improved, further it is beneficial to improve the stability of limiting the piston cylinder by the limiting protrusion and the limiting groove.

In some embodiments, the accommodating cavity penetrates through the kit body along the axial direction of the piston cylinder; one end of the piston cylinder has the first receptacle into which the piston rod is inserted, one end of the piston cylinder, far away from the first receptacle in the axial direction thereof, extends out from the kit body and has an operation portion, wherein the operation portion is configured to be connected to a driving mechanism so as to drive the piston cylinder to circumferentially rotate relative to the kit body. In other words, the piston cylinder extends out from the kit body at the proximal end of the first receptacle in the axial direction thereof and has the operation portion.

In the above technical solution, by making one end of the piston cylinder away from the first receptacle in the axial direction thereof extend out from the kit body and forming the operation portion, it is convenient to connect the operation portion to the driving mechanism, thus, the driving mechanism can drive the piston cylinder to circumferentially rotate relative to the kit body through the operation portion, so as to realize the communication between the first channel of the piston cylinder and one second channel of the plurality of second channels of the kit body. The gene detection kit of such a structure is convenient to operate, and can realize the automated extraction of the gene detection kit, so as to improve the nucleic acid extraction efficiency of the sample.

In some embodiments, the gene detection kit further includes the base; the base is provided with an accommodating groove, one end of the kit body close to the operation portion in the axial direction of the piston cylinder is inserted into the accommodating groove, a first avoidance hole is provided in a groove bottom wall of the accommodating groove, and the first avoidance hole is configured to allow one end of the piston cylinder away from the first receptacle to extend out. In other words, the first avoidance hole is configured to allow the piston cylinder to extend out at the proximal end of the first receptacle. In some embodiments, the accommodating groove is configured to accommodate the bottom of the kit body.

In the above technical solution, by providing the accommodating groove into which the kit body is inserted on the base so that the kit body is mounted on the base, the connection between the kit body and the base is realized, thus being beneficial to realize the disassembly and mounting of the kit body and the base. In addition, the groove bottom wall of the accommodating groove is provided thereon with the first avoidance hole through which the operation portion of the piston cylinder passes, so that the operation portion can be connected to the driving mechanism after passing through the base.

In some embodiments, the gene detection kit further includes the locking member; and the locking member is mounted on the base, and the locking member is configured to be connected to the operation portion so as to prevent the piston cylinder from circumferentially rotating relative to the kit body.

In the above technical solution, the gene detection kit is further provided with a locking member, and after the locking member is connected to the operation portion of the piston cylinder, the piston cylinder can be locked, so as to prevent the piston cylinder from circumferentially rotating relative to the kit body, thus the piston cylinder can be held at a preset position, and further in the process of transporting or carrying the gene detection kit, the phenomenon that the piston cylinder is rotated circumferentially relative to the kit body can be reduced, so as to reduce the risk of liquid leakage or mutual contamination of the pre-filled reagents in the reagent cavities.

In some embodiments, the base and the operation portion are connected and fixed by snap-fitting.

In some embodiments, the outer circumferential surface of the base is provided with an insertion slot into which the locking member is inserted along the radial direction of the piston cylinder; the operation portion is wedge-shaped, the locking member is provided with a wedge-shaped notch, and when the locking member is inserted into the insertion slot, the wedge-shaped notch is snapped with the operation portion, so as to prevent the piston cylinder from circumferentially rotating relative to the kit body. In the above technical solution, by providing the operation portion of the piston cylinder to be wedge-shaped, and providing the wedge-shaped notch matched with the operation portion on the locking member, after the locking member is inserted into the insertion slot of the base, the operation portion can be clamped in the wedge-shaped notch of the locking member, so as to realize the locking function for the operation portion. By using the gene detection kit of such a structure, it only needs to insert the locking member into the insertion slot during transportation or carrying, and on the contrary, when it is necessary to work on the gene detection kit, it only needs to pull out the locking member from the insertion slot, with a simple structure, easy operation, and high stability.

In some embodiments, the base is provided with a positioning hole; the locking member is provided with a positioning boss, and when the locking member is inserted into the insertion slot, the positioning boss cooperates with the positioning hole to prevent the locking member from being detached from the insertion slot.

In the above technical solution, by providing the positioning hole on the base, and correspondingly providing the positioning boss on the locking member, after the locking member is inserted into the insertion slot, the positioning boss can be inserted into the positioning hole, then on the one hand, the positioning between the locking member and the base can be realized, so as to be beneficial to ensure that the locking member is inserted in place, to improve the insertion accuracy of the locking member, and on the other hand, by means of this structure, the locking member can be prevented from being detached from the insertion slot, thus, in the process of transporting or carrying the gene detection kit, it is beneficial to improve the reliability of locking the piston cylinder by the locking member.

In some embodiments, the locking member includes a locking portion and a hand-held portion; the locking portion has the wedge-shaped notch, the locking portion is configured to be inserted into the insertion slot so as to lock the operation portion; and the hand-held portion extends out from the outer circumferential surface of the base, and a plurality of anti-slip stripes are provided on the hand-held portion.

In the above technical solution, the locking member has a hand-held portion, and the hand-held portion extends out from the outer circumferential surface of the base. That is to say, when the locking member is inserted into the insertion slot, the hand-held portion of the locking member extends out of the outer circumferential surface of the base along the radial direction of the piston cylinder from the inside of the insertion slot, so that an operator can hold the locking member, so as to facilitate the insertion and pull-out of the locking member. In addition, by providing the plurality of anti-slip stripes on the hand-held portion, the anti-slip performance of the locking member can be effectively improved when the operator pulls out or and inserts the locking member, thus being beneficial to operate the locking member by the operator.

In some embodiments, each reagent cavity has an opening at one end in the axial direction of the piston cylinder; and the gene detection kit further includes an end cover, wherein the end cover is provided at one end of the kit body in the axial direction of the piston cylinder, and the end cover is configured to cover the openings.

In the above technical solution, the gene detection kit is further provided with an end cover, and by providing the end cover at one end of the kit body to cover the openings of the reagent cavities, it is beneficial to improve the sealing property of the reagent cavities, then the risk of volatilization or contamination of reagents in the reagent cavities is reduced, and further the accuracy of gene detection can be effectively improved.

In some embodiments, the end cover is provided thereon with a second avoidance hole; and the second avoidance hole is configured to allow the piston rod to pass through, so that the piston rod can extend into the piston cavity.

In the above technical solution, by providing the second avoidance hole on the end cover, the piston rod can be inserted into the piston cavity after passing through the end cover, so that the piston can be driven by the piston rod to move in the piston cavity without opening the end cover, further helping to ensure that the nucleic acid extraction process of the sample is performed in an enclosed space, so as to reduce the possibility of contamination of the sample.

Some embodiments of the present disclosure further provide a gene detection device, configured to be used in association with the above gene detection kit. The gene detection device includes a frame, a positioning mechanism, a driving mechanism, and an executing mechanism; the positioning mechanism is mounted on the frame, and the positioning mechanism is configured to place and position the gene detection kit; the driving mechanism is mounted on the frame, and the driving mechanism is configured to drive the piston cylinder to move relative to the kit body, so that the plurality of second channels are alternately in communication with the first channel; the executing mechanism is mounted on the frame, and the executing mechanism is configured to drive the piston to move in the piston cavity along the axial direction of the piston cylinder, so as to realize reagent exchange between the piston cavity and the reagent cavities.

In the above technical solution, the gene detection device is provided with the positioning mechanism, the driving mechanism, and the executing mechanism, wherein the gene detection kit can be positioned by the positioning mechanism, and the piston cylinder of the gene detection kit can be driven by the driving mechanism to move relative to the kit body, so that the executing mechanism, when driving the piston in the piston cylinder to move, can realize exchange of reagents in different reagent cavities with the piston cavity, thus the sample can be allowed to complete the centralized extraction of multiple nucleic acid extraction steps within the gene detection kit. The gene detection device of such a structure can realize the automated extraction work of the nucleic acid of the sample, and further it is beneficial to improve the nucleic acid extraction efficiency of the sample.

In addition, the gene detection device provided in embodiments of the present disclosure further has the following additional technical features:

in some embodiments, the positioning mechanism includes a fixing seat and a positioning seat; the fixing seat is fixedly mounted on the frame, and a second through hole through which the driving mechanism passes is provided on the fixing seat; the positioning seat is movably provided on the fixing seat along a first direction, the positioning seat is configured to place and position the gene detection kit, the positioning seat has a placement position and an operation position in the first direction, wherein the first direction is perpendicular to the axial direction of the piston cylinder, and when the positioning seat is located in the placement position, the positioning seat is configured to allow taking and placing the gene detection kit, and when the positioning seat is located in the operation position, the driving mechanism can be connected to the piston cylinder.

In the above technical solution, the positioning mechanism is provided with the fixing seat configured to be mounted on the frame and the positioning seat configured to position the gene detection kit. By providing the positioning seat movably on the fixing seat along the first direction so that the positioning seat has, in the first direction, the placement position configured to allow taking and placing the gene detection kit and the operation position where the driving mechanism can be connected to the gene detection kit, the step of placing the gene detection kit can be separated from the step of connecting the driving mechanism to the gene detection kit, which, on the one hand, facilitates the operator to place the gene detection kit on the positioning mechanism, and on the other hand, is beneficial to reduce the possibility of direct contact between the operator and the driving mechanism, so as to reduce the potential safety hazard existing in the process of using the gene detection device.

In some embodiments, the positioning seat is provided with a positioning groove at one side facing away from the positioning seat in the axial direction of the piston cylinder, and the positioning groove is configured to be snapped with the gene detection kit along the first direction so as to position the gene detection kit on the positioning seat; an avoidance groove is provided on a groove bottom wall of the positioning groove, and when the positioning seat moves to the operation position along the first direction, the avoidance groove is configured to be snapped with the driving mechanism, so that the driving mechanism can be connected to the piston cylinder.

In the above technical solution, by providing the positioning groove configured to position the gene detection kit on the positioning seat, after the gene detection kit is clamped in the positioning groove along the first direction, the gene detection kit can be positioned on the positioning seat, with a simple structure and easy implementation. In addition, by providing the avoidance groove in which the driving mechanism is clamped on the groove bottom wall of the positioning groove, when the positioning seat moves to the operation position along the first direction, at least a part of the driving mechanism can extend into the positioning groove, thus facilitating the connection of the driving mechanism to the piston cylinder of the gene detection kit.

In some embodiments, a groove side wall of the positioning groove has a first guide slope, and the first guide slope is configured to guide the gene detection kit into the positioning groove along the first direction.

In the above technical solution, by providing the first guide slope on the groove side wall of the positioning groove, the first guide slope can play a certain role in guiding the gene detection kit, thus it is convenient for the operator to place the gene detection kit in the positioning groove of the positioning seat under the guidance of the first guide slope, and it is further beneficial to save the operator's operating time in positioning the gene detection kit on the positioning seat.

In some embodiments, the positioning mechanism further includes a limiting component; and the limiting component is provided on the positioning seat, and the limiting component is configured to prevent the gene detection kit from exiting from the positioning groove along the first direction.

In the above technical solution, the positioning mechanism is further provided with a limiting component. The limiting component can limit the gene detection kit placed in the positioning groove of the positioning seat, so as to reduce the phenomenon that the gene detection kit exits from the positioning groove in the process of performing the nucleic acid extraction or in the process that the positioning seat moves from the placement position to the operation position, thus, it is beneficial to improve the reliability of positioning the gene detection kit by the positioning mechanism, so as to ensure the smooth progress of the nucleic acid extraction work of the gene detection device.

In some embodiments, the limiting component includes a limiting part; the positioning seat is provided thereon with a third through hole, wherein the third through hole penetrates through two sides of the positioning seat in the axial direction of the piston cylinder, the limiting part is movably inserted into the third through hole along the axial direction of the piston cylinder, and two ends of the limiting part in the axial direction of the piston cylinder are respectively configured to extend out from two sides of the positioning seat; the fixing seat is provided with, on a side facing the positioning seat in the axial direction of the piston cylinder, a second guide slope to be abutted by the limiting part. When the positioning seat moves from the placement position to the operation position along the first direction, the limiting part is configured to move along the axial direction of the piston cylinder relative to the positioning seat under the guidance of the second guide slope, so that one end of the limiting part extends out from one side of the positioning seat facing away from the fixing seat in the axial direction of the piston cylinder, so that the limiting part can be abutted by the gene detection kit in the first direction.

In the above technical solution, the positioning seat is provided thereon with the third through hole penetrating through two sides of the positioning seat along the axial direction of the piston cylinder. By providing the limiting part movably in the third through hole along the axial direction of the piston cylinder, and providing the second guide slope abutted by the limiting part on the fixing seat, in the process that the positioning seat moves from the placement position to the operation position along the first direction, the limiting part can move in the third through hole under the guidance of the second guide slope, so that the limiting part can extend out from one side of the positioning seat facing away from the fixing seat, thus, the limiting part can be abutted by the gene detection kit, so as to prevent the gene detection kit from exiting from the positioning groove of the positioning seat. On the contrary, when the positioning seat moves from the operation position to the placement position along the first direction, the limiting part can retract into the third through hole under the action of its own gravity and the guidance of the second guide slope, so that the operator can take out the gene detection kit from the positioning groove of the positioning seat. With the limiting component of such a structure, the limiting part can be switched between two states of limiting the gene detection kit and not limiting the gene detection kit in the process of moving the positioning seat along the first direction, without requiring manual participation, reducing the operation difficulty of the gene detection device, and thus being beneficial to improve the operation efficiency of the gene detection device.

In some embodiments, the limiting component further includes a roller; and the roller is mounted at one end of the limiting part close to the fixing seat in the axial direction of the piston cylinder, and the roller is configured to abut against the second guide slope.

In the above technical solution, by providing the roller at one end of the limiting part, the limiting part can abut against the second guide slope through the roller, thus sliding friction between the limiting part and the second guide slope is converted into rolling friction, which, on the one hand, can relieve wear between the limiting part and the second guide slope, and is beneficial to prolong the service lifetime of the gene detection device, and on the other hand, can improve the guiding effect of the second guide slope to the limiting part, and is beneficial to reduce the occurrence of jamming between the limiting part and the second guide slope.

In some embodiments, the fixing seat is provided thereon with a limiting stopper, wherein the limiting stopper is configured to be abutted by the positioning seat when the positioning seat moves to the operation position in the first direction.

In the above technical solution, by providing the limiting stopper to be abutted by the positioning seat on the fixing seat, the limiting stopper can limit the positioning seat when the positioning seat moves to the operation position, that is to say, when the positioning seat moves from the placement position to the operation position along the first direction, the limiting stopper can limit the positioning seat to the operation position, so as to reduce the phenomenon that the positioning seat exceeds the stroke, thus being capable of ensuring the connection between the driving mechanism and the piston cylinder of the gene detection kit, and being beneficial to ensure the normal operation of the gene detection device.

In some embodiments, the gene detection device further includes a housing and a door; the housing is configured to accommodate the frame, and a placement port is provided at a position of the housing corresponding to the positioning mechanism; the door is movably provided on the housing, the door is configured to open or close the placement port, the door is in transmission connection with the positioning seat, and the door is configured to, when opening or closing the placement port, drive the positioning seat to move between the placement position and the operation position in the first direction.

In the above technical solution, the gene detection device is further provided with the housing, and by providing all the mechanisms such as the frame in the housing, a certain protection function can be achieved for the gene detection device by means of the housing, which is beneficial to prolong the service lifetime of the gene detection device. In addition, as the door is movably provided on the housing, and when opening or closing the placement port of the housing, the door can drive the positioning seat to move between the placement position and the operation position, that is to say, the positioning seat can be driven to move to the placement position while opening the door, and the positioning seat can be driven to move to the operation position wile closing the door, it is unnecessary to separately drive the positioning seat to move between the placement position and the operation position manually or by other mechanisms, which, on the one hand, facilitates the operator to perform an operation on the gene detection device, and helps to save the working time, and on the other hand, can effectively reduce the manufacturing costs of the gene detection device.

In some embodiments, the door is rotatably connected to the fixing seat, and the door is configured to open or close the placement port when it is rotated relative to the fixing seat; the door is provided thereon with a transmission member, wherein two ends of the transmission member are respectively hinged to the door and the positioning seat, so that when the door is rotated relative to the housing, the positioning seat can be driven by the transmission member to move between the placement position and the operation position along the first direction.

In the above technical solution, as the door is rotatably connected to the fixing seat, and the transmission member is connected between the door and the positioning seat, and two ends of the transmission member are respectively hinged to the door and the positioning seat, the positioning seat can be driven by the transmission member to move in the first direction while the door is rotated relative to the fixing seat. Such a structure is easy to implement, has low manufacturing costs, and relatively high stability.

In some embodiments, the driving mechanism includes a rotating shaft and a first driving assembly; the rotating shaft is rotatably provided on the frame, the rotating shaft extends along the axial direction of the piston cylinder, and one end of the rotating shaft in the axial direction of the piston cylinder is configured to be detachably connected to the piston cylinder; and the first driving assembly is connected to the rotating shaft, and the first driving assembly is configured to drive the rotating shaft to rotate relative to the frame, so as to drive the piston cylinder to circumferentially rotate relative to the kit body.

In the above technical solution, the driving mechanism is provided with the rotating shaft and the first driving assembly, the rotating shaft is rotatably mounted on the frame, and one end of the rotating shaft is configured to be detachably connected to the piston cylinder of the gene detection kit, so as to facilitate quick disassembly and mounting between the rotating shaft and the piston cylinder, and further the first driving assembly, when driving the rotating shaft to rotate, can drive the piston cylinder to circumferentially rotate relative to the kit body.

In some embodiments, one end of the rotating shaft in the axial direction of the piston cylinder is provided with a butt-joint groove in which the operation portion of the piston cylinder is clamped.

In the above technical solution, by providing the butt-joint groove in which the operation portion of the piston cylinder is clamped at one end of the rotating shaft, detachable connection between the rotating shaft and the piston cylinder is realized by means of clamping, so that when the gene detection kit is driven by the positioning seat to move to the operation position along the first direction, automatic connection between the operation portion of the piston cylinder and the rotating shaft can be realized, manual intervention can be further reduced, which is beneficial to improve the operation efficiency of the gene detection device, and the potential safety hazard existing in the process of using the gene detection device can be effectively reduced.

In some embodiments, the rotating shaft is of a hollow structure with two open ends, the rotating shaft is configured to be inserted by the magnetic member, and the magnetic member is configured to adsorb the magnetic beads in the piston cavity.

In the above technical solution, by providing the rotating shaft as a hollow structure with two open ends in an extending direction thereof, the magnetic member can be inserted into the rotating shaft, so that the magnetic member can abut against the piston cylinder and act on the magnetic beads in the piston cavity during the nucleic acid extraction. With such a structure, the distance between the magnetic member and the piston cylinder can be effectively shortened, further being beneficial to enhance the magnetic force of the magnetic member to the magnetic beads in the piston cavity.

In some embodiments, the driving mechanism further includes a detection assembly; and the detection assembly is configured to detect an angle of rotation of the rotating shaft relative to the frame.

In the above technical solution, the driving mechanism is further provided with a detection assembly. The rotation angle of the rotating shaft can be detected by the detection assembly, so that accuracy of rotation of the rotating shaft relative to the frame can be improved, so as to control the accuracy of circumferential rotation of the piston cylinder relative to the kit body, further being beneficial to the control accuracy of the gene detection device, thus ensuring smooth progress of the nucleic acid extraction work.

In some embodiments, the executing mechanism includes a piston rod and a second driving assembly; the piston rod is movably provided on the frame along the axial direction of the piston cylinder. At least a part of the piston rod is configured to extend into the piston cavity. The end of the piston rod extending into the piston cavity is provided with an execution end, and the execution end is configured to be connected to the piston; the second driving assembly is connected to the piston rod, and the second driving assembly is configured to drive the piston rod to move relative to the frame along the axial direction of the piston cylinder, so as to drive the piston to move along the axial direction of the piston cylinder in the piston cavity.

In the above technical solution, the executing mechanism is provided with the piston rod and the second driving assembly. The piston rod can be driven by the second driving assembly to move along the axial direction of the piston cylinder, so that at least a part of the piston rod can extend into the piston cavity, thus, after the execution end of the piston rod is connected to the piston, the piston rod can be driven by the second driving assembly to drive movement of the piston in the piston cavity, so as to realize the automation of the reagent exchange work between the piston cavity and the reagent cavity.

In some embodiments, one end of the piston in the axial direction of the piston cylinder is provided with a clamping groove, and the clamping groove is configured to be snapped with the execution end.

In the above technical solution, by providing the clamping groove in which the execution end of the piston rod is clamped at one side of the piston, the detachable connection between the execution end of the piston rod and the piston is realized, which, on the one hand, facilitates the connection of the execution end of the piston rod, after being inserted into the piston cavity, to the piston, and on the other hand, facilitates the detachment of the execution end of the piston rod from the piston after the nucleic acid extraction work of the sample is completed.

In some embodiments, the piston rod has a first position and a second position in the axial direction of the piston cylinder; when the piston rod is located at the first position, the execution end of the piston rod can be clamped in the clamping groove of the piston, and when the piston rod is located at the second position, the execution end of the piston rod can exit from the clamping groove of the piston; and the second driving assembly is configured to drive the piston rod to move between the first position and the second position along the axial direction of the piston cylinder.

In the above technical solution, the piston rod can be driven by the second driving assembly to move between the first position and the second position along the axial direction of the piston cylinder, so that the execution end of the piston rod, driven by the second driving assembly, can be automatically clamped in the clamping groove of the piston or automatically exit from the clamping groove of the piston, thus, the degree of automation of the gene detection device is further improved, so as to achieve automatic connection and automatic detachment between the piston rod and the piston.

In some embodiments, the executing mechanism further includes two limiting sensors; the two limiting sensors are arranged at intervals on the frame along the axial direction of the piston cylinder, and the two limiting sensors are respectively configured to limit the first position and the second position of the piston rod in the axial direction of the piston cylinder.

In the above technical solution, by providing two limiting sensors at intervals on the frame along the axial direction of the piston cylinder, the two limiting sensors can limit a moving stroke of the piston rod in the axial direction of the piston cylinder, thus, the piston rod is limited to move between the first position and the second position, further facilitating the control over the moving stroke of the piston rod, so as to reduce the phenomenon of damage to the gene detection kit positioned on the positioning mechanism caused by excessive movement of the piston rod.

Some embodiments of the present disclosure provide a gene detection kit, which can be applied to a nucleic acid extraction step in a gene detection process, and can solve the problem that the existing gene detection kit is relatively difficult to process, which results in relatively high manufacturing costs of the gene detection kit, further greatly increasing the costs of gene detection, moreover, there are the risks of liquid leakage and blockage of the reagent channels, thus causing a relatively large potential safety hazard in the gene detection process. A specific structure of the gene detection kit is illustrated in detail below in combination with the accompanying drawings.

Figure 2:
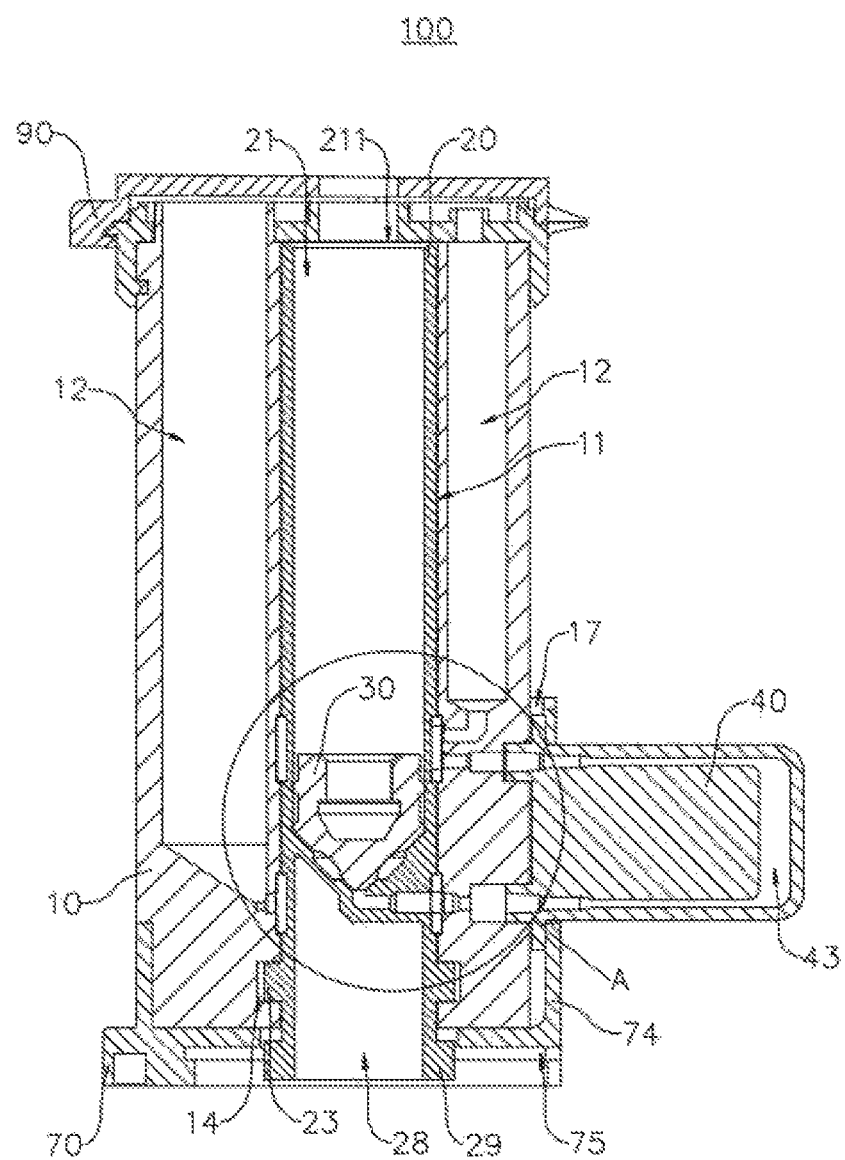
FIG. 2 is a sectional view of the gene detection kit provided in some embodiments of the present disclosure.
Figure 3:
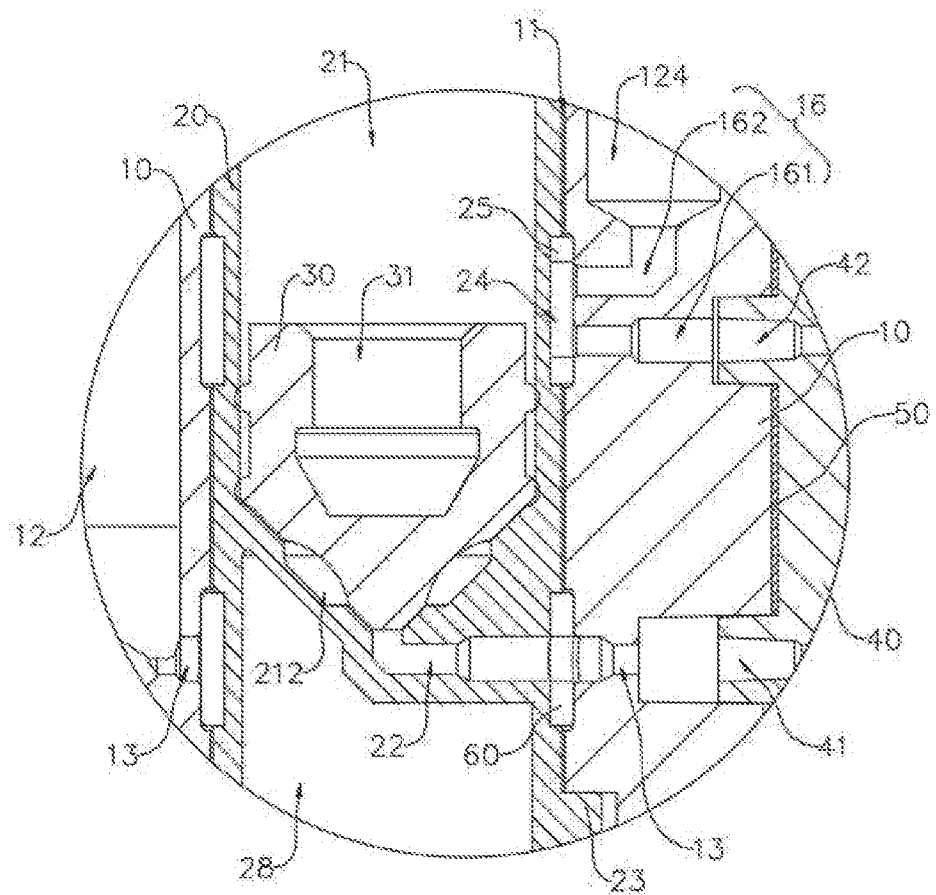
FIG. 3 is a partial enlarged view of a part A of the gene detection kit shown in FIG. 2.

According to some embodiments of the present disclosure, referring to FIG. 1, FIG. 2, and FIG. 3, FIG. 1 is a structural schematic view of a gene detection kit 100 provided in some embodiments of the present disclosure, FIG. 2 is a sectional view of the gene detection kit 100 provided in some embodiments of the present disclosure, and FIG. 3 is a partial enlarged view of a part A of the gene detection kit 100 shown in FIG. 2. An embodiment of the present disclosure provides a gene detection kit 100, wherein the gene detection kit 100 includes a kit body 10, a piston cylinder 20, and a piston 30. The kit body 10 has an accommodating cavity 11 and a plurality of reagent cavities 12. The piston cylinder 20 is provided in the accommodating cavity 11, and the piston cylinder 20 has a piston cavity 21. The piston 30 is movably provided in the piston cavity 21 along an axial direction of the piston cylinder 20. In the above, a first channel 22 in communication with the piston cavity 21 is provided on an outer circumferential surface of the piston cylinder 20, a plurality of second channels 13 are provided on an inner wall of the accommodating cavity 11, each second channel 13 is in corresponding communication with one reagent cavity 12, and the piston cylinder 20 can move relative to the kit body 10, so that the plurality of second channels 13 are alternately in communication with the first channel 22.

It should be noted that each second channel 13 is in corresponding communication with one reagent cavity 12, that is, when the first channel 22 is in communication with one second channel 13 of the plurality of second channels 13, this second channel 13 is in communication with the reagent cavity 12 corresponding thereto, and it is unnecessary for the second channel 13 to be in a state of being communicated with the corresponding reagent cavity 12 all the time.

The kit body 10 is provided with the accommodating cavity 11 and the plurality of reagent cavities 12, and the piston cylinder 20 is movably inserted into the accommodating cavity 11, thus, by providing the first channel 22 in communication with the piston cavity 21 of the piston cylinder 20 on the outer circumferential surface of the piston cylinder 20, and providing the plurality of second channels 13 in communication with respective reagent cavities 12 on the inner wall of the accommodating cavity 11, when the piston cylinder 20 is moved relative to the kit body 10 in the accommodating cavity 11, the first channel 22 can be selectively in communication with one second channel 13 of the plurality of second channels 13, further the piston cavity 21 of the piston cylinder 20 is enabled to be in communication with different reagent cavities 12, so that when the piston 30 is moved in the piston cavity 21 of the piston cylinder 20, sample extraction and exchange and transfer in different reagent cavities 12 can be realized. By using the gene detection kit 100 of such a structure, a plurality of steps of nucleic acid extraction for a sample can be completed in an enclosed space, so that the sample is extracted in a centralized manner, without the need of multiple external transfers of the sample, thus the risk of cross-contamination of the samples during the external transfer can be effectively reduced, and further it is beneficial to improve the accuracy of a gene detection result, so as to reduce harm to the patients caused by low accuracy of the gene detection result.

In addition, by providing the first channel 22 in communication with the piston cavity 21 on the outer circumferential surface of the piston cylinder 20, and providing the plurality of second channels 13 in communication with respective reagent cavities 12 on the inner wall of the accommodating cavity 11, the communication between the first channel 22 on the outer circumferential surface of the piston cylinder 20 and the second channels 13 on the inner wall of the accommodating cavity 11 can be realized just by making the piston cylinder 20 move relative to the kit body 10, so that the communication between the piston cavity 21 and one reagent cavity 12 of the plurality of reagent cavities 12 is realized, thus by using the gene detection kit 100 of such a structure, on the one hand, there is no need to provide other components such as a switching valve or a converting valve to realize the communication between the first channel 22 and the second channels 13, which is beneficial to reduce the manufacturing costs of the gene detection kit 100, and the first channel 22 can be in direct communication with the second channels 13, thus reducing a flow distance of the sample or reagent exchanged between the piston cavity 21 and the reagent cavities 12, and reducing butt-joint ports between the piston cavity 21 and the reagent cavities 12, further being capable of effectively reducing the risk of liquid leakage of the gene detection kit 100; and on the other hand, as the first channel 22 is provided on the outer circumferential surface of the piston cylinder 20 and the second channels 13 are provided on the inner wall of the accommodating cavity 11 of the kit body 10, it is convenient to process the first channel 22 and the second channels 13 on the piston cylinder 20 and the kit body 10, which is beneficial to reduce the difficulty of the manufacturing process of the first channel 22 and the second channels 13, and further can effectively reduce the processing costs.

In the above, when the first channel 22 is in communication with any one of the second channels 13, the remaining second channels 13 are blocked by the outer circumferential surface of the piston cylinder 20. The second channels 13 provided on the inner wall of the accommodating cavity 11 also can be blocked by the outer circumferential surface of the piston cylinder 20, so that in the process of movement of the piston cylinder 20 relative to the kit body 10, not only the communication between the first channel 22 and one second channel 13 of the plurality of second channels 13 can be realized, but also the blocking function for the remaining second channels 13 can be realized, thus it is unnecessary to provide other components to block the second channels 13 that are not in communication with the first channel 22. Thus, the gene detection kit 100 of such a structure is easy to operate, beneficial to reduce the operation difficulty of the gene detection kit 100, and conducive to reduce the manufacturing costs of the gene detection kit 100.

It is believed that, without being bound by theory, the piston 30 is configured to be connected to a piston rod, such that the piston rod can drive the piston 30 to move within the piston cavity 21. Exemplarily, as shown in FIG. 3, one side of the piston 30 is provided with a clamping groove 31 in which the piston rod is clamped in, so as to realize the connection between the piston 30 and the piston rod.

Figure 4:
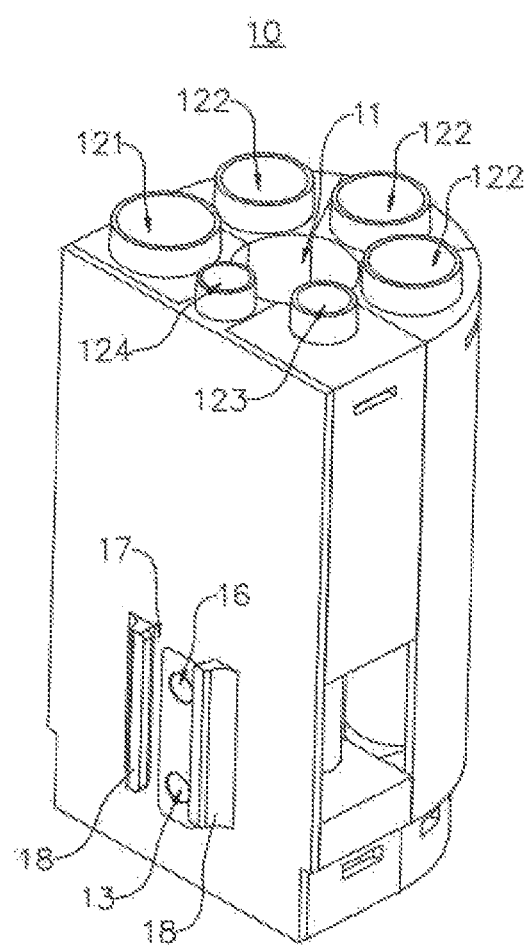
FIG. 4 is a structural schematic view of a kit body of the gene detection kit provided in some embodiments of the present disclosure.
Figure 5:
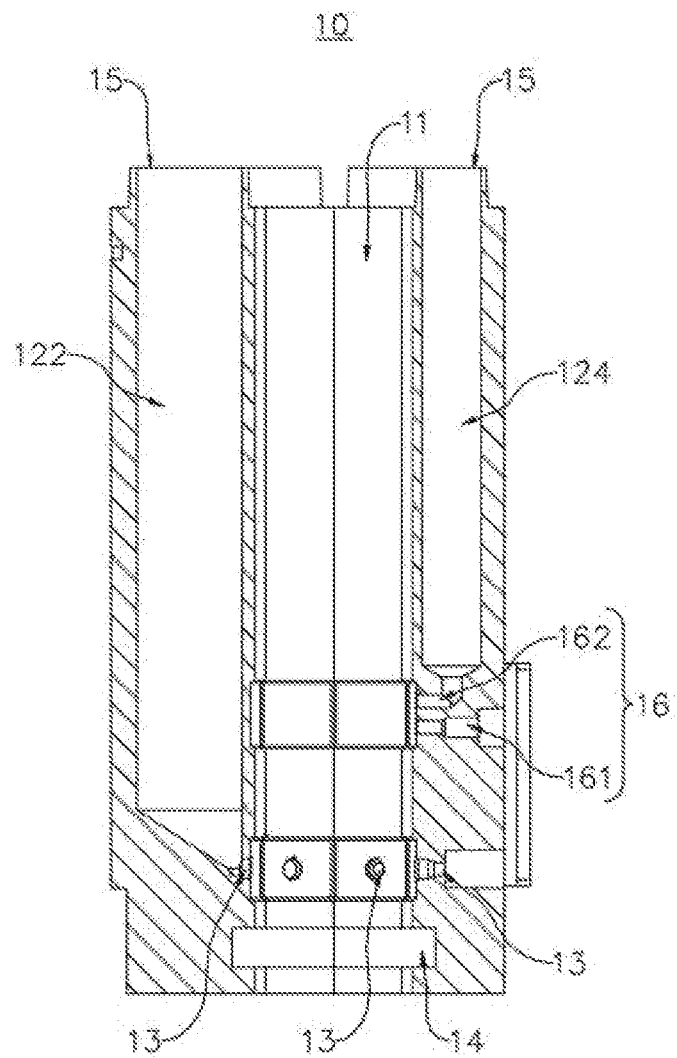
FIG. 5 is a sectional view of the kit body of the gene detection kit provided in some embodiments of the present disclosure.

According to some embodiments of the present disclosure, referring to FIG. 3, on this basis and with reference to FIG. 4 and FIG. 5, FIG. 4 is a structural schematic view of the kit body 10 of the gene detection kit 100 provided in some embodiments of the present disclosure, and FIG. 5 is a sectional view of the kit body 10 of the gene detection kit 100 provided in some embodiments of the present disclosure. The plurality of reagent cavities 12 are arranged along a circumferential direction of the piston cylinder 20. By providing the plurality of reagent cavities 12 along the circumferential direction of the piston cylinder 20, that is to say, arranging the plurality of reagent cavities 12 around the accommodating cavity 11, it is convenient to provide the second channels 13 in communication with the reagent cavities 12 on the inner wall of the accommodating cavity 11, so that the communication between the second channels 13 and the reagent cavities 12 can be realized just by providing the linear second channels 13 on the inner wall of the accommodating cavity 11. Thus, by using the gene detection kit 100 of such a structure, on the one hand, it is beneficial to reduce the length of the second channels 13, so as to reduce the flow distance of the reagent or the sample in the second channels 13, and on the other hand, it is beneficial to reduce the difficulty of the manufacturing process of the first channel 22, so as to reduce the processing costs, and the linear second channels 13 are beneficial to reduce the risk of jamming of the second channels 13.

Optionally, the piston cylinder 20 can be circumferentially rotated relative to the kit body 10, such that the plurality of second channels 13 are alternately in communication with the first channel 22. By inserting the piston cylinder 20 in the accommodating cavity 11 of the kit body 10 in a circumferentially rotatable manner, the communication between the first channel 22 and one second channel 13 of the plurality of second channels 13 can be realized just by making the piston cylinder 20 circumferentially rotate relative to the kit body 10. The gene detection kit 100 of such a structure is easy to operate and has relatively high structural stability.

In the above, the piston cylinder 20 can be circumferentially rotated relative to the kit body 10, so that the plurality of second channels 13 are alternately in communication with the first channel 22, that is, the plurality of second channels 13 are arranged on the inner wall of the accommodating cavity 11 along the circumferential direction of the piston cylinder 20, and each second channel 13 is in communication with one reagent cavity 12 arranged along the circumferential direction of the piston cylinder 20, so that when the piston cylinder 20 is rotated circumferentially relative to the kit body 10, the first channel 22 can be in communication with one second channel 13 of the plurality of second channels 13.

Exemplarily, six reagent cavities 12 are provided on the kit body 10, and the six reagent cavities 12 are respectively configured to perform steps such as lysing, washing, elution, and product output for the sample. Likewise, there are also six second channels 13 provided on the inner wall of the accommodating cavity 11. In other embodiments, the reagent cavities 12 also can be in other numbers, for example, there are four, five, seven reagent cavities 12, etc. In a practical production process, different numbers of reagent cavities 12 can be provided according to practical requirements, so as to complete the extraction process of nucleic acid.

Figure 6:
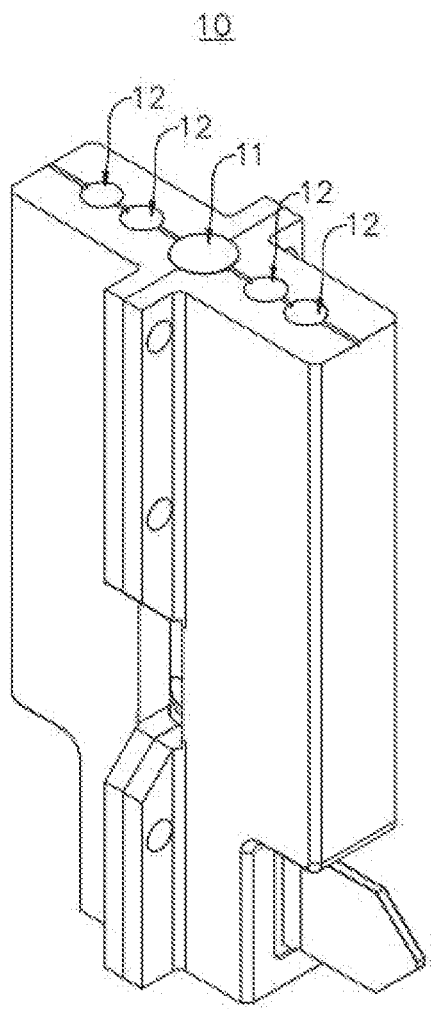
FIG. 6 is a structural schematic view of the kit body of the gene detection kit provided in some other embodiments of the present disclosure.
Figure 7:
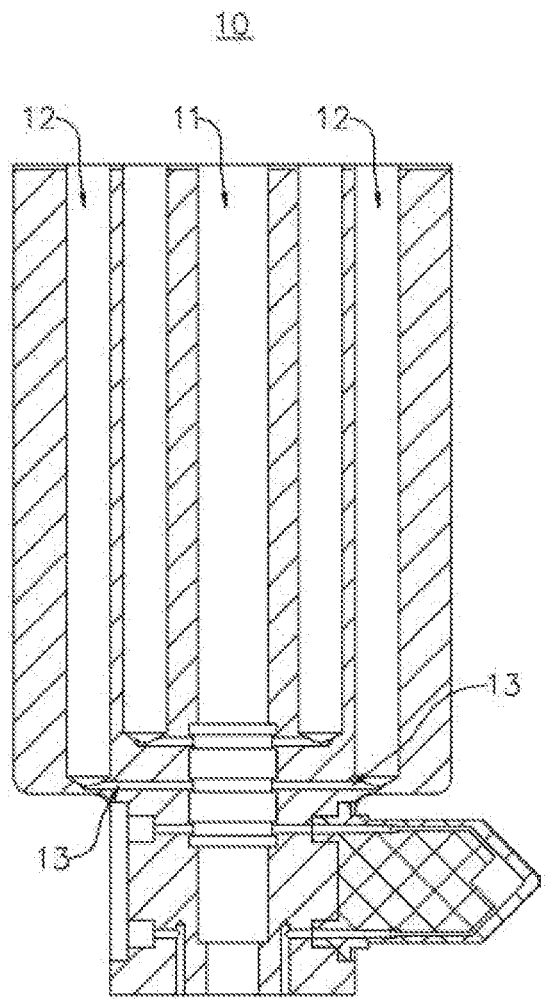
FIG. 7 is a sectional view of the kit body of the gene detection kit provided in some other embodiments of the present disclosure.

It should be noted that in other embodiments, the gene detection kit 100 further may be of other structures, for example, as shown in FIG. 6 and FIG. 7, FIG. 6 is a structural schematic view of the kit body 10 of the gene detection kit 100 provided in some other embodiments of the present disclosure, and FIG. 7 is a sectional view of the kit body 10 of the gene detection kit 100 provided in some other embodiments of the present disclosure. In a radial direction of the accommodating cavity 11, one part and the other part of the plurality of reagent cavities 12 are respectively located at two sides of the accommodating cavity 11, and likewise, one part and the other part of the plurality of second channels 13 are respectively located at two opposite sides of the inner wall of the accommodating cavity 11, and a plurality of second channels 13 located at one side of the inner wall of the accommodating cavity 11 are arranged at intervals along the axial direction of the piston cylinder 20, the piston cylinder 20 is configured to be inserted into the accommodating cavity 11 in an axially movable and circumferentially rotatable manner, so that when the piston cylinder 20 is moved relative to the kit body 10, the first channel 22 can be in communication with one second channel 13 of the plurality of second channels 13, so as to realize the communication between the piston cavity 21 and different reagent cavities 12. Without doubt, the plurality of reagent cavities 12 also may be located at the same side of the accommodating cavity 11, and the plurality of second channels 13 are arranged on the inner wall of the accommodating cavity 11 at intervals along the axial direction of the piston cylinder 20, so that the communication between the first channel 22 and one second channel 13 of the plurality of second channels 13 can be realized just by making the piston cylinder 20 axially move relative to the kit body 10.

According to some embodiments of the present disclosure, as shown in FIG. 2 and FIG. 3, the outer circumferential surface of the piston cylinder 20 is provided with a limiting protrusion 23 in a protruding way, a limiting groove 14 is provided on the inner wall of the accommodating cavity 11, and the limiting groove 14 is configured to be snapped with the limiting protrusion 23, so as to restrict the axial movement of the piston cylinder 20 relative to the kit body 10.

By providing the limiting protrusion 23 on the piston cylinder 20, and providing, on the inner wall of the accommodating cavity 11, the limiting groove 14 in which the limiting protrusion 23 is clamped, a limiting function for the piston cylinder 20 can be realized with this structure, so as to reduce the phenomenon of axial movement of the piston cylinder 20 relative to the kit body 10, further the risk that the first channel 22 of the piston cylinder 20 and the second channels 13 of the kit body 10 are misaligned in the axial direction of the piston cylinder 20 can be effectively reduce, which, on the one hand, is beneficial to ensure the smooth operation of the gene detection kit 100, and on the other hand, is beneficial to reduce the risk of liquid leakage caused by the misalignment of the first channel 22 and the second channels 13.

In the above, the limiting protrusion 23 and the limiting groove 14 are both of annular structures extending along the circumferential direction of the piston cylinder 20. By providing both the limiting protrusion 23 and the limiting groove 14 to be of annular structures extending along the circumferential direction of the piston cylinder 20, the structural strength of the limiting protrusion 23 can be improved, further it is beneficial to improve the stability of limiting the piston cylinder 20 by the limiting protrusion 23 and the limiting groove 14.

It should be noted that, after the limiting protrusion 23 provided on the piston cylinder 20 is clamped in the limiting groove 14 on the inner wall of the accommodating cavity 11, the limiting groove 14 only can prevent the axial movement of the piston cylinder 20, but can allow circumferential rotation of the piston cylinder 20 relative to the kit body 10.

According to some embodiments of the present disclosure, referring to what is shown in FIG. 4 and FIG. 5, each reagent cavity 12 has an opening 15 at one end in the axial direction of the piston cylinder 20. The plurality of reagent cavities 12 include a lysing cavity 121, a washing cavity 122, an elution cavity 123, and a product output cavity 124. In the axial direction of the piston cylinder 20, bottom surfaces of the lysing cavity 121, the washing cavity 122, and the elution cavity 123 are provided opposite to respective openings 15, and the bottom surfaces of the lysing cavity 121, the washing cavity 122, and the elution cavity 123 are all inclined surfaces (FIG. 5 only shows a structure of the washing cavity 122, and it should be noted that, the lysing cavity 121 and the elution cavity 123 have the same structure as the washing cavity 122), and are gradually away from respective openings 15 from a side away from the piston cylinder 20 to a side close to the piston cylinder 20, and the second channels 13 are connected to a side of the inclined surface close to the piston cylinder 20. Without doubt, in other embodiments, the bottom surfaces of the lysing cavity 121, the washing cavity 122, and the elution cavity 123 also may be configured in a conical structure or a semi-spherical structure, etc. that is recessed away from respective openings 15 in the axial direction of the piston cylinder 20.

By providing the lysing cavity 121, the washing cavity 122, the elution cavity 123, and the product output cavity 124 on the kit body 10, after the sample is extracted through lysing, washing, and elution, it is convenient to place the extracted sample in the product output cavity 124, thus completing the extraction of the nucleic acid of the sample, so as to realize the centralized extraction of the nucleic acid of the sample. In addition, as the bottom surfaces of the lysing cavity 121, the washing cavity 122, and the elution cavity 123 are all provided as inclined surfaces which are gradually away from respective openings 15 from the side away from the piston cylinder 20 to the side close to the piston cylinder 20, and the second channels 13 penetrate through a side of the inclined surfaces close to the piston cylinder 20, that is to say, the bottom surfaces of the lysing cavity 121, the washing cavity 122, and the elution cavity 123 are all of structures recessed away from the respective openings 15 in the axial direction of the piston cylinder 20, and the second channels 13 penetrate through a lowest point of the inclined surfaces, it is convenient to discharge the reagents in the lysing cavity 121, the washing cavity 122, and the elution cavity 123 through the second channels 13, and it is beneficial to reduce the phenomenon of residual reagents in the lysing cavity 121, the washing cavity 122, and the elution cavity 123, and further the waste of the reagents can be effectively reduced.

In the above, the piston cavity 21 is configured to be pre-filled with magnetic beads, the magnetic beads are configured to adsorb the nucleic acid, and the openings 15 of the lysing cavity 121, the washing cavity 122, and the elution cavity 123 are configured to allow pre-fill reagents to the lysing cavity 121, the washing cavity 122, and the elution cavity 123, for example, the lysing cavity 121 is configured to be pre-filled with a lysate, so that after the sample enters the lysing cavity 121, the sample can be subjected to lysis with the lysate, so that the nucleic acid of the sample is free in the lysate, and after the lysate enters the piston cavity 21, the magnetic beads in the piston cavity 21 can adsorb the nucleic acid of the lysate; the washing cavity 122 is configured to be pre-filled with a washing solution, so that the washing solution in the washing cavity 122, after entering the piston cavity 21, can wash the lysate remaining on the magnetic beads; the elution cavity 123 is configured to be pre-filled with an eluent, so that after the eluent enters the piston cavity 21, the nucleic acid on the magnetic beads can be re-dissolved in the eluent, and finally the eluent in which the nucleic acid is dissolved can enter the product output cavity 124 for subsequent use.

Exemplarily, the six reagent cavities 12 are respectively a lysing cavity 121, three washing cavities 122, an elution cavity 123, and a product output cavity 124 that are arranged along the circumferential direction of the accommodating cavity 11. By providing three washing cavities 122, the washing effect of magnetic beads is improved, so that the phenomenon of residual lysate can be effectively reduced.

In some embodiments, the plurality of reagent cavities 12 further can include a magnetic bead cavity, and the lysing cavity 121, the magnetic bead cavity, the washing cavity 122, the elution cavity 123, and the product output cavity 124 are sequentially arranged along the circumferential direction of the piston cylinder 20. By providing the magnetic bead cavity on the kit body 10 so as to accommodate the magnetic beads, later operation and use are facilitated, and by arranging the lysing cavity 121, the magnetic bead cavity, the washing cavity 122, the elution cavity 123, and the product output cavity 124 sequentially along the circumferential direction of the piston cylinder 20, the piston cavity 21 of the piston cylinder 20 can be in communication with the lysing cavity 121, the magnetic bead cavity, the washing cavity 122, the elution cavity 123, and the product output cavity 124 in sequence, so that the order of communication between the piston cavity 21 and respective reagent cavities 12 is the same as the order of performing nucleic acid extraction for the sample, further facilitating the operation and saving the operation time, and being beneficial to improve the extraction efficiency of the nucleic acid.

In some embodiments, the plurality of reagent cavities 12 further include a drying cavity, wherein the lysing cavity 121, the washing cavity 122, the drying cavity, the elution cavity 123, and the product output cavity 124 are sequentially arranged along the circumferential direction of the piston cylinder 20. By providing the drying cavity on the kit body 10, it is convenient to dry the magnetic beads, thus it is beneficial to reduce the contamination to the eluent caused by the washing solution remaining on the magnetic beads, moreover, by arranging the lysing cavity 121, the washing cavity 122, the drying cavity, the elution cavity 123, and the product output cavity 124 sequentially along the circumferential direction of the piston cylinder 20, the piston cavity 21 of the piston cylinder 20 can be in communication with the lysing cavity 121, the washing cavity 122, the drying cavity, the elution cavity 123, and the product output cavity 124 in sequence, so that the order of communication between the piston cavity 21 and respective reagent cavities 12 is the same as the order of performing nucleic acid extraction for the sample, further facilitating the operation and saving the operation time, and being beneficial to improve the extraction efficiency of the nucleic acid.

In the above, the drying cavity is just a vacant reagent cavity 12. When the piston cavity 21 is in communication with the drying cavity, air can be pumped into and exhausted from the piston cavity 21 by moving the piston 30, so that the magnetic beads are dried by air drying.

In the present embodiment, as shown in FIG. 4, the kit body 10 is of a split-type structure, the kit body 10 is provided with a plurality of modules, each module is correspondingly provided with one reagent cavity 12, and the plurality of modules are connected end to end along the circumferential direction of the piston cylinder 20 so as to form the accommodating cavity 11 into which the piston cylinder 20 is inserted. Without doubt, in other embodiments, the kit body 10 also may be of an integrated structure, that is to say, the kit body 10 is of an integrated columnar structure, and the structure of the kit body 10 of the gene detection kit 100 is formed by providing the accommodating cavity 11 and the plurality of reagent cavities 12 on the columnar structure.

Exemplarily, the kit body 10 has six modules, each module is correspondingly provided with one reagent cavity 12, that is, among the six modules, one module is provided with the lysing cavity 121, three modules are each provided with the washing cavity 122, one module is provided with the elution cavity 123, and one module is provided with the product output cavity 124.

According to some embodiments of the present disclosure, as shown in FIG. 2 to FIG. 4, the gene detection kit 100 further includes an amplification reaction tube 40, wherein the amplification reaction tube 40 is connected to the kit body 10, the product output cavity 124 is in communication with a corresponding second channel 13 through the amplification reaction tube 40, and the amplification reaction tube 40 is configured to amplify the nucleic acid. By providing the amplification reaction tube 40 configured to amplify the nucleic acid on the kit body 10 and making the product output cavity 124 be in communication with the second channel 13 through the amplification reaction tube 40, the reagent in the piston cavity 21 can enter the amplification reaction tube 40 through the first channel 22 and the second channel 13, and can enter the product output cavity 124 after nucleic acid amplification in the amplification reaction tube 40 is completed, further the amplification step of the nucleic acid also can be completed through the gene detection kit 100, facilitating the subsequent gene detection. By using the gene detection kit 100 of such a structure, the centralized extraction work of the nucleic acid can be completed in an enclosed space, so as to reduce the risk of contamination of the sample in the process of nucleic acid extraction, and facilitate the optimization of the tedious process of nucleic acid extraction. For a specific structure of the amplification reaction tube 40, reference can be made to the related art, and details will not be described herein again.

Based on the above structure, the kit body 10 further has a third channel 16 in communication with the product output cavity 124. The amplification reaction tube 40 has an inlet 41 and an outlet 42, wherein the inlet 41 is in communication with the second channel 13 corresponding to the product output cavity 124, and the outlet 42 is in communication with the third channel 16. By providing the third channel 16 in communication with the product output cavity 124 on the kit body 10, after the inlet 41 and the outlet 42 of the amplification reaction tube 40 are respectively in communication with the second channel 13 and the third channel 16, the communication between the product output cavity 124 and the second channel 13 can be realized, with a simple structure and easy implementation.

In the above, the third channel 16 is provided on the outer circumferential surface of the kit body, and the second channel 13 configured to be in communication with the product output cavity 124 penetrates through the outer surface of the kit body 10, so that by inserting the inlet 41 and the outlet 42 of the amplification reaction tube 40 respectively into the second channel 13 and the third channel 16, the communication between the product output cavity 124 and the piston cavity 21 can be realized through the amplification reaction tube 40.

The amplification reaction tube 40 has an amplification reaction cavity 43 therein, and the amplification reaction cavity 43 is in communication with both the inlet 41 and the outlet 42 of the amplification reaction tube 40. When the piston 30 is pushed to move in the piston cavity 21, the eluent dissolved with the nucleic acid can enter the amplification reaction cavity 43 sequentially through the first channel 22, the second channel 13, and the inlet 41 of the amplification reaction tube 40, so that the nucleic acid can undergo amplification reaction in the amplification reaction cavity 43, and after the amplification reaction of the nucleic acid is completed, the piston 30 continues to be pushed to move in the piston cavity 21, and the nucleic acid having undergone the amplification reaction can be pushed into the product output cavity 124 through the outlet 42 and the third channel 16, for subsequent use.

Optionally, with continued reference to FIG. 2 to FIG. 4, the amplification reaction tube 40 is clamped to the kit body 10, the outer surface of the kit body 10 is provided with a mounting groove 17, and the amplification reaction tube 40 is clamped in the mounting groove 17, so as to realize the connection between the amplification reaction tube 40 and the kit body 10. In other embodiments, the amplification reaction tube 40 also may be connected to the kit body 10 by bonding, bolt screwing, etc.

Exemplarily, the mounting groove 17 is jointly defined by two clamping ribs 18 provided on the outer surface of the kit body 10 in a protruding way, that is to say, two clamping ribs 18 are provided on the outer circumferential surface of the kit body 10 in a protruding way, and the two clamping ribs 18 are spaced apart, so that the two clamping ribs 18 jointly define the mounting groove 17 configured to mount the amplification reaction tube 40. Without doubt, in other embodiments, the mounting groove 17 also may be of a structure recessed along a radial direction of the kit body 10 on the outer surface of the kit body 10.

Based on the above structure, the gene detection kit 100 further includes a sealing pad 50, wherein the sealing pad 50 is provided between the amplification reaction tube 40 and the kit body 10, and the sealing pad 50 is configured to seal a gap between the amplification reaction tube 40 and the kit body 10, so as to reduce the risk of liquid leakage between the amplification reaction tube 40 and the kit body 10.

Exemplarily, the sealing pad 50 may be a rubber pad or a silicone pad, etc.

Optionally, the product output cavity 124 may be in communication with the amplification reaction cavity 43 of the amplification reaction tube 40 through the third channel 16 in many ways, for example, the product output cavity 124 may be in a state of being communicated with the amplification reaction cavity 43 through the third channel 16 all the time, that is, no matter whether the second channel 13 corresponding to the product output cavity 124 is in a state of being communicated with the first channel 22 or not, the product output cavity 124 and the amplification reaction cavity 43 are in the state of being communicated through the third channel 16; without doubt, the product output cavity 124 also may be in a state of being communicated with the amplification reaction cavity 43 of the amplification reaction tube 40 through the third channel 16 only when the corresponding second channel 13 is in communication with the first channel 22.

Figure 8:
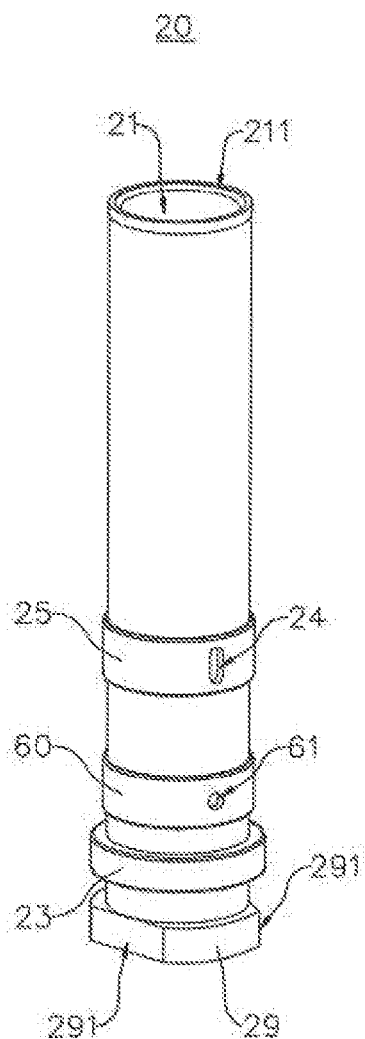
FIG. 8 is a structural schematic view of a piston cylinder of the gene detection kit provided in some embodiments of the present disclosure.
Figure 9:
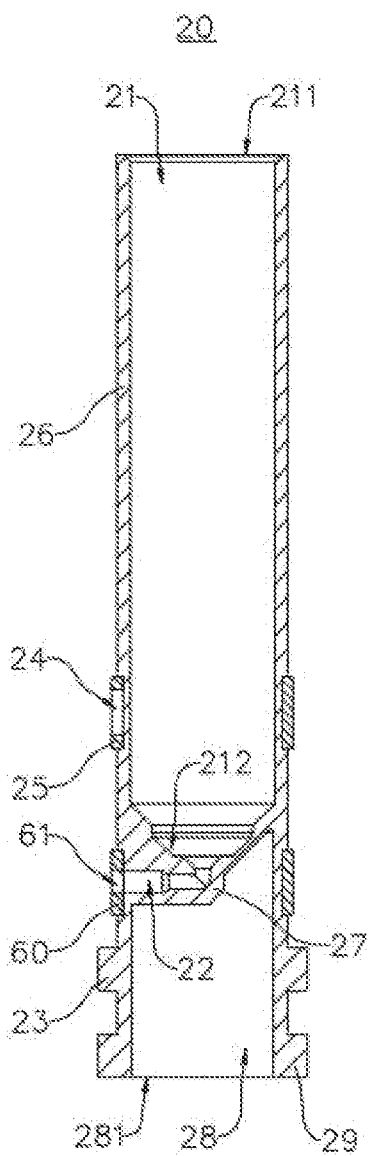
FIG. 9 is a sectional view of the piston cylinder of the gene detection kit provided in some embodiments of the present disclosure.
Figure 10:
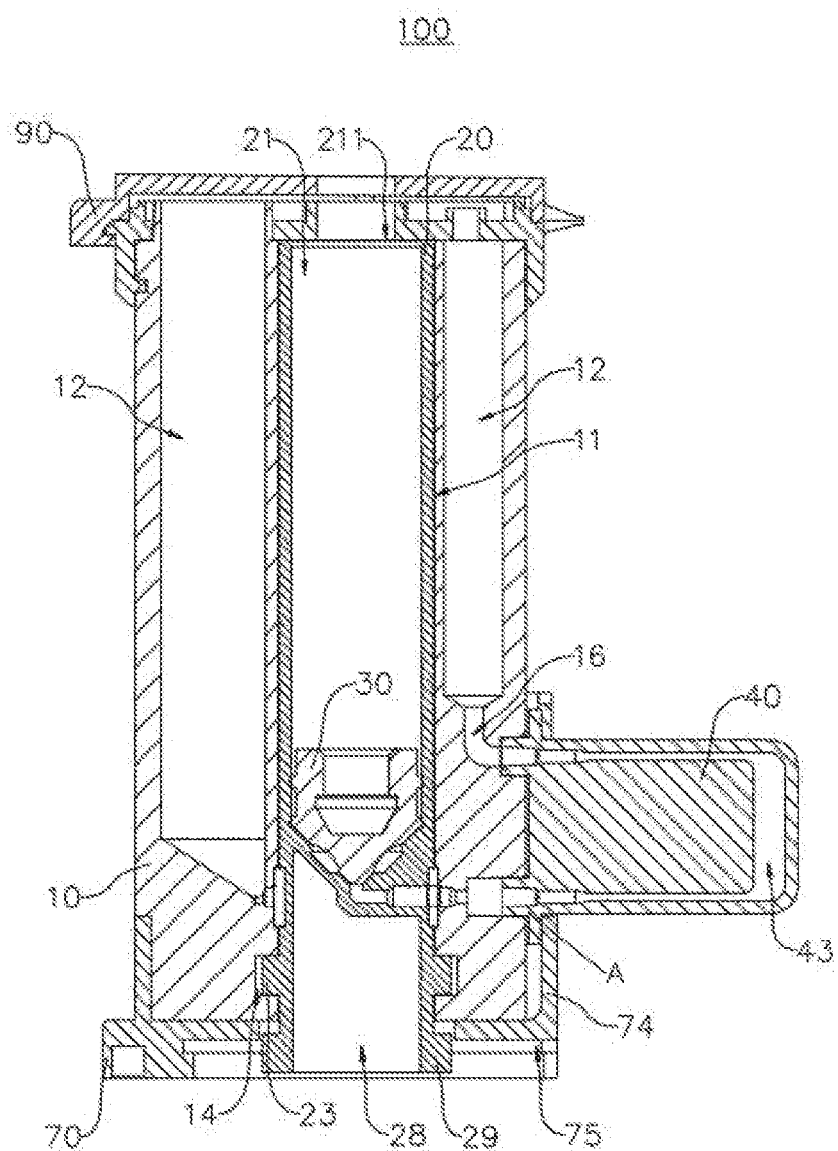
FIG. 10 is a sectional view of the gene detection kit provided in some embodiments of the present disclosure in other embodiments.

In the present embodiment, referring to FIG. 3, and on this basis, with reference to what is shown in FIG. 8 and FIG. 9, FIG. 8 is a structural schematic view of the piston cylinder 20 of the gene detection kit 100 provided in some embodiments of the present disclosure, and FIG. 9 is a sectional view of the piston cylinder 20 of the gene detection kit 100 provided in some embodiments of the present disclosure. The third channel 16 includes a first hole section 161 and a second hole section 162, wherein two ends of the first hole section 161 penetrate the outer surface of the kit body 10 and the inner wall of the accommodating cavity 11 along the radial direction of the accommodating cavity 11, the second hole section 162 is provided on the inner wall of the accommodating cavity 11 and is in communication with the product output cavity 124, and the first hole section 161 and the second hole section 162 are arranged at intervals along the axial direction of the piston cylinder 20. A strip-shaped groove 24 is provided on the outer circumferential surface of the piston cylinder 20, the strip-shaped groove 24 extends along the axial direction of the piston cylinder 20, the first hole section 161 and the second hole section 162 are both configured to be in communication with the strip-shaped groove 24. When the piston cylinder 20 is rotated to a state that the first channel 22 is in communication with the second channel 13 corresponding to the product output cavity 124, the strip-shaped groove 24 can be in communication with both the first hole section 161 and the second hole section 162, so as to realize the communication between the first hole section 161 and the second hole section 162, thus realizing the communication of the product output cavity 124 with the piston cavity 21 through the amplification reaction tube 40. At this point, the product output cavity 124 is in communication with the amplification reaction cavity 43 of the amplification reaction tube 40 through the third channel 16 only when the corresponding second channel 13 is in communication with the first channel 22. Without doubt, in other embodiments, the third channel 16 also may be of other structures. As shown in FIG. 10, FIG. 10 is a sectional view of the gene detection kit 100 provided in some embodiments of the present disclosure in other embodiments. It is also feasible that the third channel 16 is not provided with the first hole section 161 and the second hole section 162, and two ends of the third channel 16 are directly in communication with the product output cavity 124, that is, the product output cavity 124 and the amplification reaction cavity 43 are in communication all the time through the third channel 16.

With the gene detection kit 100 of such a structure, when the nucleic acid dissolved in the eluent needs to be subjected to the amplification reaction, it only needs to rotate the first channel 22 of the piston cylinder 20 to be in communication with the second channel 13 corresponding to the product output cavity 124, so that the eluent in which the nucleic acid is dissolved in the piston cavity 21 enters the amplification reaction cavity 43 of the amplification reaction tube 40. When the nucleic acid undergoes the amplification, the outer surface of the piston cylinder 20 can block the first hole section 161 and the second channel 13 corresponding to the product output cavity 124 by rotating the piston cylinder 20, so that both the inlet 41 and the outlet 42 of the amplification reaction tube 40 are closed, thus on the one hand, a reaction space of the nucleic acid amplification is reduced, and it is beneficial to amplify the nucleic acid, and on the other hand, the nucleic acid amplification reaction is allowed to be carried out in a sealed environment, thus, it is beneficial to reduce the phenomenon of leakage of aerosol generated during the amplification reaction of the nucleic acid, so as to reduce the risk of contamination to the environment.

In the above, the strip-shaped groove 24 provided on the outer surface of the piston cylinder 20 may be of various structures, wherein the strip-shaped groove 24 may be directly provided on the outer circumferential surface of the piston cylinder 20, or a component provided with the strip-shaped groove 24 may be provided on the outer circumferential surface of the piston cylinder 20. Exemplarily, in FIG. 8, a second sealing member 25 is sleeved on the outer circumferential surface of the piston cylinder 20, and the strip-shaped groove 24 is provided on the second sealing member 25, so that the first hole section 161 and the second hole section 162 can be in communication through the strip-shaped groove 24 on the second sealing member 25. With the gene detection kit 100 of such a structure, the risk of liquid leakage can be reduced when the strip-shaped groove 24 is in communication with the first hole section 161 and the second hole section 162.

Exemplarily, the material of the second sealing member 25 may be rubber, silica gel, plastic, or the like.

Based on the above structure, the outer circumferential surface of the piston cylinder 20 is provided thereon with a second annular groove extending along the circumferential direction of the piston cylinder 20, wherein the second annular groove is configured to accommodate the second sealing member 25, and an outer surface of the second sealing member 25 protrudes from the outer circumferential surface of the piston cylinder 20, so as to reduce the possibility of axial movement of the second sealing member 25 relative to the piston cylinder 20.

According to some embodiments of the present disclosure, with continued reference to what is shown in FIG. 8 and FIG. 9, the gene detection kit 100 further includes a first sealing member 60, wherein the first sealing member 60 is sleeved on the outer circumferential surface of the piston cylinder 20, and the first sealing member 60 is provided with a first through-hole 61 in communication with the first channel 22 at a position corresponding to the first channel 22.

By sleeving the first sealing member 60 at the position corresponding to the first channel 22 on the outer circumferential surface of the piston cylinder 20, on the one hand, the first sealing member 60 is enabled to seal a gap at a joint between the first channel 22 and the second channel 13 when the first channel 22 of the piston cylinder 20 is in communication with the second channel 13 of the kit body 10, so that the risk of liquid leakage at the joint between the first channel 22 and the second channel 13 can be further reduced; and on the other hand, for the second channels 13 which are not in communication with the first channel 22, the first sealing member 60 also can improve the blocking effect for this part of second channels 13, that is to say, when the first channel 22 is in communication with any one of the second channels 13, the first sealing member 60 sleeved on the piston cylinder 20 is located between the outer circumferential surface of the piston cylinder 20 and this part of second channels 13, thus the blocking effect of the outer circumferential surface of the piston cylinder 20 on this part of second channels 13 can be improved, further being beneficial to further reduce the risk of liquid leakage of the gene detection kit 100.

In the above, after the first sealing member 60 is provided in a first annular groove, an outer surface of the first sealing member 60 protrudes from the outer surface of the piston cylinder 20.

Exemplarily, the material of the first sealing member 60 may be rubber, silica gel, plastic, or the like.

Optionally, the outer circumferential surface of the piston cylinder 20 is provided thereon with the first annular groove extending along the circumferential direction of the piston cylinder 20. The first annular groove is configured to accommodate the first sealing member 60, and the first channel 22 is provided on a groove bottom wall of the first annular groove. By providing the first annular groove on the outer circumferential surface of the piston cylinder 20 to mount the first sealing member 60 in the first annular groove, the phenomenon of axial movement of the first sealing member 60 relative to the piston cylinder 20 along the axial direction of the piston cylinder 20 can be effectively reduced, so as to improve the mounting stability of the first sealing member 60, and further facilitate improving the sealing effect of the first sealing member 60.

According to some embodiments of the present disclosure, with continued reference to FIG. 8 and FIG. 9, in the axial direction of the piston cylinder 20, one end of the piston cylinder 20 is provided with a first receptacle 211 into which the piston rod is inserted, the first receptacle 211 is provided opposite to a bottom surface of the piston cavity 21, the bottom surface of the piston cavity 21 gradually gets away from the first receptacle 211 from an edge to a center, and the first channel 22 is connected to the center of the bottom surface of the piston cavity 21. In other words, the first receptacle 211 includes a proximal end and a distal end, and the bottom surface of the piston cavity 21 gradually approaches the proximal end of the first receptacle 211 from the edge to the center.

By providing the first receptacle 211 at one end of the piston cylinder 20, the piston rod can extend into the piston cavity 21 through the first receptacle 211, so that the piston rod can drive the piston 30 to move in the piston cavity 21, so as to realize reagent exchange between the piston cavity 21 and the reagent cavity 12. In addition, by providing the bottom surface of the piston cavity 21 in a structure gradually getting away from the first receptacle 211 from the edge to the center, and making the first channel 22 penetrate through a central position of the bottom surface of the piston cavity 21, that is to say, making the bottom surface of the piston cavity 21 in a structure recessed away from the first receptacle 211 from the edge to the center, and providing the first channel 22 at the lowest point of the bottom surface of the piston cavity 21, it is convenient to discharge the reagent in the piston cavity 21 from the piston cavity 21 through the first channel 22, it is beneficial to reduce the phenomenon that the reagent remains in the piston cavity 21, and further the waste of the reagent can be effectively reduced.

In the above, the bottom surface of the piston cavity 21 gradually gets away from the first receptacle 211 from the edge to the center, the first channel 22 is connected to the center of the bottom surface of the piston cavity 21, that is, the bottom surface of the piston cavity 21 is a conical surface or a semi-spherical surface recessed in a direction facing away from the first receptacle 211 along the axial direction of the piston cylinder 20, and the first channel 22 penetrates through the bottom surface of the center of the conical surface or the semi-spherical surface. Exemplarily, in FIG. 9, the bottom surface of the piston cavity 21 is a conical surface.

Optionally, a magnetic bead retention tank 212 configured to accommodate the magnetic beads is provided on the bottom surface of the piston cavity 21, and in the axial direction of the piston cylinder 20, the magnetic bead retention tank 212 is closer to the first receptacle 211 than the center of the bottom surface of the piston cavity 21. By providing the magnetic bead retention tank 212 on the bottom surface of the piston cavity 21, and making the magnetic bead retention tank 212 closer to the first receptacle 211 than the center of the bottom surface of the piston cavity 21 in the axial direction of the piston cylinder 20, that is to say, there is a distance between the magnetic bead retention tank 212 and the center of the bottom surface of the piston cavity 21 in the axial direction of the piston cylinder 20, that is, there is a distance between the magnetic bead retention tank 212 and the first channel 22 in the axial direction of the piston cylinder 20, the magnetic beads can be retained in the magnetic bead retention tank 212 on the bottom surface of the piston cavity 21 under the accommodating effect of the magnetic bead retention tank 212 on the magnetic beads, so as to reduce the risk that the magnetic beads are discharged with the reagent from the first channel 22, and the risk that the magnetic beads block the first channel 22 can be effectively reduced.

Exemplarily, in FIG. 9, the magnetic bead retention tank 212 is of an annular groove structure circumferentially surrounding the center of the bottom surface of the piston cavity 21.

According to some embodiments of the present disclosure, referring to what is shown in FIG. 9, the piston cylinder 20 includes a cylinder body 26 and a partition wall 27. The partition wall 27 is provided in the cylinder body 26 and divides an inner space of the cylinder body 26 into the piston cavity 21 and a magnetic cavity 28, wherein the piston cavity 21 and the magnetic cavity 28 are arranged along an axial direction of the cylinder body 26, the cylinder body 26 has the first receptacle 211 and a second receptacle 281 at two ends in the axial direction thereof, the first receptacle 211 is configured to allow the piston rod to be inserted into the piston cavity 21, the second receptacle 281 is configured to allow a magnetic member to be inserted into the magnetic cavity 28, and the magnetic member is configured to adsorb the magnetic beads.

In the above, when the magnetic member is inserted into the magnetic cavity 28 through the second receptacle 281, the magnetic member can adsorb the magnetic beads in the piston cavity 21, so that the magnetic beads can be tightly adsorbed in the retention tank in the piston cavity 21, thus the risk that the magnetic beads are discharged with the reagent from the first channel 22 can be further reduced.

The piston cylinder 20 has the cylinder body 26 and the partition wall 27, and the inner space of the cylinder body 26 can be divided by the partition wall 27 into the piston cavity 21 for extracting the sample and the magnetic cavity 28 into which the magnetic member is inserted, so that the magnetic member, after being inserted into the magnetic cavity 28, can adsorb the magnetic beads accommodated in the piston cavity 21, thus the piston cavity 21 of such a structure can shorten a distance between the magnetic member and the piston cavity 21 in the axial direction of the piston cylinder 20, so as to improve the magnetic effect of the magnetic member to the magnetic beads, further being beneficial to enhance the stability of magnetic beads adsorbed on the bottom surface of the piston cavity 21.

Exemplarily, in the present embodiment, the cylinder body 26 and the partition wall 27 are of an integrated structure, that is, the cylinder body 26 and the partition wall 27 are integrally formed, for example, by an injection molding process. Without doubt, in other embodiments, the cylinder body 26 and the partition wall 27 also may be of a split structures, and the partition wall 27 is bonded in the inner space of the cylinder body 26.

According to some embodiments of the present disclosure, referring to what is shown in FIG. 2, the accommodating cavity 11 penetrates through the kit body 10 along the axial direction of the piston cylinder 20, one end of the piston cylinder 20 has the first receptacle 211 into which the piston rod is inserted, one end of the piston cylinder 20, far away from the first receptacle 211 in the axial direction thereof, extends out from the kit body 10 and has an operation portion 29, wherein the operation portion 29 is configured to be connected to a driving mechanism so as to drive the piston cylinder 20 to circumferentially rotate relative to the kit body 10. In other words, the piston cylinder 20 extends out from the kit body 10 at the proximal end of the first receptacle 211 in the axial direction thereof and has the operation portion 29.

By making one end of the piston cylinder 20 far away from the first receptacle 211 in the axial direction thereof extend out from the kit body 10 and forming the operation portion 29, it is convenient to connect the operation portion 29 and the driving mechanism, thus, the driving mechanism can, through the operation portion 29, drive the piston cylinder 20 to circumferentially rotate relative to the kit body 10, so as to realize the communication between the first channel 22 of the piston cylinder 20 and one second channel 13 of the plurality of second channels 13 of the kit body 10. The gene detection kit 100 of such a structure is convenient to operate, and the automated extraction of the gene detection kit 100 can be realized, so as to improve the nucleic acid extraction efficiency of the sample.

Figure 11:
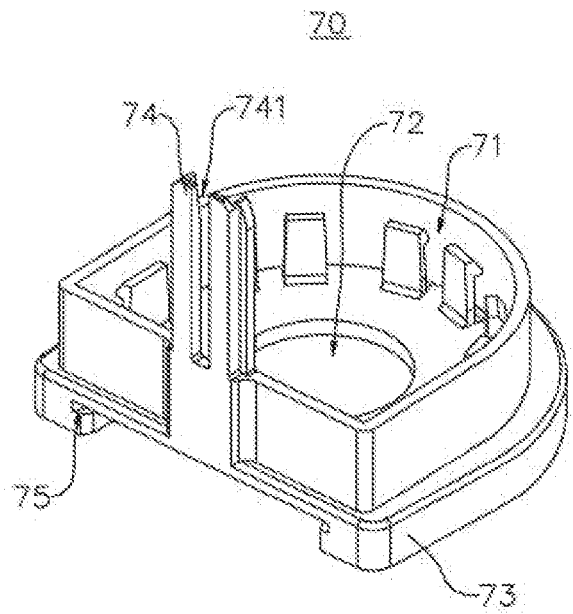
FIG. 11 is a structural schematic view of a base of the gene detection kit provided in some embodiments of the present disclosure.

Based on the above structure, and in combination with what is shown in FIG. 2 and FIG. 11, FIG. 11 is a structural schematic view of a base 70 of the gene detection kit 100 provided in some embodiments of the present disclosure. The gene detection kit 100 further includes the base 70. The base 70 is provided with an accommodating groove 71. On end of the kit body 10 close to the operation portion 29 in the axial direction of the piston cylinder 20 is inserted into the accommodating groove 71. A first avoidance hole 72 is provided in a groove bottom wall of the accommodating groove 71. The first avoidance hole 72 is configured to allow one end of the piston cylinder 20 away from the first receptacle 211 to extend out. In other words, the first avoidance hole 72 is configured to allow the piston cylinder 20 to extend out at the proximal end of the first receptacle 211. By providing the accommodating groove 71 into which the kit body 10 is inserted on the base 70 so that the kit body 10 is mounted on the base 70, the connection between the kit body 10 and the base 70 is realized, thus being beneficial to realize the disassembly and mounting of the kit body 10 and the base 70. In addition, the groove bottom wall of the accommodating groove 71 is provided thereon with the first avoidance hole 72 through which the operation portion 29 of the piston cylinder 20 passes, so that the operation portion 29 can be connected to the driving mechanism after passing through the base 70.

In the above, the kit body 10, after being inserted into the accommodating groove 71 of the base 70, is clamped with the base 70. A plurality of snap members are provided on the groove bottom wall of the accommodating groove 71 of the base 70. The plurality of snap members are arranged at intervals along the circumferential direction of the first avoidance hole 72. Correspondingly, a plurality of snap slots are provided on the outer circumferential surface of one end of the kit body 10 along the circumferential direction of the kit body 10. The snap slots and the snap members are arranged in one-to-one correspondence, so that when one end of the kit body 10 is inserted into the accommodating groove 71 of the base 70, the snap members on the base 70 can be clamped in the corresponding snap slots, so as to realize the clamping between the kit body 10 and the base 70. Without doubt, in other embodiments, the kit body 10 also may be connected to the base 70 in other ways, for example, the kit body 10 is connected to the base 70 by bonding, bolt screwing, ultrasonic welding, etc.

Optionally, the outer circumferential surface of the base 70 is further provided with a skirt 73 in a protruding way, and the skirt 73 extends along the circumferential direction of the base 70 so as to be held by an operator or clamped by an instrument.

Figure 12:
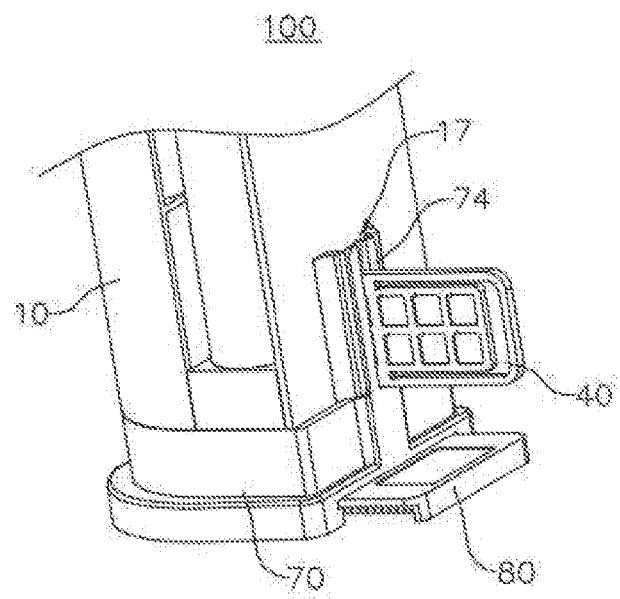
FIG. 12 is a partial schematic view of the gene detection kit provided in some embodiments of the present disclosure.

In some embodiments, referring to FIG. 11, and on this basis, with reference to what is shown in FIG. 12, FIG. 12 is a partial schematic view of the gene detection kit 100 provided in some embodiments of the present disclosure. The base 70 is further provided thereon with a clamping member 74, wherein the clamping member 74 extends along the axial direction of the piston cylinder 20 and protrudes from one side of the base 70 in the axial direction of the piston cylinder 20. The clamping member 74 is configured to be inserted into the mounting groove 17 of the kit body 10 when the kit body 10 is inserted into the accommodating groove 71 of the base 70. The clamping member 74 is provided with a clamping groove 741, the clamping groove 741 extends along the axial direction of the piston cylinder 20, and the clamping groove 741 penetrates through one end of the clamping member 74 away from the base 70 in the axial direction of the piston cylinder 20, and the clamping groove 741 is configured to be snapped with the amplification reaction tube 40 therein. With the base 70 of such a structure, when the kit body 10 is inserted into the accommodating groove 71 of the base 70, the clamping member 74 can be inserted into the mounting groove 17 of the kit body 10, and the amplification reaction tube 40 is clamped in the clamping groove 741 of the clamping member 74, so that the amplification reaction tube 40 mounted in the mounting groove 17 of the kit body 10 is further fixed by the clamping member 74, further being beneficial to improve the mounting stability of the amplification reaction tube 40.

Figure 13:
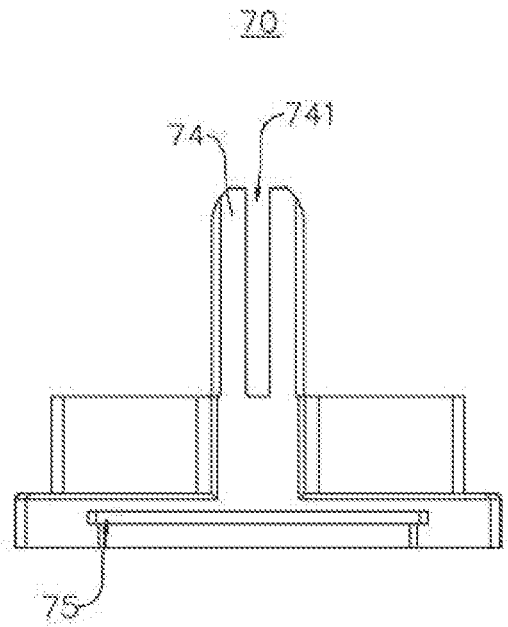
FIG. 13 is a front view of the base of the gene detection kit provided in some embodiments of the present disclosure.
Figure 14:
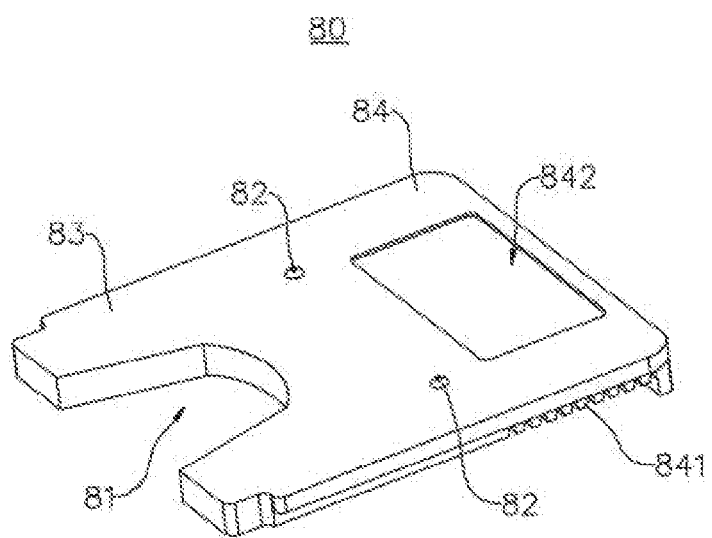
FIG. 14 is a structural schematic view of a locking member of the gene detection kit provided in some embodiments of the present disclosure.

According to some embodiments of the present disclosure, referring to FIG. 11 and FIG. 12, and on this basis, with reference to FIG. 13 and FIG. 14, FIG. 13 is a front view of the base 70 of the gene detection kit 100 provided in some embodiments of the present disclosure, and FIG. 14 is a structural schematic view of a locking member 80 of the gene detection kit 100 provided in some embodiments of the present disclosure. The gene detection kit 100 further includes the locking member 80, wherein the locking member 80 is mounted on the base 70, and the locking member 80 is configured to be connected to the operation portion 29, so as to prevent the piston cylinder 20 from circumferentially rotating relative to the kit body 10.

After the locking member 80 is connected to the operation portion 29 of the piston cylinder 20, the piston cylinder 20 can be locked, so as to prevent the piston cylinder 20 from circumferentially rotating relative to the kit body 10, thus the piston cylinder 20 can be held at a preset position, and further in the process of transporting or carrying the gene detection kit 100, the phenomenon that the piston cylinder 20 is rotated circumferentially relative to the kit body 10 can be reduced, so as to reduce the risk of liquid leakage or mutual contamination of the pre-filled reagents in the reagent cavities 12.

In the above, the locking member 80 functions to lock the piston cylinder 20. When the piston cylinder 20 needs to be locked, the piston cylinder 20 can be locked by the locking member 80, so as to prevent the piston cylinder 20 from circumferentially rotating relative to the kit body 10. The locking member 80 can be of various structures, for example, the locking member 80 can be a locking pin, and a locking hole for inserting the locking pin is provided on the piston cylinder 20, so as to realize the locking function of the piston cylinder 20. Likewise, the locking member 80 also can be a bolt, the locking member 80 is screwed on the base 70, and the locking member 80 can abut against the outer circumferential surface of the piston cylinder 20 when being tightened, so as to realize the locking function of the piston cylinder 20.

In the present embodiment, the outer circumferential surface of the base 70 is provided with an insertion slot 75 into which the locking member 80 is inserted along the radial direction of the piston cylinder 20, the operation portion 29 is wedge-shaped (referring to what is shown in FIG. 8), the locking member 80 has a wedge-shaped notch 81, and when the locking member 80 is inserted into the insertion slot 75, the wedge-shaped notch 81 is clamped with the operation portion 29, so as to prevent the piston cylinder 20 from circumferentially rotating relative to the kit body 10. By providing the operation portion 29 of the piston cylinder 20 to be wedge-shaped, and providing the wedge-shaped notch 81 matched with the operation portion 29 on the locking member 80, after the locking member 80 is inserted into the insertion slot 75 of the base 70, the operation portion 29 can be clamped in the wedge-shaped notch 81 of the locking member 80, so as to realize the locking function for the operation portion 29. In the process of transporting or carrying the gene detection kit 100 of such a structure, it only needs to insert the locking member 80 into the insertion slot 75, and on the contrary, when it is necessary to work on the gene detection kit 100, it only needs to pull out the locking member 80 from the insertion slot 75, with a simple structure, easy operation, and high stability.

In the above, the insertion slot 75 is provided on the outer circumferential surface of the piston cylinder 20, the insertion slot 75 and the accommodating groove 71 are respectively located at two sides of the base 70 in the axial direction of the piston cylinder 20, and the first avoidance hole 72 penetrates through the groove bottom wall of the accommodating groove 71 and the groove bottom wall of the insertion slot 75 in the axial direction of the piston cylinder 20, so that the operation portion 29 of the piston cylinder 20 is located in the insertion slot 75 after passing through the first avoidance hole 72, thus the locking member 80, after being inserted into the insertion slot 75, can lock the operation portion 29 of the piston cylinder 20.

It should be noted that, the operation portion 29 of the piston cylinder 20 is wedge-shaped, that is, the operation portion 29 of the piston cylinder 20 is wedge-shaped. As shown in FIG. 8, an outer circumferential surface of the operation portion 29 is provided with two clamping surfaces 291, and the two clamping surfaces 291 are arranged at an acute angle, so that the operation portion 29 is wedge-shaped. Correspondingly, the locking member 80 has a wedge-shaped notch 81 in which the operation portion 29 is clamped, that is to say, the wedge-shaped notch 81 of the locking member 80 has a shape matched with an outer contour of the operation portion 29, so that the wedge-shaped notch 81 of the locking member 80, after the operation portion 29 of the piston cylinder 20 is clamped therein, can limit the circumferential rotation of the piston cylinder 20 relative to the kit body 10.

Figure 15:
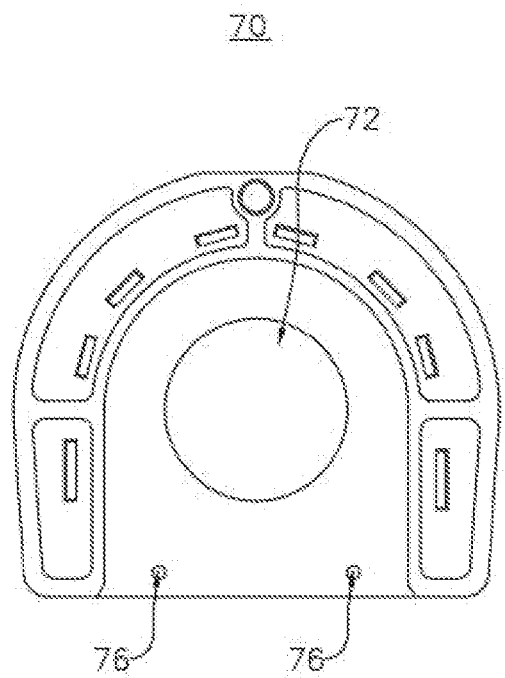
FIG. 15 is a bottom view of the base of the gene detection kit provided in some embodiments of the present disclosure.

According to some embodiments of the present disclosure, referring to FIG. 14, and on this basis, with reference to what is shown in FIG. 15, FIG. 15 is a bottom view of the base 70 of the gene detection kit 100 provided in some embodiments of the present disclosure. The base 70 is provided with a positioning hole 76, the locking member 80 is provided with a positioning boss 82, and when the locking member 80 is inserted into the insertion slot 75, the positioning boss 82 cooperates with the positioning hole 76 to prevent the locking member 80 from being detached from the insertion slot 75.

By providing the positioning hole 76 on the base 70, and correspondingly providing the positioning boss 82 on the locking member 80, after the locking member 80 is inserted into the insertion slot 75, the positioning boss 82 can be inserted into the positioning hole 76, then on the one hand, the positioning between the locking member 80 and the base 70 can be realized, so as to be beneficial to ensure that the locking member 80 is inserted in place, to improve the insertion accuracy of the locking member 80, and on the other hand, by means of this structure, the locking member 80 can be prevented from being detached from the insertion slot 75, thus, in the process of transporting or carrying the gene detection kit 100, it is beneficial to improve the reliability of locking the piston cylinder 20 by the locking member 80.

In the above, the positioning hole 76 is provided on the groove bottom wall of the insertion slot 75, that is to say, the positioning hole 76 is provided on a side of the base 70 facing away from the accommodating cavity 11 in the axial direction of the piston cylinder 20. In other embodiments, the positioning hole 76 also can be provided on the locking member 80, and correspondingly, the positioning boss 82 is provided on the base 70.

Exemplarily, two positioning bosses 82 are provided on the locking member 80, and correspondingly, there are also two positioning holes 76 provided on the base 70.

Figure 16:
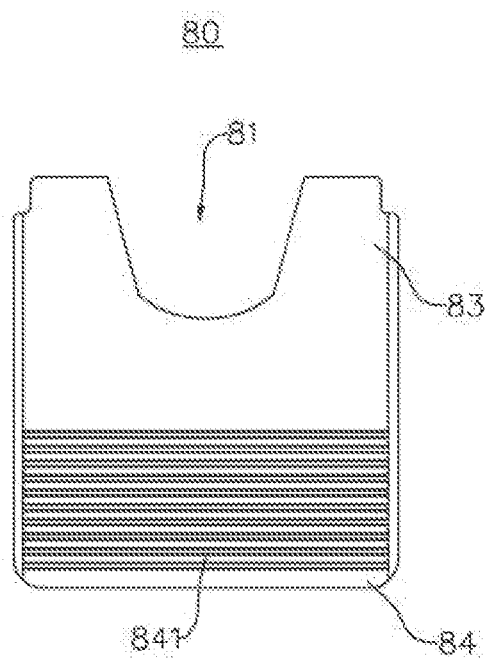
FIG. 16 is a bottom view of the locking member of the gene detection kit provided in some embodiments of the present disclosure.

According to some embodiments of the present disclosure, referring to FIG. 14, and on this basis, with reference to what is shown in FIG. 16, FIG. 16 is a bottom view of the locking member 80 of the gene detection kit 100 provided in some embodiments of the present disclosure. The locking member 80 includes a locking portion 83 and a hand-held portion 84, wherein the locking portion 83 has the wedge-shaped notch 81, the locking portion 83 is configured to be inserted into the insertion slot 75 so as to lock the operation portion 29, and the positioning boss 82 is provided on the locking portion 83. The hand-held portion 84 extends out from the outer circumferential surface of the base 70, and a plurality of anti-slip stripes 841 are provided on the hand-held portion 84.

The locking member 80 has a hand-held portion 84, and the hand-held portion 84 extends out from the outer circumferential surface of the base 70. That is to say, when the locking member 80 is inserted into the insertion slot 75, the hand-held portion 84 of the locking member 80 extends out from the outer circumferential surface of the base 70 along the radial direction of the piston cylinder 20 from the inside of the insertion slot 75, so that an operator can hold the locking member 80, so as to facilitate the insertion and pull-out of the locking member 80. In addition, by providing the plurality of anti-slip stripes 841 on the hand-held portion 84, the anti-slip performance of the locking member 80 can be effectively improved when the operator pulls out or and inserts the locking member 80, thus being beneficial to operate the locking member 80 by the operator.

In the above, the anti-slip stripes 841 are provided on a side of the locking member 80 facing away from the positioning boss 82 in a thickness direction thereof, and the plurality of anti-slip stripes 841 are sequentially arranged at intervals in the direction in which the locking member 80 is inserted into the insertion slot 75.

Based on the above structure, the hand-held portion 84 further has a label attaching area 842, wherein the label attaching area 842 is located on a side of the hand-held portion 84 facing away from the anti-slip stripes 841 in a thickness direction thereof, so as to facilitate the operator to view label information of the label attaching area 842, for example, by attaching a label "Use after pull-out" to the label attaching area 842, the operator can be reminded that the operator needs to pull out the locking member 80 when performing the nucleic acid extraction work, so as to ensure smooth progress of subsequent work.

Optionally, the locking member 80 also may be of an integrated structure, and also may be of a split structure. In the present embodiment, as shown in FIG. 14, the locking member 80 is of an integrated structure, that is to say, the locking portion 83 and the hand-held portion 84 of the locking member 80 are integrally formed, for example, integrated formation of the locking portion 83 and the hand-held portion 84 is realized through an injection molding process or a casting process, etc. Without doubt, in other implementations, the locking member 80 also may be of a split structure, that is to say, the locking portion 83 and the hand-held part 84 are two parts, and the hand-held portion 84 is connected to the locking portion 83 by means of bonding, clamping, welding, etc.

Figure 17:
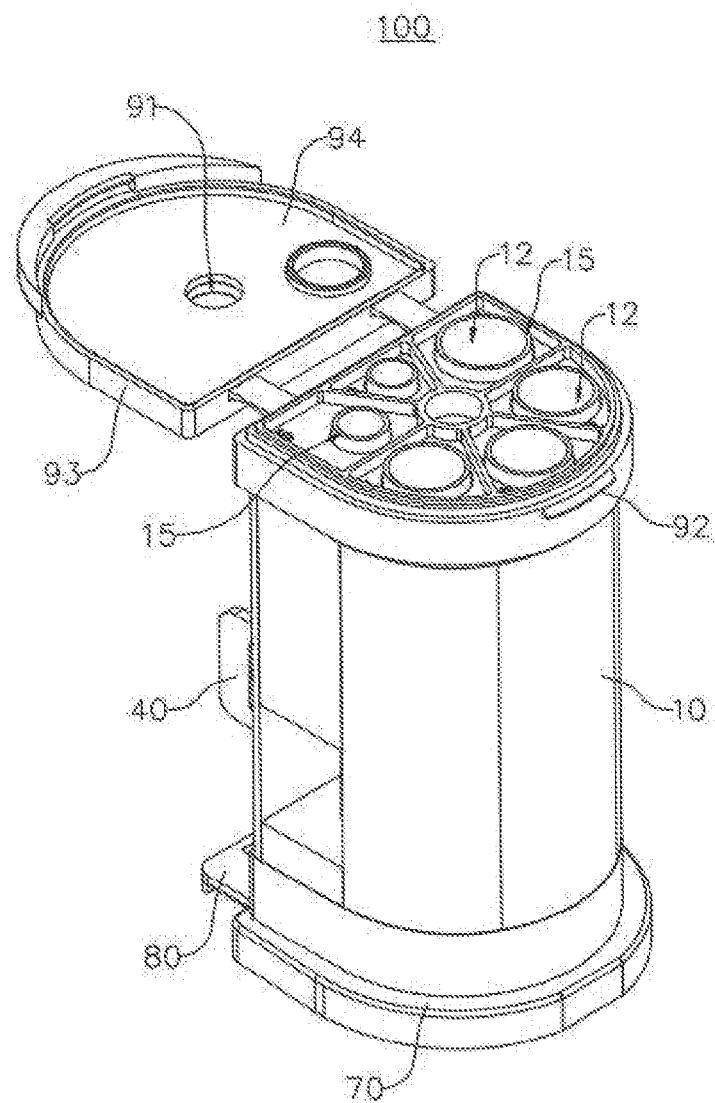
FIG. 17 is an isometric view of the gene detection kit provided in some embodiments of the present disclosure.

According to some embodiments of the present disclosure, referring to FIG. 1 and FIG. 17, FIG. 17 is an isometric view of the gene detection kit 100 provided in some embodiments of the present disclosure. Each reagent cavity 12 has an opening 15 at one end in the axial direction of the piston cylinder 20. The gene detection kit 100 further includes an end cover 90, wherein the end cover 90 is provided at one end of the kit body 10 in the axial direction of the piston cylinder 20, and the end cover 90 is configured to cover the openings 15. By providing the end cover 90 at one end of the kit body 10 to cover the openings 15 of the reagent cavities 12, it is beneficial to improve the sealing property of the reagent cavities 12, then the risk of volatilization or contamination of reagents in the reagent cavities 12 is reduced, and further the accuracy of gene detection can be effectively improved.

In the above, each reagent cavity 12 of the plurality of reagent cavities 12 provided on the kit body 10 is provided with the opening 15 at one end in the axial direction of the piston cylinder 20, configured to allow taking or placing the reagent from or into the reagent cavity 12. Likewise, the piston cylinder 20 inserted into the accommodating cavity 11 also has a first receptacle 211 at one end in the axial direction thereof, so that the piston rod can extend into the piston cavity 21 through the first receptacle 211, then the piston rod can drive the piston 30 in the piston cavity 21 to move. The openings 15 of the plurality of reagent cavities 12 and the first receptacle 211 of the piston cylinder 20 are at the same end of the kit body 10 in the axial direction of the piston cylinder 20, so that the end cover 90, when being connected to one end of the kit body 10, can cover the openings 15 of the plurality of reagent cavities 12.

Based on the above structure, the end cover 90 is provided thereon with a second avoidance hole 91, wherein the second avoidance hole 91 is provided corresponding to the first receptacle 211 of the piston cylinder 20, and the second avoidance hole 91 is configured to allow the piston rod to pass through, so that the piston rod can extend into the piston cavity 21. By providing the second avoidance hole 91 on the end cover 90, the piston rod can be inserted into the piston cavity 21 after passing through the end cover 90, so that the piston 30 can be driven by the piston rod to move in the piston cavity 21 without the need of opening the end cover 90, further helping to ensure that the nucleic acid extraction process of the sample is performed in an enclosed space, so as to reduce the possibility of contamination of the sample.

The end cover 90 may be of various structures. For example, the end cover 90 may be of a plate-like structure or a hollow structure with one open end, and after being connected to one end of the kit body 10, the end cover 90 can cover the openings 15 of the reagent cavities 12. Likewise, the end cover 90 may be connected to the kit body 10 in various ways, for example, the end cover 90 may be connected to one end of the kit body 10 by means of clamping, bolt screwing or bonding, etc.

Figure 18:
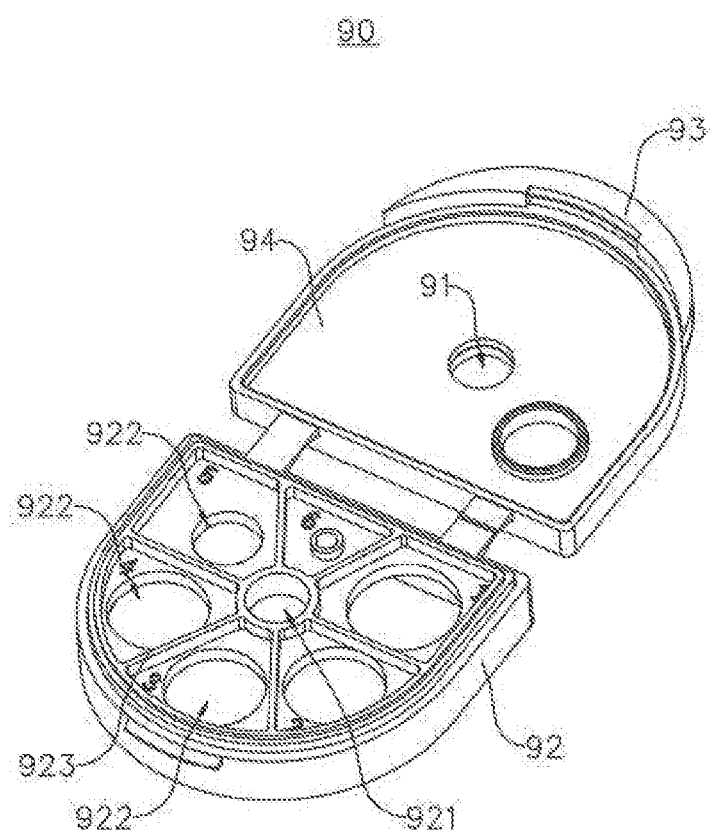
FIG. 18 is a structural schematic view of an end cover of the gene detection kit provided in some embodiments of the present disclosure.

In the present embodiment, referring to FIG. 17, and on this basis, with reference to what is shown in FIG. 18, FIG. 18 is a structural schematic view of the end cover 90 of the gene detection kit 100 provided in some embodiments of the present disclosure. The end cover 90 includes a seat body 92 and a cover body 93. The seat body 92 is clamped to one end of the kit body 10 in the axial direction of the piston cylinder 20. The seat body 92 is provided with a first pore 921 and a plurality of second pores 922, wherein the first pore 921 is provided corresponding to the first receptacle 211 of the piston cylinder 20, and each pore is provided corresponding to one opening 15 of one reagent cavity 12. The cover body 93 is configured to cover the seat body 92 so as to shelter the opening 15 of the reagent cavity 12, and the second avoidance hole 91 is provided on the cover body 93 and corresponds to the first pore 921, so that the piston rod can extend into the piston cavity 21 after passing through the second avoidance hole 91 and the first pore 921.

In the above, the cover body 93 is hinged to the seat body 92, that is to say, the cover body 93 can be rotated relative to the seat body 92, so that the opening 15 of the reagent cavity 12 can be opened or closed when the cover body 93 is rotated relative to the seat body 92. Such a structure facilitates the cover body 93 to cover the seat body 92, and can achieve certain guiding and positioning functions. In addition, it is beneficial to reduce the phenomenon of loss or mismatch of the cover body 93.

Based on the above structure, the openings 15 of the plurality of reagent cavities 12 of the kit body 10 all protrude from one end of the kit body 10 in the axial direction of the piston cylinder 20, and are inserted into corresponding second pores 922 on the seat body 92. A plurality of reinforcing ribs 923 are provided, in a protruding way, on one side of the seat body 92 facing away from the kit body 10 in the axial direction of the piston cylinder 20, the plurality of reinforcing ribs 923 are arranged at intervals along the circumferential direction of the first pore 921, and in the circumferential direction of the first pore 921, one reinforcing rib 923 is provided between every two adjacent second pores 922. In the axial direction of the piston cylinder 20, an upper surface of the seat body 92, upper surfaces of the reinforcing ribs 923, and surfaces where the openings 15 of the reagent cavities 12 are located are all located in the same plane. The gene detection kit 100 of such a structure facilitates laying a sealing film at the openings 15 of the reagent cavities 12, and as the upper surface of the seat body 92, the upper surfaces of the reinforcing ribs 923, and the surfaces where the openings 15 of the reagent cavities 12 are located are all located on the same plane in the axial direction of the piston cylinder 20, the sealing film has relatively good sealing effect, and it is beneficial to reduce the possibility of appearance of gap. When the operator needs to take or place the reagent from or into the reagent cavities 12, he/she only needs to puncture the sealing film.

Optionally, the end cover 90 further includes a third sealing member 94, wherein the third sealing member 94 is provided at one side of the cover body 93, when the cover body 93 covers the seat body 92, the third sealing member 94 is located between the cover body 93 and the seat body 92 so that the openings 15 of the reagent cavities 12 can be further sealed through the third sealing member 94, thus, multi-seal for the reagent cavities 12 can be realized, further the sealing effect to the reagent cavities 12 can be improved, and the risk that the gene detection kit 100 is prone to waste liquid leakage after the nucleic acid extraction is completed is reduced.

Exemplarily, the material of the third sealing member 94 may be silica gel, rubber, plastic, or the like.

Figure 19:
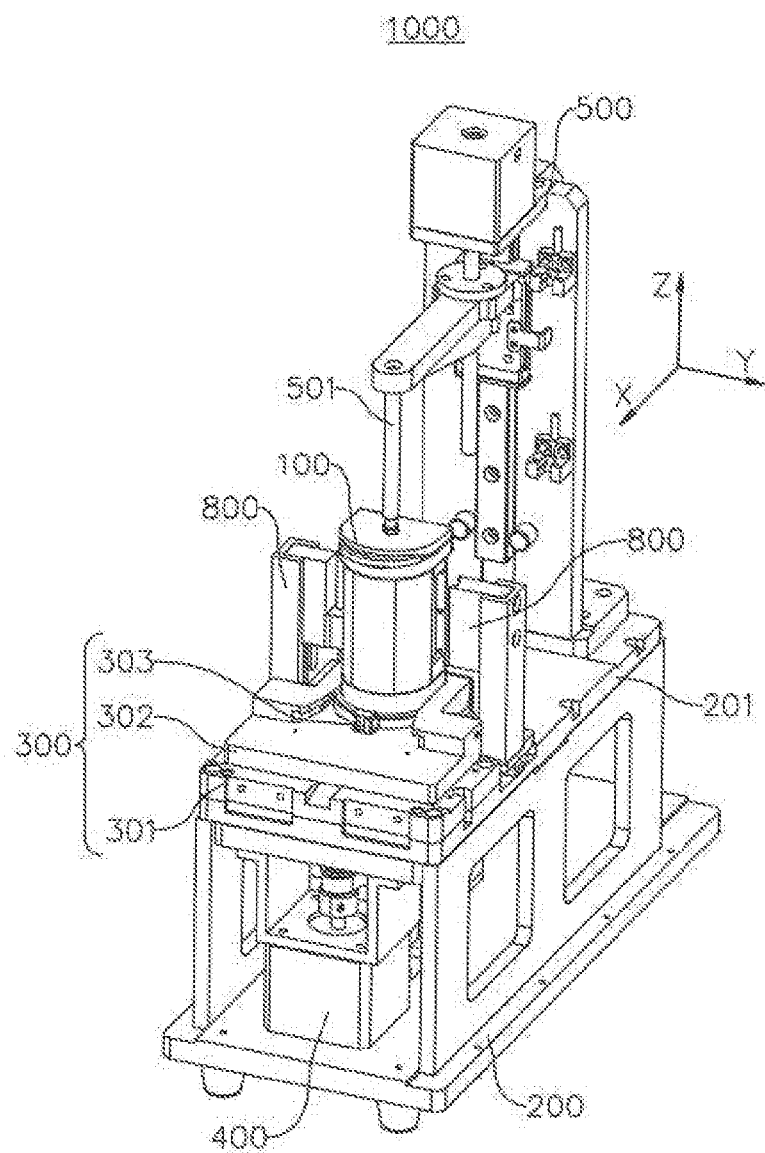
FIG. 19 is a structural schematic view of a gene detection device provided in some embodiments of the present disclosure.

In addition, an embodiment of the present disclosure further provides a gene detection device 1000 configured to be used in association with the above gene detection kit 100. The gene detection device 1000 provided in the present disclosure can be applied to a nucleic acid extraction step in a gene detection process, and is used in association with the gene detection kit 100, so that the nucleic acid of the sample can be extracted. Referring to FIG. 19, FIG. 19 is a structural schematic view of the gene detection device 1000 provided in some embodiments of the present disclosure. The gene detection device 1000 includes a frame 200, a positioning mechanism 300, a driving mechanism 400, and an executing mechanism 500. The positioning mechanism 300 is mounted on the frame 200, and the positioning mechanism 300 is configured to place and position the gene detection kit 100. The driving mechanism 400 is mounted on the frame 200, and the driving mechanism 400 is configured to drive the piston cylinder 20 to move relative to the kit body 10, so that the plurality of second channels 13 are alternately in communication with the first channel 22. The executing mechanism 500 is mounted on the frame 200, and the executing mechanism 500 is configured to drive the piston 30 to move in the piston cavity 21 along the axial direction of the piston cylinder 20, so as to realize reagent exchange between the piston cavity 21 and the reagent cavities 12.

The gene detection device 1000 is provided with the positioning mechanism 300, the driving mechanism 400, and the executing mechanism 500, the gene detection kit 100 can be positioned by the positioning mechanism 300, and the piston cylinder 20 of the gene detection kit 100 can be driven by the driving mechanism 400 to move relative to the kit body 10, so that the executing mechanism 500, when driving the piston 30 in the piston cylinder 20 to move, can realize exchange of reagents in different reagent cavities 12 with the piston cavity 21, thus the sample can be extracted in a centralized manner through multiple nucleic acid extraction steps completed in the gene detection kit 100. The gene detection device 1000 of such a structure can realize the automated extraction work of the nucleic acid of the sample, and further is beneficial to improve the nucleic acid extraction efficiency of the sample.

In the above, the frame 200 is configured to fix and mount the positioning mechanism 300, the driving mechanism 400, and the executing mechanism 500, so as to support and stabilize the positioning mechanism 300, the driving mechanism 400, and the executing mechanism 500. The frame 200 has a mounting table 201, the positioning mechanism 300, and the executing mechanism 500 are mounted on one side of the mounting table 201 in a thickness direction thereof, the driving mechanism 400 is mounted on the other side of the mounting table 201 in the thickness direction thereof, and when the gene detection kit 100 is positioned on the positioning mechanism 300, the thickness direction of the mounting table 201 is the same as the axial direction of the piston cylinder 20 of the gene detection kit 100.

It should be noted that the gene detection kit 100 is configured to be provided on the positioning mechanism 300, so that the driving mechanism 400 can be connected to the piston cylinder 20 of the gene detection kit 100, and the executing mechanism 500 can be connected to the piston 30 of the gene detection kit 100, thus when the driving mechanism 400 drives the piston cylinder 20 to rotate relative to the kit body 10, the communication between the first channel 22 of the piston cylinder 20 and one second channel 13 of the plurality of second channels 13 can be realized, so that the piston cavity 21 is in communication with one reagent cavity 12 of the plurality of reagent cavities 12, and further when the executing mechanism 500 drives the piston 30 to move in the piston cylinder 20, the piston cavity 21 can exchange reagent with the reagent cavity 12 in communication therewith, so as to complete the nucleic acid extraction step of the sample.

Figure 20:
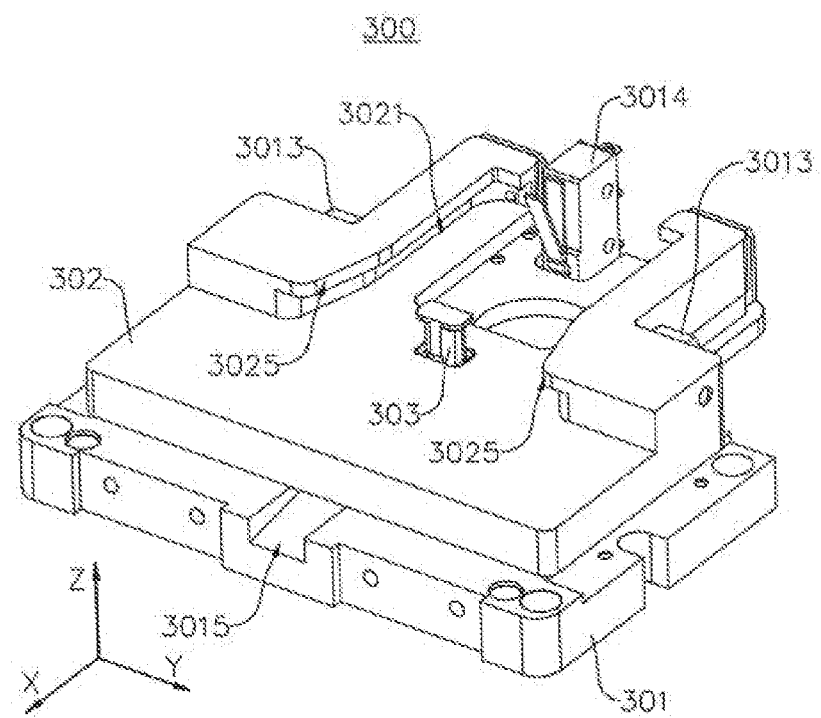
FIG. 20 is a structural schematic view of a positioning mechanism of the gene detection device provided in some embodiments of the present disclosure.
Figure 21:
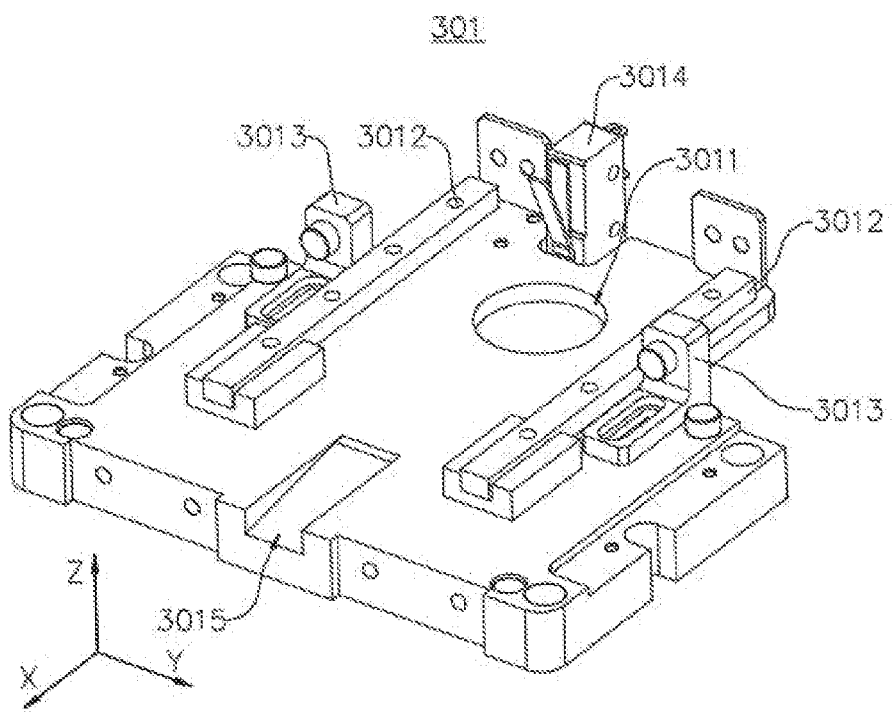
FIG. 21 is a structural schematic view of a fixing seat of the positioning mechanism provided in some embodiments of the present disclosure.

According to some embodiments of the present disclosure, referring to FIG. 19, and on this basis, with reference to FIG. 20 and FIG. 21, FIG. 20 is a structural schematic view of the positioning mechanism 300 of the gene detection device 1000 provided in some embodiments of the present disclosure, and FIG. 21 is a structural schematic view of a fixing seat 301 of the positioning mechanism 300 provided in some embodiments of the present disclosure. The positioning mechanism 300 includes the fixing seat 301 and a positioning seat 302. The fixing seat 301 is fixedly mounted on the frame 200, and a second through hole 3011 through which the driving mechanism 400 passes is provided on the fixing seat 301. The positioning seat 302 is movably provided on the fixing seat 301 along a first direction X. The positioning seat 302 is configured to place and position the gene detection kit 100. The positioning seat 302 has a placement position and an operation position in the first direction X, wherein the first direction X is perpendicular to the axial direction of the piston cylinder 20. When the positioning seat 302 is located in the placement position, the positioning seat 302 is configured to allow taking and placing the gene detection kit 100, and when the positioning seat 302 is located in the operation position, the driving mechanism 400 can be connected to the piston cylinder 20.

In the above, the fixing seat 301 is provided thereon with a second through hole 3011 through which the driving mechanism 400 passes, that is, the driving mechanism 400 can pass through the second through hole 3011 of the fixing seat 301 and then be connected to the piston cylinder 20 of the gene detection kit 100, so that the driving mechanism 400 can drive the piston cylinder 20 to circumferentially rotate relative to the kit body 10.

By providing the positioning seat 302 movably on the fixing seat 301 along the first direction X so that the positioning seat 302 has, in the first direction X, the placement position configured to allow taking and placing the gene detection kit 100 and the operation position where the driving mechanism 400 can be connected to the gene detection kit 100, the step of placing the gene detection kit 100 can be separated from the step of connecting the driving mechanism 400 to the gene detection kit 100, which, on the one hand, facilitates the operator to place the gene detection kit 100 on the positioning mechanism 300, and on the other hand, is beneficial to reduce the possibility of direct contact between the operator and the driving mechanism 400, so as to reduce the potential safety hazard existing in the process of using the gene detection device 1000.

In practical use, the first direction X is a front-back direction of the gene detection device 1000 in a horizontal plane, the axial direction of the piston cylinder 20 of the gene detection kit 100 is a vertical direction (i.e., an up-down direction) perpendicular to the horizontal plane. For convenience of description, a left-right direction of the gene detection device 1000 in the horizontal plane is defined as a second direction Y, the axial direction of the piston cylinder 20 of the gene detection kit 100 is defined as a third direction Z, and the first direction X, the second direction Y, and the third direction Z are perpendicular to each other.

In the above, the positioning mechanism 300 and the executing mechanism 500 are arranged at intervals on an upper side of the mounting table 201 of the frame 200 along the first direction X, and the positioning mechanism 300 and the driving mechanism 400 are arranged on both upper and lower sides of the mounting table 201 of the frame 200 along the third direction Z. The positioning seat 302 of the positioning mechanism 300 has, in the first direction X, the placement position configured to allow taking and placing the gene detection kit 100 and the operation position where the driving mechanism 400 can be connected to the gene detection kit 100, that is, the positioning seat 302 has the placement position and the operation position in the first direction X, and the placement position is farther away from the executing mechanism 500 than the operation position in the first direction X, so that the operator can easily place the gene detection kit 100 on the positioning seat 302.

Exemplarily, the positioning mechanism 300, the executing mechanism 500, and the driving mechanism 400 are all detachably connected to the mounting table 201 of the frame 200 by means of bolt screwing, so as to facilitate maintenance of the positioning mechanism 300, the executing mechanism 500, and the driving mechanism 400 during later use. Without doubt, in other embodiments, the positioning mechanism 300, the executing mechanism 500, and the driving mechanism 400 also may be connected to the mounting table 201 of the frame 200 by means of clamping, welding or bonding, etc.

Optionally, as shown in FIG. 21, the fixing seat 301 is provided thereon with two first slide rails 3012, wherein the two first slide rails 3012 are arranged at intervals on the fixing seat 301 along the second direction Y, the first slide rails 3012 extend along the first direction X, and the positioning seat 302 has two first sliders used in association with the first slide rails 3012, each of the first sliders is movably clamped to one first slide rail 3012 along the first direction X, so that the positioning seat 302 is movably provided on the fixing seat 301 along the first direction X.

In some embodiments, in conjunction with what is shown in FIG. 20 and FIG. 21, the fixing seat 301 further may be provided thereon with a limiting stopper 3013, wherein the limiting stopper 3013 is configured to be abutted by the positioning seat 302 when the positioning seat 302 moves to the operation position in the first direction X. By providing the limiting stopper 3013 to be abutted by the positioning seat 302 on the fixing seat 301, the limiting stopper 3013 can limit the positioning seat 302 when the positioning seat 302 moves to the operation position, that is to say, when the positioning seat 302 moves from the placement position to the operation position along the first direction X, the limiting stopper 3013 can limit the positioning seat 302 to the operation position, so as to reduce the phenomenon that the positioning seat 302 exceeds the stroke, thus being capable of ensuring the connection between the driving mechanism 400 and the piston cylinder 20 of the gene detection kit 100, and being beneficial to ensure the normal operation of the gene detection device 1000.

Exemplarily, two limiting stoppers 3013 are provided on the fixing seat 301, and the two limiting stoppers 3013 are arranged at intervals on the fixing seat 301 along the second direction Y. By limiting the stroke of the positioning seat 302 with the two limiting stoppers 3013, it is beneficial to improve the stability and accuracy of limiting the positioning seat 302 by the limiting stoppers 3013. In other embodiments, the limiting stoppers 3013 also may be of other numbers, for example, the limiting stoppers 3013 are one, three, four, etc.

Based on the above structure, the fixing seat 301 is further provided thereon with an in-place detection part 3014, and the in-place detection part 3014 is configured to detect whether the gene detection kit 100 on the positioning seat 302 is in place when the positioning seat 302 moves from the placement position to the operation position along the first direction X, thus, it can be ensured whether the gene detection kit 100 and the driving mechanism 400 are connected in place, so as to facilitate smooth progress of subsequent nucleic acid extraction work, further, it is beneficial to reduce the risk of damage to the gene detection device 1000 or failure of nucleic acid extraction due to the fact that the gene detection kit 100 is not properly connected to the driving mechanism 400.

Exemplarily, the in-place detection part 3014 may be a proximity switch.

Figure 22:
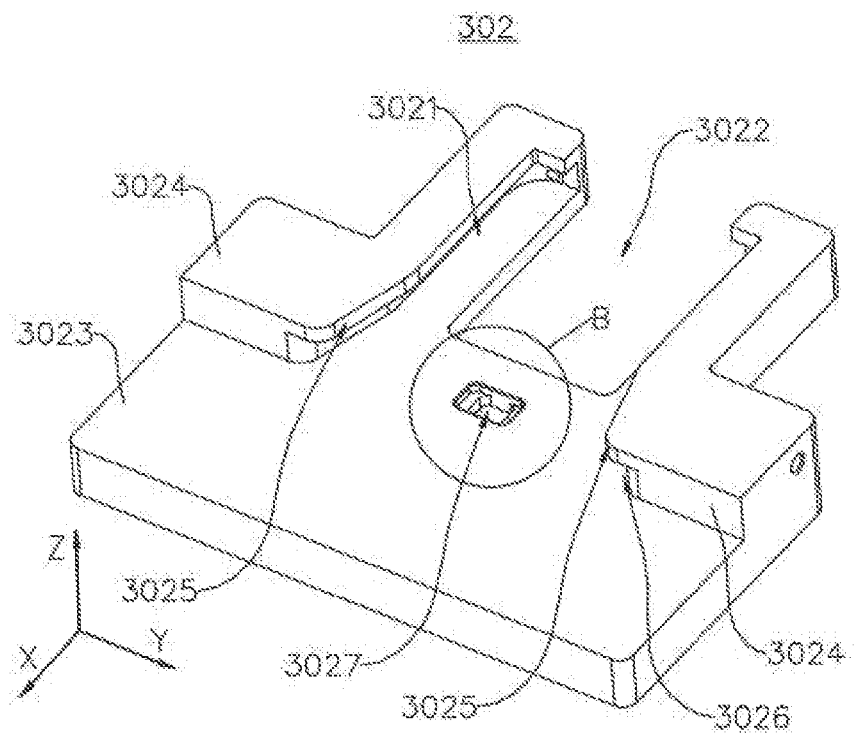
FIG. 22 is a structural schematic view of a positioning seat of the positioning mechanism provided in some embodiments of the present disclosure.

According to some embodiments of the present disclosure, referring to FIG. 19 and FIG. 20, and on this basis, with reference to FIG. 22, FIG. 22 is a structural schematic view of the positioning seat 302 of the positioning mechanism 300 provided in some embodiments of the present disclosure. The positioning seat 302 is provided with a positioning groove 3021 at one side facing away from the positioning seat 302 in the axial direction of the piston cylinder 20 (the third direction Z), and the positioning groove 3021 is configured to be snapped with the gene detection kit 100 along the first direction X so as to position the gene detection kit 100 on the positioning seat 302. An avoidance groove 3022 is provided on a groove bottom wall of the positioning groove 3021, and when the positioning seat 302 moves to the operation position along the first direction X, the avoidance groove 3022 is configured to be snapped with the driving mechanism 400, so that the driving mechanism 400 can be connected to the piston cylinder 20.

By providing the positioning groove 3021 configured to position the gene detection kit 100 on the positioning seat 302, after the gene detection kit 100 is clamped in the positioning groove 3021 along the first direction X, the gene detection kit 100 can be positioned on the positioning seat 302, with a simple structure and easy implementation. In addition, by providing on the groove bottom wall of the positioning groove 3021 the avoidance groove 3022 in which the driving mechanism 400 is clamped, when the positioning seat 302 moves to the operation position along the first direction X, at least a part of the driving mechanism 400 can extend into the positioning groove 3021, thus facilitating connecting the driving mechanism 400 to the piston cylinder 20 of the gene detection kit 100.

Optionally, the positioning seat 302 includes a positioning seat body 3023 and two positioning blocks 3024, wherein the positioning seat body 3023 is movably provided on the fixing seat 301 along the first direction X, the two positioning blocks 3024 are arranged at intervals on the positioning seat body 3023 along the second direction Y, the positioning seat body 3023 and the two positioning seats 302 jointly define the positioning groove 3021 configured to be snapped with the gene detection kit 100, an insertion port 41 of the positioning groove 3021 into which the gene detection kit 100 is inserted is located at one end of the positioning block 3024 facing away from the executing mechanism 500 in the first direction X, so that the gene detection kit 100 can be clamped between the two positioning blocks 3024 along the first direction X, thus realizing that the gene detection kit 100 is clamped in the positioning groove 3021 along the first direction X, so as to position the gene detection kit 100 on the positioning seat 302. Without doubt, the structure of the positioning seat 302 is not limited thereto, and in other embodiments, the positioning seat 302 further may be of other structures, for example, the positioning seat 302 is of a plate-like structure as a whole, and one end of the positioning seat 302 away from the executing mechanism 500 in the first direction X is provided with the positioning groove 3021 extending along the first direction X, moreover, the positioning groove 3021 penetrates through an upper surface of the positioning seat 302 in the third direction Z, so that the gene detection kit 100 is clamped in the positioning groove 3021 along the first direction X, thus, it is realized that the gene detection kit 100 is positioned on the positioning seat 302.

Exemplarily, the positioning seat 302 is of an integrated structure, that is, the positioning seat body 3023 and the two positioning blocks 3024 are integrally formed, for example, the positioning seat body 3023 and the two positioning blocks 3024 are integrally formed through processes such as casting or milling. In other embodiments, the positioning seat 302 also may be of a split structure, and the two positioning blocks 3024 are connected to the positioning seat body 3023 by means of welding or bolt screwing, etc.

In the above, the avoidance groove 3022 is provided in a position of the positioning seat body 3023 corresponding to the positioning groove 3021, and in combination with what is shown in FIG. 19 and FIG. 22, the avoidance groove 3022 is a U-shaped groove provided at one end of the positioning seat body 3023 close to the executing mechanism 500 in the first direction X, wherein the U-shaped groove penetrates through two sides of the positioning seat body 3023 in the third direction Z, so that the driving mechanism 400 can be clamped in when the positioning seat 302 moves to the operation position along the first direction X. In other embodiments, the avoidance groove 3022 also may be of a semi-circular groove structure or a V-shaped groove structure.

Based on the above structure, a groove side wall of the positioning groove 3021 has a first guide slope 3025, and the first guide slope 3025 is configured to guide the gene detection kit 100 into the positioning groove 3021 along the first direction X. By providing the first guide slope 3025 on the groove side wall of the positioning groove 3021, the first guide slope 3025 can play a certain role in guiding the gene detection kit 100, thus it is convenient for the operator to place the gene detection kit 100 in the positioning groove 3021 of the positioning seat 302 under the guidance of the first guide slope 3025, and it is further beneficial to save the operator's operating time in positioning the gene detection kit 100 on the positioning seat 302.

Exemplarily, two groove side walls of the positioning groove 3021 opposite to each other in the second direction Y are each provided with the first guide slope 3025.

In the above, the two groove side walls of the positioning groove 3021 opposite to each other in the second direction Y have the first guide slope 3025, that is, sides of the two positioning blocks 3024 opposite to each other in the second direction Y are each provided with the first guide slope 3025, and the first guide slope 3025 is located at the insertion port 41 of the positioning groove 3021 into which the gene detection kit 100 is inserted, that is to say, the insertion port 41 of the positioning groove 3021 into which the gene detection kit 100 is inserted is formed in a flared shape.

Optionally, the groove side wall of the positioning groove 3021 is further provided with a clamping groove 3026 in which the skirt 73 (as shown in FIG. 11) of the base 70 of the gene detection kit 100 is clamped, and the clamping groove 3026 is configured to limit the movement of the gene detection kit 100 along the third direction Z relative to the positioning seat 302. In the process of clamping the gene detection kit 100 in the positioning groove 3021 along the first direction X, the skirt 73 of the base 70 of the gene detection kit 100 can be clamped in the clamping groove 3026, so as to prevent the gene detection kit 100 from being detached from the positioning seat 302 along the third direction Z, thus being beneficial to improve the mounting stability of the gene detection kit 100.

According to some embodiments of the present disclosure, referring to what is shown in FIG. 19 and FIG. 20, the positioning mechanism 300 further includes a limiting component 303, wherein the limiting component 303 is provided on the positioning seat 302, and the limiting component 303 is configured to prevent the gene detection kit 100 from exiting from the positioning groove 3021 along the first direction X.

The limiting component 303 can limit the gene detection kit 100 placed in the positioning groove 3021 of the positioning seat 302, so as to reduce the phenomenon that the gene detection kit 100 exits from the positioning groove 3021 in the process of performing the nucleic acid extraction or in the process of moving the positioning seat 302 from the placement position to the operation position, thus, it is beneficial to improve the reliability of positioning the gene detection kit 100 by the positioning mechanism 300, so as to ensure the smooth progress of the nucleic acid extraction work of the gene detection device 1000.

In the above, the limiting component 303 can be of various structures, for example, the limiting component 303 can be a lock pin inserted into the positioning seat 302 or a bolt screwed onto the positioning seat 302, etc., that is to say, when the gene detection kit 100 is clamped in the positioning groove 3021 along the first direction X, by inserting the lock pin into the positioning seat 302 or screwing the bolt onto the positioning seat 302, to be abutted by the gene detection kit 100 on a side facing away from the executing mechanism 500 in the first direction X, the gene detection kit 100 can be effectively prevented from exiting from the positioning groove 3021 along the first direction X.

In the present embodiment, referring to what is shown in FIG. 20, FIG. 21, and FIG. 22 in combination, the limiting component 303 includes a limiting part 3031, and the positioning seat 302 is provided thereon with a third through hole 3027, wherein the third through hole 3027 penetrates through two sides of the positioning seat 302 along the axial direction of the piston cylinder 20 (the third direction Z), the limiting part 3031 is movably inserted into the third through hole 3027 along the axial direction of the piston cylinder 20 (the third direction Z), and two ends of the limiting part 3031 in the axial direction of the piston cylinder 20 (the third direction Z) are respectively configured to extend out from two sides of the positioning seat 302. The fixing seat 301 is provided with, on a side facing the positioning seat 302 in the axial direction of the piston cylinder 20 (the third direction Z), a second guide slope 3015 to be abutted by the limiting part 3031. When the positioning seat 302 moves from the placement position to the operation position along the first direction X, the limiting part 3031 is configured to move along the axial direction of the piston cylinder 20 (the third direction Z) relative to the positioning seat 302 under the guidance of the second guide slope 3015, so that one end of the limiting part 3031 extends out from one side of the positioning seat 302 facing away from the fixing seat 301 in the axial direction of the piston cylinder 20 (the third direction Z), so that the limiting part 3031 can be abutted by the gene detection kit 100 in the first direction X.

In the above, the third through hole 3027 is provided on the positioning seat body 3023 of the positioning seat 302, and the limiting part 3031 is configured to move relative to the positioning seat 302 along the third direction Z under the guidance of the second guide slope 3015, so that one end of the limiting part 3031 extends out from one side of the positioning seat 302 facing away from the fixed seat 301 in the third direction Z, that is, when the positioning seat 302 moves from the placement position to the operation position along the first direction X, the limiting part 3031 can move relative to the positioning seat body 3023 along the third direction Z under the guidance of the second guide slope 3015, thus, one end of the limiting part 3031 in the third direction Z can protrude from an upper surface of the positioning seat body 3023, to be abutted by one side of the gene detection kit 100 facing away from the executing mechanism 500 in the first direction X.

It can be seen from combination of FIG. 19 and FIG. 21 that in a direction approaching the executing mechanism 500 along the first direction X, a distance between the second guide slope 3015 and an upper surface of the fixing seat 301 in the third direction Z gradually decreases, so that the second guide slope 3015 is of a ramp structure gradually inclined upwards along the first direction X, thus in the process of moving the positioning seat 302 from the placement position to the operation position along the first direction X, the limiting part 3031 can move in the third through hole 3027 under the guidance of the second guide slope 3015, so that the limiting part 3031 can extend out from one side of the positioning seat 302 facing away from the fixing seat 301, thus, the limiting part 3031 can be abutted by one side of the gene detection kit 100 facing away from the executing mechanism 500 in the first direction X, so as to prevent the gene detection kit 100 from exiting from the positioning groove 3021 of the positioning seat 302, and on the contrary, when the positioning seat 302 moves from the operation position to the placement position along the first direction X, the limiting part 3031 can retract into the third through hole 3027 under the action of its own gravity and the guidance of the second guide slope 3015, so that the operator can take out the gene detection kit 100 from the positioning groove 3021 of the positioning seat 302. With the limiting component 303 of such a structure, the limiting part 3031 can be switched between two states of limiting the gene detection kit 100 and not limiting the gene detection kit 100 in the process of moving the positioning seat 302 along the first direction X, without requiring manual participation, reducing the operation difficulty of the gene detection device 1000, and being beneficial to improve the operation efficiency of the gene detection device 1000.

Figure 23:
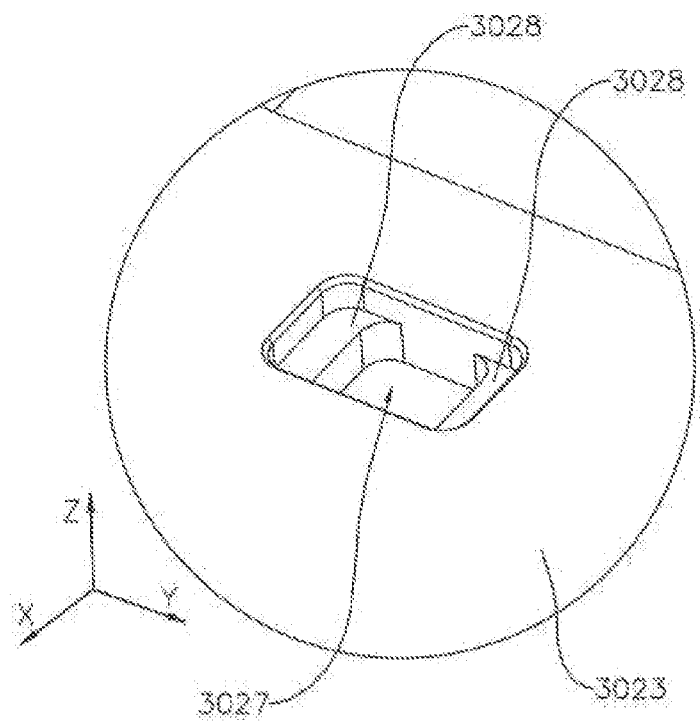
FIG. 23 is a partial enlarged view of a part B of the positioning seat of the positioning mechanism shown in FIG. 22.
Figure 24:
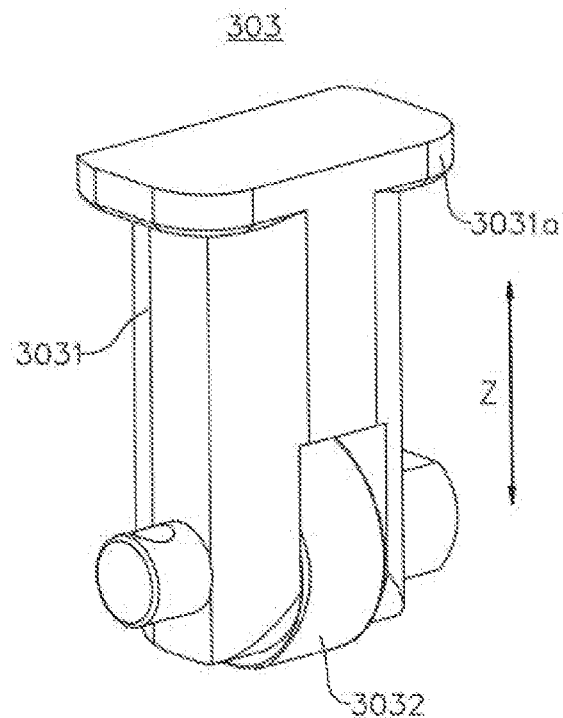
FIG. 24 is a structural schematic view of a limiting assembly of the positioning mechanism provided in some embodiments of the present disclosure.

In some embodiments of the present disclosure, referring to FIG. 22, and on this basis, with reference to FIG. 23 and FIG. 24, FIG. 23 is a partial enlarged view of a part B of the positioning seat 302 of the positioning mechanism 300 shown in FIG. 22, and FIG. 24 is a structural schematic view of a limiting component 303 of the positioning mechanism 300 provided in some embodiments of the present disclosure. A limiting block 3028 is provided on a hole wall of the third through hole 3027 in a protruding way, wherein one end of the limiting part 3031 has an abutment portion 3031a, an outer circumferential surface of the abutment portion 3031a protrudes from an outer circumferential surface of the limiting part 3031, and when the limiting part 3031 is inserted into the third through hole 3027, the limiting block 3028 is configured to be abutted by the abutment portion 3031a of the limiting part 3031, so as to prevent the limiting part 3031 from being detached from the positioning seat 302 downwards along the third direction Z.

Exemplarily, two limiting blocks 3028 are provided, and the two limiting blocks 3028 are provided, in a protruding way, on two hole walls of the third through hole 3027 that are opposite to each other in the second direction Y. In other embodiments, the limiting block 3028 also may be one, and without doubt, the limiting block 3028 also may be of an annular structure extending along a circumferential direction of the third through hole 3027.

Based on the above structure, as shown in FIG. 24, the limiting component 303 further includes a roller 3032, wherein the roller 3032 is mounted at one end of the limiting part 3031 close to the fixing seat 301 in the axial direction of the piston cylinder 20 (the third direction Z), and the roller 3032 is configured to abut against the second guide slope 3015.

The roller 3032 is provided at an end of the limiting part 3031 away from the abutment portion 3031*a* in the third direction Z. By providing the roller 3032 at one end of the limiting part 3031, the limiting part 3031 can abut against the second guide slope 3015 through the roller 3032, thus sliding friction between the limiting part 3031 and the second guide slope 3015 is converted into rolling friction, which, on the one hand, can relieve wear between the limiting part 3031 and the second guide slope 3015, and is beneficial to prolong the service lifetime of the gene detection device 1000, and on the other hand, can improve the guiding effect of the second guide slope 3015 to the limiting part 3031, and is beneficial to reduce the occurrence of jamming between the limiting part 3031 and the second guide slope 3015.

Exemplarily, the roller 3032 is rotatably connected to the limiting part 3031 through a pin shaft.

Figure 25:
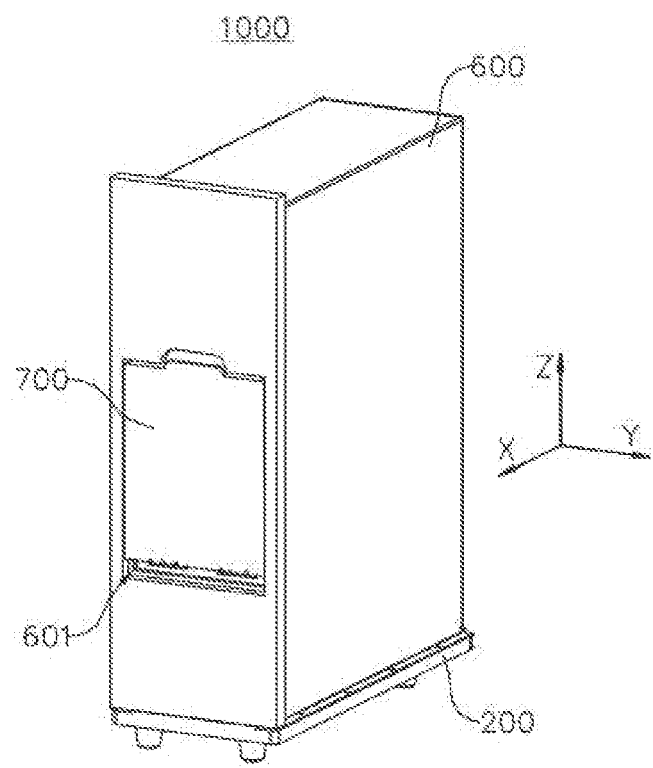
FIG. 25 is a structural schematic view of the gene detection device provided in some other embodiments of the present disclosure.
Figure 26:
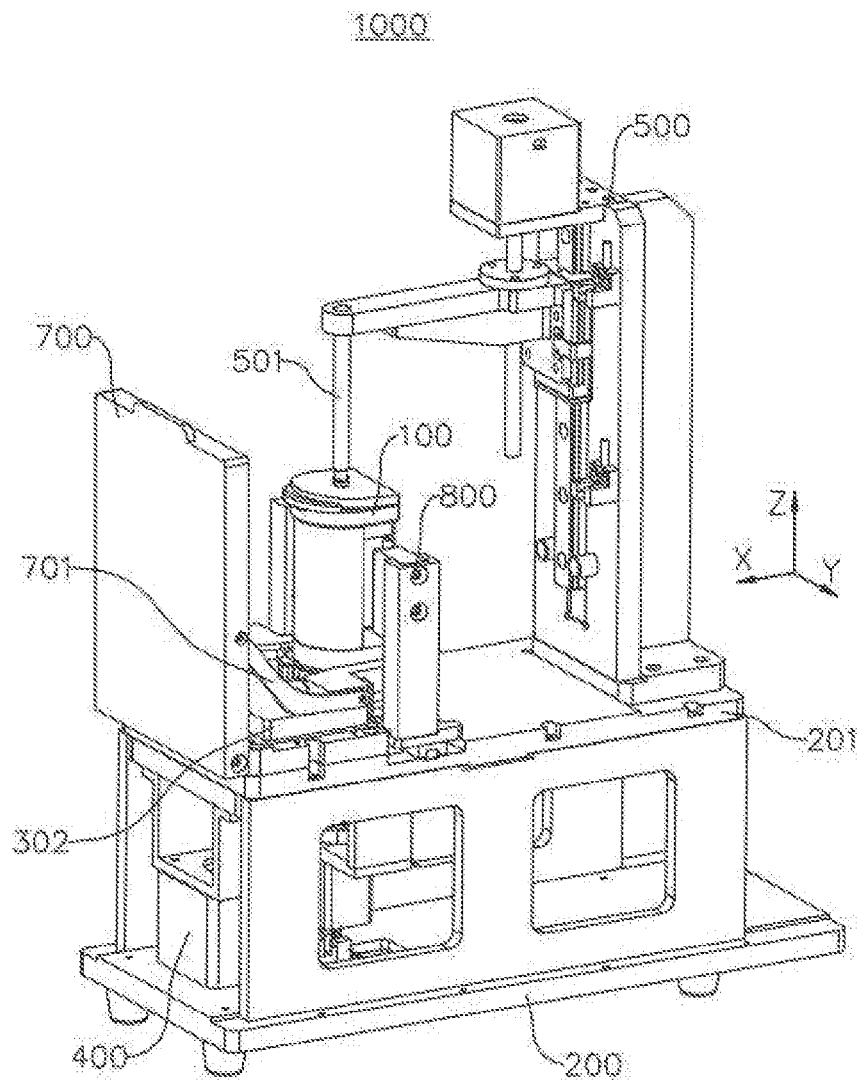
FIG. 26 is a structural schematic view of the gene detection device (after a housing being removed) provided in some other embodiments of the present disclosure.

According to some embodiments of the present disclosure, referring to what is shown in FIG. 25 and FIG. 26, FIG. 25 is a structural schematic view of the gene detection device 1000 provided in some other embodiments of the present disclosure, and FIG. 26 is a structural schematic view of the gene detection device 1000 (after a housing 600 being removed) provided in some other embodiments of the present disclosure. The gene detection device 1000 further includes a housing 600 and a door 700. The housing 600 is configured to accommodate the frame 200, and a placement port 601 is provided at a position of the housing 600 corresponding to the positioning mechanism 300. The door 700 is movably provided on the housing 600, the door 700 is configured to open or close the placement port 601, the door 700 is in transmission connection with the positioning seat 302, and the door 700 is configured to, when opening or closing the placement port 601, drive the positioning seat 302 to move between the placement position and the operation position in the first direction X.

By providing all the mechanisms such as the frame 200 in the housing 600, a certain protection function can be achieved for the gene detection device 1000 by means of the housing 600, which is beneficial to prolong the service lifetime of the gene detection device 1000. In addition, as the door 700 is movably provided on the housing 600, and when opening or closing the placement port 601 of the housing 600, the door 700 can drive the positioning seat 302 to move between the placement position and the operation position, that is to say, the positioning seat 302 can be driven to move to the placement position while opening the door 700, and the positioning seat 302 can be driven to move to the operation position wile closing the door 700, thus it is unnecessary to separately drive the positioning seat 302 to move between the placement position and the operation position manually or by other mechanisms, which, on the one hand, facilitates the operator to perform an operation on the gene detection device 1000, and helps to save the working time, and on the other hand, can effectively reduce the manufacturing costs of the gene detection device 1000.

Exemplarily, components such as the frame 200, the positioning mechanism 300, the driving mechanism 400, and the executing mechanism 500 of the gene detection device 1000 are all accommodated in the housing 600.

Based on the above structure, the door 700 is rotatably connected to the fixing seat 301, and the door 700 is configured to open or close the placement port 601 when it is rotated relative to the fixing seat 301. The door 700 is provided thereon with a transmission member 701, wherein two ends of the transmission member 701 are respectively hinged to the door 700 and the positioning seat 302, so that when the door 700 is rotated relative to the housing 600, the positioning seat 302 can be driven by the transmission member 701 to move between the placement position and the operation position along the first direction X. As the door 700 is rotatably connected to the fixing seat 301, and the transmission member 701 is connected between the door 700 and the positioning seat 302, two ends of the transmission member 701 are respectively hinged to the door 700 and the positioning seat 302, so that the positioning seat 302 can be driven by the transmission member 701 to move in the first direction X while the door 700 is rotated relative to the fixing seat 301. Such a structure is easy to implement, has low manufacturing costs, and relatively high stability.

In the above, the transmission member 701 is of a rod-shaped structure, two ends of the transmission member 701 are respectively hinged to the door 700 and the positioning seat 302, that is to say, two ends of the transmission member 701 are rotatably connected to the door 700 and the positioning seat 302, respectively, so that the door 700, the transmission member 701, and the positioning seat 302 form a crank slider structure, thus, when the door 700 is rotated relative to the fixing seat 301, the positioning seat 302 can be driven to move between the placement position and the operation position along the first direction X.

Optionally, the door 700 is rotatably connected to the fixing seat 301 of the positioning mechanism 300 through a hinge structure, so that the door 700 can be rotatably provided on the housing 600. In other embodiments, the door 700 also can be rotatably connected to the housing 600.

It should be noted that, in other embodiments, the door 700 also may be movably provided on the housing 600, for example, the door 700 is movably connected to the housing 600 along the first direction X, and the door 700 is connected to the positioning seat 302, so that the positioning seat 302 can be driven to move between the placement position and the operation position along the first direction X while the door 700 is moved along the first direction X to open or close the placement port 601 of the housing 600.

Figure 27:
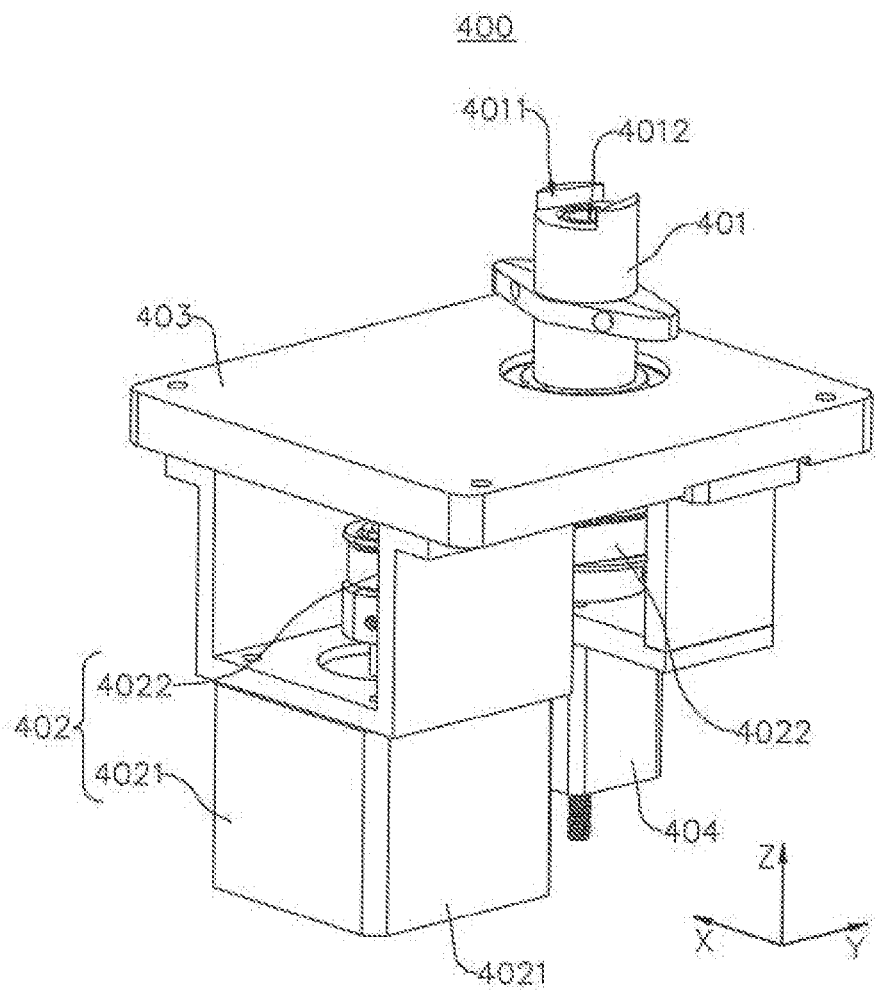
FIG. 27 is a structural schematic view of a driving mechanism of the gene detection device provided in some embodiments of the present disclosure.
Figure 28:
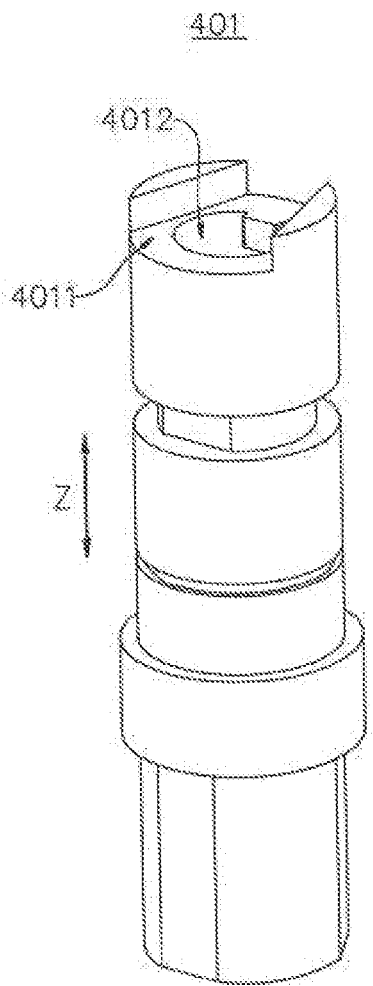
FIG. 28 is a structural schematic view of a rotating shaft of the driving mechanism provided in some embodiments of the present disclosure.

According to some embodiments of the present disclosure, referring to FIG. 19, and on this basis, with reference to FIG. 27 and FIG. 28, FIG. 27 is a structural schematic view of the driving mechanism 400 of the gene detection device 1000 provided in some embodiments of the present disclosure, and FIG. 28 is a structural schematic view of a rotating shaft 401 of the driving mechanism 400 provided in some embodiments of the present disclosure. The driving mechanism 400 includes a rotating shaft 401 and a first driving assembly 402. The rotating shaft 401 is rotatably provided on the frame 200, the rotating shaft 401 extends along the axial direction of the piston cylinder 20 (the third direction Z), and one end of the rotating shaft 401 in the axial direction of the piston cylinder 20 (the third direction Z) is configured to be detachably connected to the piston cylinder 20. The first driving assembly 402 is connected to the rotating shaft 401, and the first driving assembly 402 is configured to drive the rotating shaft 401 to rotate relative to the frame 200, so as to drive the piston cylinder 20 to circumferentially rotate relative to the kit body 10.

The rotating shaft 401 is rotatably mounted on the frame 200, and one end of the rotating shaft 401 is configured to be detachably connected to the piston cylinder 20 of the gene detection kit 100, so as to facilitate quick disassembly and mounting between the rotating shaft 401 and the piston cylinder 20, and further the first driving assembly 402, when driving the rotating shaft 401 to rotate, can drive the piston cylinder 20 to circumferentially rotate relative to the kit body 10.

In the above, the driving mechanism 400 further includes a mounting plate 403, and the mounting plate 403 is configured to be mounted to the mounting table 201 of the frame 200. The rotating shaft 401 is rotatably provided on the mounting plate 403 around an axis thereof (the axis of the rotating shaft 401 is arranged along the third direction Z). One end of the rotating shaft 401 in the third direction Z is configured to be detachably connected to one end of the piston cylinder 20 (as shown in FIG. 2) of the gene detection kit 100. The first driving assembly 402 is mounted on the mounting plate 403 and the first driving assembly 402 is configured to drive the rotating shaft 401 to rotate relative to the mounting plate 403, so as to drive the piston cylinder 20 of the gene detection kit 100 to circumferentially rotate relative to the kit body 10.

Optionally, the first driving assembly 402 includes a first driving member 4021 and a first transmission unit 4022, wherein both the first driving member 4021 and the first transmission unit 4022 are mounted on the mounting plate 403, and the first driving member 4021 is in transmission connection with the rotating shaft 401 through the first transmission unit 4022, so as to drive the rotating shaft 401 to rotate relative to the mounting plate 403. The first driving assembly 402 of such a structure can effectively adjust a driving force and a driving direction of the first driving member 4021 on the rotating shaft 401 through the first transmission unit 4022, thus facilitating practical use. Without doubt, it should be noted that, in some embodiments, it is also feasible that the first driving assembly 402 is not provided with the first transmission unit 4022, and an output end of the first driving member 4021 is directly connected to the rotating shaft 401 so as to drive the rotating shaft 401 to rotate relative to the mounting plate 403.

Exemplarily, the first driving member 4021 is a motor, and the first transmission unit 4022 is of a synchronous pulley structure. For a specific structure of the first transmission unit, reference can be made to the related art, and details will not be described herein again. In other embodiments, the first driving member 4021 also may be a hydraulic motor or the like, and the first transmission unit 4022 also may be of a gear-rack structure or a gear-chain structure, etc.

According to some embodiments of the present disclosure, as shown in FIG. 27 and FIG. 28, one end of the rotating shaft 401 in the axial direction of the piston cylinder 20 (the third direction Z) is provided with a butt-joint groove 4011 in which the operation portion 29 (as shown in FIG. 8) of the piston cylinder 20 is clamped.

By providing the butt-joint groove 4011 in which the operation portion 29 of the piston cylinder 20 is clamped at one end of the rotating shaft 401, detachable connection between the rotating shaft 401 and the piston cylinder 20 is realized by means of clamping, so that when the gene detection kit 100 is driven by the positioning seat 302 to move to the operation position along the first direction X, automatic connection between the operation portion 29 of the piston cylinder 20 and the rotating shaft 401 can be realized, manual intervention can be further reduced, which is beneficial to improve the operation efficiency of the gene detection device 1000, and the potential safety hazard existing in the process of using the gene detection device 1000 can be effectively reduced.

In the above, the operation portion 29 of the piston cylinder 20 is of a wedge-shaped structure (as shown in FIG. 8), and the butt-joint groove 4011 of the rotating shaft 401 can be snapped with the operation portion 29 of the piston cylinder 20, that is, the butt-joint groove 4011 of the rotating shaft 401 has a shape matched with the outer contour of the operation portion 29 of the piston cylinder 20, thus, the detachable connection between the rotating shaft 401 and the piston cylinder 20 is realized through this structure, so that after the operation portion 29 of the piston cylinder 20 is clamped in the butt-joint groove 4011, the rotating shaft 401 can be driven to circumferentially rotate relative to the kit body 10. In other embodiments, the rotating shaft 401 and the operation portion 29 of the piston cylinder 20 also may be detachably connected in other manners, for example, the butt-joint groove 4011 is provided on the operation portion 29 of the rotating shaft 401, and one end of the rotating shaft 401 in the third direction Z is provided as a wedge-shaped structure, so that the rotating shaft 401, after having one end being clamped in the butt-joint groove 4011 on the piston cylinder 20, can drive the piston cylinder 20 to circumferentially rotate relative to the kit body 10. Without doubt, the rotating shaft 401 and the operation portion 29 of the piston cylinder 20 also may be connected by bolt screwing or pin bolting, etc.

Based on the above structure, with continued reference to FIG. 27 and FIG. 28, the rotating shaft 401 is of a hollow structure with two open ends, the rotating shaft 401 is configured to be inserted by the magnetic member, and the magnetic member is configured to adsorb the magnetic beads in the piston cavity 21. By providing the rotating shaft 401 as a hollow structure with two open ends in an extending direction thereof, the magnetic member can be inserted into the rotating shaft 401, so that the magnetic member can abut against the piston cylinder 20 and act on the magnetic beads in the piston cavity 21 in the process of nucleic acid extraction. With such a structure, the distance between the magnetic member and the piston cylinder 20 can be effectively shortened, further being beneficial to enhance the magnetic force of the magnetic member to the magnetic beads in the piston cavity 21.

In the above, the rotating shaft 401 is of a hollow structure with two open ends, that is, a fourth through hole 4012 extending along the third direction Z is formed inside the rotating shaft 401. In the third direction Z, one end of the fourth through hole 4012 penetrates through one end of the rotating shaft 401 away from the butt-joint groove 4011, and the other end of the fourth through hole 4012 penetrates through a groove bottom wall of the butt-joint groove 4011, so that when moving along the third direction Z in the fourth through hole 4012, the magnetic member can extend out from the groove bottom wall of the butt-joint groove 4011 or retract into the fourth through hole 4012. In the process that the gene detection device 1000 extracts the nucleic acid for the gene detecting kit 100, after the operation portion 29 of the piston cylinder 20 is clamped in the butt-joint groove 4011, if the magnetic member is required to adsorb the magnetic beads, so as to prevent the magnetic beads from being discharged with the reagent from the first channel 22 (as shown in FIG. 9) of the piston cylinder 20, the magnetic member can move in the fourth through hole 4012 of the rotating shaft 401 and extend out from the groove bottom wall of the butt-joint groove 4011, so that one end of the magnetic member extends into the magnetic cavity 28 (as shown in FIG. 9) of the piston cylinder 20, which helps to improve the magnetic effect on the magnetic beads, and on the contrary, the magnetic member moves in the fourth through hole 4012 of the rotating shaft 401 and retracts into the fourth through hole 4012.

Exemplarily, the magnetic member is a magnetic bar provided in the fourth through hole 4012 of the rotating shaft 401, and the magnetic member extends along the third direction Z.

Optionally, referring to what is shown in FIG. 27, the driving mechanism 400 further can include a magnetic member driving device 404, wherein the magnetic member driving device 404 is mounted on the mounting plate 403, the magnetic member driving device 404 is configured to drive the magnetic member to move along the third direction Z in the fourth through hole 4012, so as to control whether the magnetic member is inserted into the magnetic cavity 28 of the piston cylinder 20 according to practical requirements, thus facilitating improving the automation degree of the gene detection device 1000, so as to save manual work. For a specific structure of the magnetic member driving device 404, reference can be made to the related art, and details will not be described herein again.

Figure 29:
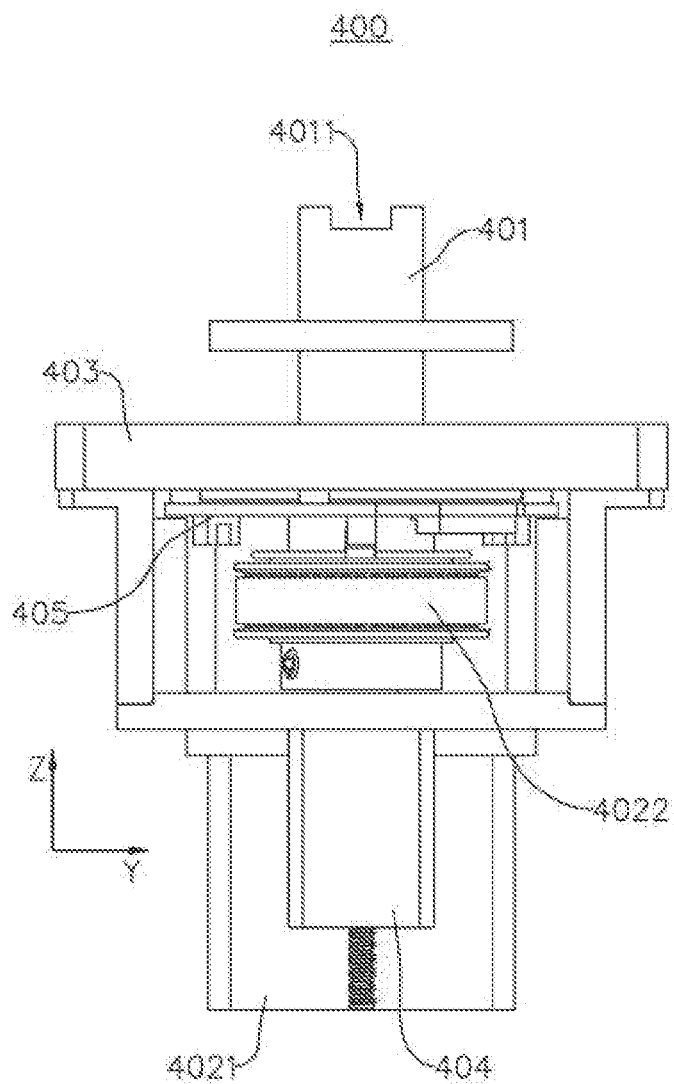
FIG. 29 is a rear view of the driving mechanism of the gene detection device provided in some embodiments of the present disclosure.

According to some embodiments of the present disclosure, with reference to FIG. 29, FIG. 29 is a rear view of the driving mechanism 400 of the gene detection device 1000 provided in some embodiments of the present disclosure. The driving mechanism 400 further includes a detection assembly 405, wherein the detection assembly 405 is configured to detect an angle of rotation of the rotating shaft 401 relative to the frame 200.

The rotation angle of the rotating shaft 401 can be detected by the detection assembly 405, then accuracy of rotation of the rotating shaft 401 relative to the frame 200 can be improved, so as to control the accuracy of circumferential rotation of the piston cylinder 20 relative to the kit body 10, further being beneficial to the control accuracy of the gene detection device 1000, thus ensuring smooth progress of the nucleic acid extraction work.

Based on the above structure, the detection assembly 405 includes a plurality of sensors, wherein the plurality of sensors are all mounted on the mounting plate 403, the plurality of sensors are arranged at intervals along the circumferential direction of the rotating shaft 401 and are uniformly arranged on the mounting plate 403, and the plurality of sensors are configured to cooperate to detect the rotation angle of the rotating shaft 401 relative to the mounting plate 403.

In the above, as the gene detection kit 100 is provided with six reagent cavities 12, the communication between the first channel 22 of the piston cylinder 20 and the second channel 13 of corresponding reagent cavity 12 can be realized by circumferentially rotating the piston cylinder 20 relative to the kit body 10 by sixty degrees, likewise, the detection assembly 405 includes six sensors, and in the circumferential direction of the rotating shaft 401, an angle between every two adjacent sensors is sixty degrees, so that each sensor is corresponding to one reagent cavity 12, thus the angle of each rotation of the rotating shaft 401 relative to the mounting plate 403 can be detected by the six sensors, respectively, so as to control the angle of circumferential rotation of the piston cylinder 20 relative to the kit body 10.

Exemplarily, the sensor is a photoelectric sensor, and a sensing element cooperating with the sensor is provided on the outer circumferential surface of the rotating shaft 401. When the rotating shaft 401 is rotated relative to the mounting plate 403, the sensing element is rotated to a position where any one of the six sensors is located, the corresponding sensor sends a detection signal, that is to say, each sensor is corresponding to one reagent cavity 12. When the rotating shaft 401 drives the piston cylinder 20 to circumferentially rotate relative to the kit body 10, if the sensor corresponding to one reagent cavity 12 of the six reagent cavities 12 sends a detection signal, the first channel 22 of the piston cylinder 20 is in communication with the second channel 13 of the reagent cavity 12, so that the rotation angle of the rotating shaft 401 can be controlled by the detection signal, so as to control the angle of circumferential rotation of the piston cylinder 20 relative to the kit body 10, and further the rotation angle of the piston cylinder 20 can be accurately controlled. Without doubt, in other embodiments, the sensor also may be a proximity switch or the like.

Figure 30:
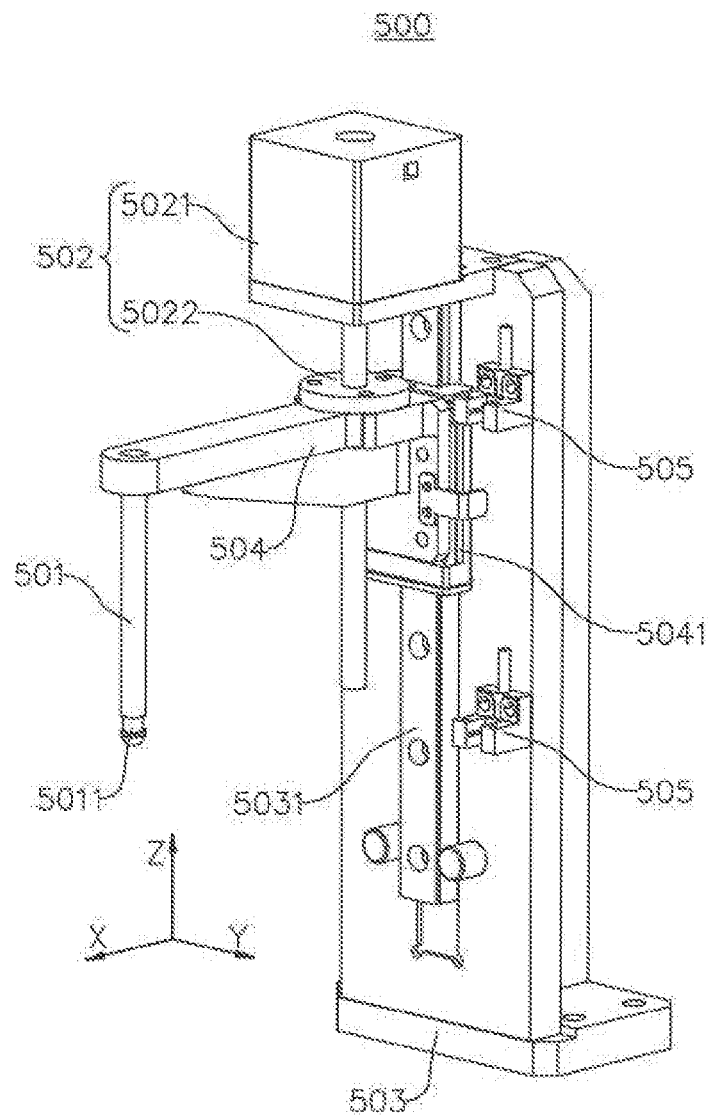
FIG. 30 is a structural schematic view of an executing mechanism of the gene detection device provided in some embodiments of the present disclosure.

According to some embodiments of the present disclosure, referring to FIG. 19, and on this basis, with reference to FIG. 30, FIG. 30 is a structural schematic view of the executing mechanism 500 of the gene detection device 1000 provided in some embodiments of the present disclosure. The executing mechanism 500 includes a piston rod 501 and a second driving assembly 502. The piston rod 501 is movably provided on the frame 200 along the axial direction of the piston cylinder 20 (the third direction Z). At least a part of the piston rod 501 is configured to extend into the piston cavity 21. The end of the piston rod 501 extending into the piston cavity 21 has an execution end 5011, and the execution end 5011 is configured to be connected to the piston 30. The second driving assembly 502 is connected to the piston rod 501, and the second driving assembly 502 is configured to drive the piston rod 501 to move relative to the frame 200 along the axial direction of the piston cylinder 20 (the third direction Z), so as to drive the piston 30 to move along the axial direction of the piston cylinder 20 (the third direction Z) in the piston cavity 21. The piston rod 501 can be driven by the second driving assembly 502 to move along the third direction Z, so that at least a part of the piston rod 501 can extend into the piston cavity 21, thus, after the execution end 5011 of the piston rod 501 is connected to the piston 30, the piston rod 501 can be driven by the second driving assembly 502 to drive movement of the piston 30 in the piston cavity 21, so as to realize the automation of the reagent exchange work between the piston cavity 21 and the reagent cavity 12.

In the above, the executing mechanism 500 further includes a mounting seat 503, wherein the mounting seat 503 is mounted on the mounting table 201 of the frame 200, the piston rod 501 extends along the third direction Z and is movably provided on the mounting seat 503 along the third direction Z, the second driving assembly 502 is connected to the mounting seat 503, and the second driving assembly 502 is configured to drive the piston rod 501 to move along the third direction Z relative to the mounting seat 503.

Based on the above structure, the executing mechanism 500 further includes a moving seat 504, wherein the moving seat 504 is movably connected to the mounting seat 503 along the third direction Z, the piston rod 501 is connected to the moving seat 504, and the second driving assembly 502 is configured to drive the moving seat 504 to move relative to the mounting seat 503 along the third direction Z, and thus can drive the piston rod 501 to move relative to the mounting seat 503 along the third direction Z.

Exemplarily, the mounting seat 503 is provided thereon with a second slide rail 5031 extending along the third direction Z, and the moving seat 504 has a second slider 5041 cooperating with the second slide rail 5031, so that the moving seat 504 can move relative to the mounting seat 503 along the third direction Z.

Optionally, as shown in FIG. 30, the second driving assembly 502 includes a second driving member 5021 and a second transmission unit 5022, wherein the second driving member 5021 is mounted on the mounting seat 503, and the second driving member 5021 is in transmission connection with the moving seat 504 through the second transmission unit 5022, so as to drive the moving seat 504 to move relative to the mounting seat 503 along the third direction Z. With the second driving assembly 502 of such a structure, the driving force and the driving direction of the second driving member 5021 acting on the piston rod 501 can be effectively adjusted through the second transmission unit 5022, thus facilitating practical application and use. Without doubt, it should be noted that, in some embodiments, it is also feasible that the second driving assembly 502 is not provided with the second transmission unit 5022, and an output end of the second driving member 5021 is directly connected to the moving seat 504, so as to drive the moving seat 504 to move relative to the mounting seat 503 along the third direction Z, for example, the second driving member 5021 is an air cylinder, an electric push rod, or the like.

Exemplarily, the second driving member 5021 is a motor, the second transmission unit 5022 is of a screw rod and a screw rod sleeve structure, the screw rod is connected to an output shaft of the second driving member 5021, the screw rod is arranged along the third direction Z, and the screw rod sleeve is sheathed on an outer circumferential side of the screw rod and is connected to the moving seat 504, thus, by driving the screw rod to rotate circumferentially by the second driving member 5021, the screw rod sleeve can be driven to move along the third direction Z, so as to drive the moving seat 504 to move relative to the mounting seat 503 along the third direction Z. In other embodiments, the second driving member 5021 also may be a hydraulic motor or the like, and the second transmission unit 5022 also may be of a gear-rack structure, etc.

According to some embodiments of the present disclosure, referring to what is shown in FIG. 3 and FIG. 30, one end of the piston 30 in the axial direction of the piston cylinder 20 (the third direction Z) is provided with a clamping groove 31, and the clamping groove 31 is configured to be snapped with the execution end 5011. By providing the clamping groove 31 in which the execution end 5011 of the piston rod 501 is clamped at one side of the piston 30, the detachable connection between the execution end 5011 of the piston rod 501 and the piston 30 is realized, which, on the one hand, facilitates the connection of the execution end 5011 of the piston rod 501, after being inserted into the piston cavity 21, to the piston 30, and on the other hand, facilitates the detachment of the execution end 5011 of the piston rod 501 from the piston 30 after the nucleic acid extraction work of the sample is completed.

In the above, the execution end 5011 of the piston rod 501 has an outer contour matched with a shape of the clamping groove 31 provided on the piston 30, so that the execution end 5011 of the piston rod 501, after being clamped in the clamping groove 31, can drive the piston 30 to move in the piston cavity 21. As the piston 30 is of a rubber structure and has certain flexibility, it is convenient to clamp and withdraw the execution end 5011 of the piston rod 501.

Based on the above structure, the piston rod 501 has a first position and a second position in the axial direction of the piston cylinder 20 (the third direction Z). When the piston rod 501 is located at the first position, the execution end 5011 of the piston rod 501 can be clamped in the clamping groove 31 of the piston 30, and when the piston rod 501 is located at the second position, the execution end 5011 of the piston rod 501 can exit from the clamping groove 31 of the piston 30. The second driving assembly 502 is configured to drive the piston rod 501 to move between the first position and the second position along the axial direction of the piston cylinder 20 (the third direction Z). The piston rod 501 can be to driven by the second driving assembly 502 to move between the first position and the second position along the third direction Z, so that the execution end 5011 of the piston rod 501, driven by the second driving assembly 502, can be automatically clamped in the clamping groove 31 of the piston 30 or automatically exit from the clamping groove 31 of the piston 30, thus, the degree of automation of the gene detection device 1000 is further improved, so as to achieve automatic connection and automatic detachment between the piston rod 501 and the piston 30.

That is to say, when the second driving assembly 502 drives the piston rod 501 to move to the first position, as the piston 30 will be blocked by a bottom surface (as shown in FIG. 2) of the piston cavity 21 and the piston 30 has certain flexibility, the piston rod 501 can be clamped in the clamping groove 31 under the action of the second driving assembly 502, and on the contrary, when the second driving assembly 502 drives the piston rod 501 to move to the second position, as the piston 30 will be blocked by the end cover 90 (as shown in FIG. 2) and the piston 30 has certain flexibility, the piston rod 501 can exit from the clamping groove 31 under the action of the second driving assembly 502, so as to achieve the automatic connection and detachment between the piston rod 501 and the piston 30.

Optionally, with continued reference to what is shown in FIG. 30, the executing mechanism 500 further includes two limiting sensors 505, wherein the two limiting sensors 505 are arranged at intervals on the frame 200 in the axial direction of the piston cylinder 20 (the third direction Z), and the two limiting sensors 505 are respectively configured to limit the first position and the second position of the piston rod 501 in the axial direction of the piston cylinder 20 (the third direction Z).

By providing two limiting sensors 505 at intervals on the frame 200 along the third direction Z, the two limiting sensors 505 can limit a moving stroke of the piston rod 501 in the third direction Z, thus, the piston rod 501 is limited to move between the first position and the second position, further facilitating the control over the moving stroke of the piston rod 501, so as to reduce the phenomenon of damage to the gene detection kit 100 positioned on the positioning mechanism 300 caused by excessive movement of the piston rod 501.

Exemplarily, the two limiting sensors 505 are both proximity switches.

According to some embodiments of the present disclosure, referring to what is shown in FIG. 19, the gene detection device 1000 further may include two heating mechanisms 800, wherein the two heating mechanisms 800 are oppositely mounted at intervals on the mounting table 201 of the frame 200 along the second direction Y, and when the gene detection kit 100 is positioned on the positioning mechanism 300, the two heating mechanisms 800 are respectively located at two sides of the gene detection kit 100 in the second direction Y, and the two heating mechanisms 800 are respectively configured to heat the lysing cavity 121 and the elution cavity 123 of the kit body 10 of the gene detection kit 100, thus, it is beneficial to improve the effect of lysing performed in the lysing cavity 121 and the effect of elution performed in the elution cavity 123 for the sample. For a specific structure of the heating mechanisms 800, reference can be made to the related art, and details will not be described herein again.

In conclusion, referring to what is shown in FIG. 1 to FIG. 4 and FIG. 19 to FIG. 30, the working process of extracting nucleic acid by the gene detection device 1000 is as follows:

firstly, the door 700 is opened, so that the positioning seat 302 of the positioning mechanism 300 is driven by the door 700 to move to the placement position along the first direction X, and the gene detection kit 100 pre-filled with the sample and the reagents is placed into the positioning groove 3021 of the positioning seat 302 through the placement port 601;

the door 700 is closed, so that the positioning seat 302 of the positioning mechanism 300 is driven by the door 700 to move to the operation position along the first direction X, wherein during the movement, the limiting part 3031 of the limiting component 303, under the guidance of the second guide slope 3015 of the fixing seat 301, can extend out from the upper surface of the positioning seat 302 in the third direction Z, so as to be abutted by one side of the gene detection kit 100 facing away from the executing mechanism 500 in the first direction X, thus preventing the gene detection kit 100 from exiting from the positioning groove 3021 during the movement of the positioning seat 302;

when the positioning seat 302 moves to the operation position along the first direction X, the operation portion 29 of the piston cylinder 20 of the gene detection kit 100 can be clamped in the butt-joint groove 4011 of the rotating shaft 401 of the driving mechanism 400, then, the piston rod 501 is driven by the second driving assembly 502 to move downwards along the third direction Z, so that the execution end 5011 of the piston rod 501 is inserted into the piston cavity 21 of the piston cylinder 20, and the execution end 5011 is clamped in the clamping groove 31 of the piston 30, thus the piston 30 can be driven by the piston rod 501 to move in the piston cavity 21 along the third direction Z;

after the sample has been lysed in the lysing cavity 121, the piston cylinder 20 is driven by the driving mechanism 400 to circumferentially rotate relative to the kit body 10, so that the first channel 22 of the piston cylinder 20 is in communication with the second channel 13 corresponding to the lysing cavity 121, and at this point, by driving the piston 30 by the piston rod 501 to move upwards along the third direction Z, the lysate in the lysing cavity 121 can be pumped into the piston cavity 21, so that the magnetic beads in the piston cavity 21 adsorb the nucleic acid lysed from the lysate;

after the magnetic beads have adsorbed the nucleic acid, the magnetic member is driven by a lifting mechanism to move along the third direction Z in the fourth through hole 4012 of the rotating shaft 401 and extends out from the groove bottom wall of the butt-joint groove 4011, so that the magnetic member is inserted into the magnetic cavity 28 of the piston cylinder 20 and magnetically attracts the magnetic beads, so that the magnetic beads are adsorbed in the magnetic bead retention tank 212 in the piston cavity 21, at this point, by driving the piston 30 by the piston rod 501 to move downwards along the third direction Z, the lysate can be discharged into the lysing cavity 121;

after the lysate is discharged out of the piston cavity 21, the magnetic member is driven by the lifting mechanism to move along the third direction Z in the fourth through hole 4012 of the rotating shaft 401 and retract into the fourth channel, thereafter, the piston cylinder 20 is driven by the driving mechanism 400 to circumferentially rotate relative to the kit body 10, such that the first channel 22 of the piston cylinder 20 is in communication with the second channel 13 corresponding to the washing cavity 122, at this point, by driving the piston 30 by the piston rod 501 to move upwards along the third direction Z, the washing solution in the washing cavity 122 can be pumped into the piston cavity 21, so as to wash the lysate remaining on the magnetic beads;

after the magnetic beads are washed by the washing solution, the magnetic member is driven by the lifting mechanism to move along the third direction Z in the fourth through hole 4012 of the rotating shaft 401 and extend out of the groove bottom wall of the butt-joint groove 4011, so that the magnetic member is inserted into the magnetic cavity 28 of the piston cylinder 20 and magnetically attracts the magnetic beads, so that the magnetic beads are adsorbed in the magnetic bead retention tank 212 in the piston cavity 21, at this point, by driving the piston 30 by the piston rod 501 to move downwards along the third direction Z, the washing solution can be discharged into the washing cavity 122;

after the washing solution is discharged out of the piston cavity 21, the magnetic member is driven by the lifting mechanism to move along the third direction Z in the fourth through hole 4012 of the rotating shaft 401 and retract into the fourth channel. As the gene detection kit 100 in the present embodiment has three washing cavities 122, the washing step is performed twice again on the magnetic beads;

thereafter, the piston cylinder 20 is driven by the driving mechanism 400 to circumferentially rotate relative to the kit body 10, so that the first channel 22 of the piston cylinder 20 is in communication with the second channel 13 corresponding to the elution cavity 123, and at this point, by driving the piston 30 by the piston rod 501 to move upwards along the third direction Z, the eluent in the elution cavity 123 can be pumped into the piston cavity 21, so that the nucleic acid adsorbed on the magnetic beads is dissolved in the eluent;

after the nucleic acid on the magnetic beads is dissolved in the eluent, the piston cylinder 20 is driven by the driving mechanism 400 to circumferentially rotate relative to the kit body 10, so that the first channel 22 of the piston cylinder 20 is in communication with the second channel 13 corresponding to the product output cavity 124, and the first hole section 161 and the second hole section 162 of the third channel 16 are in communication through the strip-shaped groove 24 on the outer circumferential surface of the piston cylinder 20, thereafter, the magnetic member is driven by the lifting mechanism to move along the third direction Z in the fourth through hole 4012 of the rotating shaft 401 and extend out of the groove bottom wall of the butt-joint groove 4011, so that the magnetic member is inserted into the magnetic cavity 28 of the piston cylinder 20 and magnetically attracts the magnetic beads, so that the magnetic beads are adsorbed in the magnetic bead retention tank 212 in the piston cavity 21, then by driving the piston 30 by the piston rod 501 to move downwards along the third direction Z, the eluent dissolved with the nucleic acid can be transported to the amplification reaction cavity 43 of the amplification reaction tube 40 for the nucleic acid amplification reaction;

after the eluent dissolved with the nucleic acid enters the amplification reaction tube 40, by driving the piston cylinder 20 by the driving mechanism 400 to circumferentially rotate relative to the kit body 10, the first channel 22 of the piston cylinder 20 is staggered from the second channel 13 corresponding to the product output cavity 124, and the first hole section 161 and the second hole section 162 of the third channel 16 are staggered from the strip-shaped groove 24 on the outer circumferential surface of the piston cylinder 20, so that the nucleic acid is subjected to the nucleic acid amplification reaction in the amplification reaction tube 40; and after the nucleic acid has completed the nucleic acid amplification reaction in the amplification reaction tube 40, the piston cylinder 20 is driven by the driving mechanism 400 to circumferentially rotate relative to the kit body 10, such that the first channel 22 of the piston cylinder 20 is again in communication with the second channel 13 corresponding to the product output cavity 124, furthermore, the first hole section 161 and the second hole section 162 of the third channel 16 are again in communication through the strip-shaped groove 24 on the outer circumferential surface of the piston cylinder 20, then, by driving the piston 30 by the piston rod 501 to move downwards along the third direction Z, the nucleic acid solution in the amplification reaction tube 40 can be discharged into the product output cavity 124 for subsequent gene detection, thus, the nucleic acid extraction work on the sample is completed through the above flow.

It should be noted that the embodiments in the present disclosure and the features in the embodiments may be combined with each other without conflict.

The above-mentioned are merely for preferred embodiments of the present disclosure, and not used to limit the present disclosure, and for those skilled in the art, various modifications and changes could be made to the present disclosure. Any modifications, equivalent substitutions, improvements and the like made within the spirit and principle of the present disclosure should be covered within the scope of protection of the present disclosure.

INDUSTRIAL APPLICABILITY

The present disclosure provides a gene detection kit and a gene detection device. For the gene detection kit of a special structure provided in the present disclosure, the communication between the first channel of the piston and the second channel corresponding to the product output is realized without providing components such as a switching valve, thus reducing the manufacturing costs, shortening the flow distance of the reagent exchanged between the piston cavity and the reagent cavities, reducing the butt-joint ports between the piston cavity and the reagent cavities, thus being beneficial to reduce the risk of liquid leakage, and having excellent application value.

What is claimed is:

1. A kit, comprising:
a kit body, wherein the kit body has an accommodating cavity and a plurality of reagent cavities;
a piston cylinder, wherein the piston cylinder is provided in the accommodating cavity, and the piston cylinder has a piston cavity; and
a piston, wherein the piston is movably provided in the piston cavity along an axial direction of the piston cylinder, wherein
a first channel in communication with the piston cavity is provided on an outer circumferential surface of the piston cylinder, a plurality of second channels are provided on an inner wall of the accommodating cavity, each of the second channels is in corresponding communication with one of the reagent cavities, and the piston cylinder can move relative to the kit body, so that the plurality of second channels are alternately in communication with the first channel,
wherein when the first channel is in communication with any one of the second channels, remaining second channels are blocked by the outer circumferential surface of the piston cylinder,
wherein the kit further comprises a first sealing member; and
the first sealing member is sleeved on the outer circumferential surface of the piston cylinder, and the first sealing member is provided with a first through hole in communication with the first channel at a position corresponding to the first channel.

2. The kit according to claim 1, wherein the outer circumferential surface of the piston cylinder is provided thereon with a first annular groove extending along a circumferential direction of the piston cylinder; and
the first annular groove is configured to accommodate the first sealing member, and the first channel is provided on a groove bottom wall of the first annular groove.

3. The kit according to claim 1, wherein in the axial direction of the piston cylinder, one end of the piston cylinder is provided with a first receptacle into which a piston rod is inserted, the first receptacle is provided opposite to a bottom surface of the piston cavity, the bottom surface of the piston cavity gradually gets away from the first receptacle from an edge to a center, and the first channel is connected to the center of the bottom surface of the piston cavity.

4. The kit according to claim 3, wherein a magnetic bead retention tank configured to accommodate magnetic beads is provided on the bottom surface of the piston cavity; and
in the axial direction of the piston cylinder, the magnetic bead retention tank is closer to the first receptacle than the center of the bottom surface of the piston cavity.

5. The kit according to claim 1, wherein the piston cylinder comprises a cylinder body and a partition wall; and
the partition wall is provided in the cylinder body and divides an inner space of the cylinder body into the piston cavity and a magnetic cavity, the piston cavity and the magnetic cavity are arranged along an axial direction of the cylinder body, the cylinder body has a first receptacle and a second receptacle at two ends in the axial direction thereof, the first receptacle is configured to allow a piston rod to be inserted into the piston cavity, the second receptacle is configured to allow a magnetic member to be inserted into the magnetic cavity, and the magnetic member is configured to adsorb magnetic beads.

6. The kit according to claim 1, wherein the plurality of reagent cavities are arranged along a circumferential direction of the piston cylinder.

7. The kit according to claim 6, wherein each of the reagent cavities has an opening at one end in the axial direction of the piston cylinder; and
the plurality of reagent cavities comprise a lysing cavity, a washing cavity, an elution cavity, and a product output cavity, in the axial direction of the piston cylinder, bottom surfaces of the lysing cavity, the washing cavity, and the elution cavity are provided opposite to respective openings, and the bottom surfaces of the lysing cavity, the washing cavity, and the elution cavity are all inclined surfaces, and are gradually away from the respective openings from a side away from the piston cylinder to a side close to the piston cylinder, and the second channels are connected to sides of the inclined surfaces close to the piston cylinder.

8. The kit according to claim 1, wherein the piston cylinder can be circumferentially rotated relative to the kit body, such that the plurality of second channels are alternately in communication with the first channel.

9. The kit according to claim 8, wherein the outer circumferential surface of the piston cylinder is provided with a limiting protrusion in a protruding way; and
 a limiting groove is provided on the inner wall of the accommodating cavity, and the limiting groove is configured to be snapped with the limiting protrusion, so as to restrict an axial movement of the piston cylinder relative to the kit body.

10. A device, configured to be used in association with the kit according to claim 1, wherein the device comprises:
 a frame;
 a positioning mechanism, wherein the positioning mechanism is mounted on the frame, and the positioning mechanism is configured to place and position the kit;
 a driving mechanism, wherein the driving mechanism is mounted on the frame, and the driving mechanism is configured to drive the piston cylinder to move relative to the kit body, so that the plurality of second channels are alternately in communication with the first channel; and
 an executing mechanism, wherein the executing mechanism is mounted on the frame, and the executing mechanism is configured to drive the piston to move in the piston cavity along the axial direction of the piston cylinder, so as to realize reagent exchange between the piston cavity and the reagent cavities.

11. The device according to claim 10, wherein the positioning mechanism comprises a fixing seat and a positioning seat;
 the fixing seat is fixedly mounted on the frame, and a second through hole through which the driving mechanism passes is provided on the fixing seat; and
 the positioning seat is movably provided on the fixing seat along a first direction, the positioning seat is configured to place and position the kit, the positioning seat has a placement position and an operation position in the first direction, wherein the first direction is perpendicular to the axial direction of the piston cylinder, and when the positioning seat is located in the placement position, the positioning seat is configured to allow taking and placing the kit, and when the positioning seat is located in the operation position, the driving mechanism can be connected to the piston cylinder.

12. The device according to claim 11, wherein the positioning seat is provided with a positioning groove at one side facing away from the positioning seat in the axial direction of the piston cylinder, and the positioning groove is configured to be snapped with the kit along the first direction so as to position the kit on the positioning seat; and
 an avoidance groove is provided on a groove bottom wall of the positioning groove, and when the positioning seat moves to the operation position along the first direction, the avoidance groove is configured to be snapped with the driving mechanism, so that the driving mechanism can be connected to the piston cylinder.

13. The device according to claim 12, wherein a groove side wall of the positioning groove has a first guide slope, and the first guide slope is configured to guide the kit into the positioning groove along the first direction.

14. The device according to claim 12, wherein the positioning mechanism further comprises a limiting component; and
 the limiting component is provided on the positioning seat, and the limiting component is configured to prevent the kit from exiting from the positioning groove along the first direction.

15. The device according to claim 11, wherein the fixing seat is provided thereon with a limiting stopper, and the limiting stopper is configured to be abutted by the positioning seat when the positioning seat moves to the operation position in the first direction.

16. The device according to claim 11, wherein the device further comprises a housing and a door;
 the housing is configured to accommodate the frame, and a placement port is provided at a position of the housing corresponding to the positioning mechanism;
 the door is movably provided on the housing, the door is configured to open or close the placement port, the door is in transmission connection with the positioning seat, and the door is configured to, when opening or closing the placement port, drive the positioning seat to move between the placement position and the operation position in the first direction.

17. The device according to claim 10, wherein the driving mechanism comprises a rotating shaft and a first driving assembly;
 the rotating shaft is rotatably provided on the frame, the rotating shaft extends along the axial direction of the piston cylinder, and one end of the rotating shaft in the axial direction of the piston cylinder is configured to be detachably connected to the piston cylinder; and
 the first driving assembly is connected to the rotating shaft, and the first driving assembly is configured to drive the rotating shaft to rotate relative to the frame, so as to drive the piston cylinder to circumferentially rotate relative to the kit body.

18. The device according to claim 10, wherein the executing mechanism comprises a piston rod and a second driving assembly;
 the piston rod is movably provided on the frame along the axial direction of the piston cylinder, at least a part of the piston rod is configured to extend into the piston cavity, an end of the piston rod extending into the piston cavity has an execution end, and the execution end is configured to be connected to the piston; and
 the second driving assembly is connected to the piston rod, and the second driving assembly is configured to drive the piston rod to move relative to the frame along the axial direction of the piston cylinder, so as to drive the piston to move along the axial direction of the piston cylinder in the piston cavity.

\* \* \* \* \*